(12) United States Patent
Bouma et al.

(10) Patent No.: US 8,158,585 B2
(45) Date of Patent: Apr. 17, 2012

(54) CROSS-β STRUCTURE COMPRISING AMYLOID-BINDING PROTEINS AND METHODS FOR DETECTION OF THE CROSS-β STRUCTURE, FOR MODULATING CROSS-β STRUCTURES FIBER FORMATION AND MODULATING CROSS-β STRUCTURE-MEDIATED TOXICITY

(75) Inventors: Barend Bouma, Houten (NL); Martin F. B. G. Gebbink, Eemnes (NL); Onno W. Kranenburg, Amsterdam (NL); Louise M. J. Kroon-Batenburg, Bunnik (NL)

(73) Assignee: CrossBeta Biosciences B.V., Utrecht (NL)

( * ) Notice: Subject to any disclaimer, the term of this patent is extended or adjusted under 35 U.S.C. 154(b) by 801 days.

(21) Appl. No.: 11/982,161

(22) Filed: Oct. 31, 2007

(65) Prior Publication Data

US 2008/0241165 A1 Oct. 2, 2008

Related U.S. Application Data

(60) Division of application No. 11/033,105, filed on Jan. 10, 2005, which is a continuation of application No. PCT/NL03/00501, filed on Jul. 8, 2003.

(30) Foreign Application Priority Data

Jul. 9, 2002 (EP) .................................... 02077797

(51) Int. Cl.
*A61K 38/02* (2006.01)
(52) U.S. Cl. ..................................... 514/17.8
(58) Field of Classification Search .................. None
See application file for complete search history.

(56) References Cited

U.S. PATENT DOCUMENTS

| | | |
|---|---|---|
| 5,051,185 A | 9/1991 | Watanabe et al. |
| 5,151,082 A | 9/1992 | Gorsuch et al. |
| 5,180,615 A | 1/1993 | Havens |
| 5,216,127 A | 6/1993 | Hirai et al. |
| 5,221,628 A | 6/1993 | Anderson et al. |
| 5,230,996 A | 7/1993 | Rath et al. |
| 5,276,059 A | 1/1994 | Caughey et al. |
| 5,278,189 A | 1/1994 | Rath et al. |
| 5,288,490 A | 2/1994 | Budzynski et al. |
| 5,449,663 A | 9/1995 | Bicher |
| 5,491,129 A | 2/1996 | Shaltiel |
| 5,589,154 A * | 12/1996 | Anderson ............... 424/1.41 |
| 5,591,431 A | 1/1997 | Schasteen et al. |
| 5,599,678 A | 2/1997 | Kraus et al. |
| 5,624,908 A | 4/1997 | Bicher |
| 5,650,418 A | 7/1997 | Rath et al. |
| 5,700,447 A | 12/1997 | Bucala et al. |
| 5,731,007 A | 3/1998 | Chung et al. |
| 5,733,524 A | 3/1998 | Bucala et al. |
| 5,733,933 A | 3/1998 | Bucala et al. |
| 5,750,349 A | 5/1998 | Suzuki |
| 5,780,587 A | 7/1998 | Potter |
| 5,780,615 A | 7/1998 | Bucala et al. |
| 5,785,187 A | 7/1998 | Lipman et al. |
| 5,786,324 A | 7/1998 | Gray et al. |
| 5,801,200 A | 9/1998 | Bucala et al. |
| 5,817,626 A | 10/1998 | Findeis et al. |
| 5,834,028 A | 11/1998 | Kunihiro et al. |
| 5,851,996 A | 12/1998 | Kline |
| 5,854,215 A | 12/1998 | Findeis et al. |
| 5,869,534 A | 2/1999 | Bucala et al. |
| 5,935,927 A | 8/1999 | Vitek et al. |
| 5,948,763 A | 9/1999 | Soto-Jara et al. |
| 5,955,343 A | 9/1999 | Holmes et al. |
| 5,958,883 A | 9/1999 | Snow |
| 5,981,697 A | 11/1999 | Kraus et al. |
| 5,985,242 A | 11/1999 | Findeis et al. |
| 5,985,607 A | 11/1999 | Delcuve et al. |
| 6,001,331 A | 12/1999 | Caprathe et al. |
| 6,034,211 A | 3/2000 | Kelly |
| 6,037,327 A | 3/2000 | Castillo et al. |
| 6,037,458 A | 3/2000 | Hirai et al. |
| 6,136,548 A | 10/2000 | Anderson |
| 6,161,547 A | 12/2000 | Barbut |
| 6,184,030 B1 | 2/2001 | Katoot et al. |
| 6,242,473 B1 | 6/2001 | Hellstrand et al. |
| 6,310,046 B1 | 10/2001 | Duffy et al. |
| 6,319,498 B1 | 11/2001 | Findeis et al. |
| 6,340,783 B1 | 1/2002 | Snow |
| 6,372,473 B1 | 4/2002 | Moore et al. |
| 6,399,314 B1 | 6/2002 | Krishnamurthy |
| 6,410,598 B1 | 6/2002 | Vitek et al. |

(Continued)

FOREIGN PATENT DOCUMENTS

| | | |
|---|---|---|
| AU | 2003214375 B2 | 10/2003 |
| DE | 197 35 902 A1 | 2/1999 |
| EP | 0 234 051 | 9/1987 |
| EP | 0 319 144 A1 | 6/1989 |
| EP | 0 321 703 A1 | 6/1989 |

(Continued)

OTHER PUBLICATIONS

Tucker et al. (J of Neuroscience 2000 vol. 20, p. 3937-3946).*
DeMattos et al. (PNAS 2001 vol. 98, p. 8850-8855).*
Golabek et al., The interaction between Apolipoprotein E and Alzheimer's amyloid beta-peptide is dependent on beta-peptide conformation. J Biol Chem 271(18): 10602-10606, 1996.

(Continued)

*Primary Examiner* — Daniel E Kolker
(74) *Attorney, Agent, or Firm* — TraskBritt, P.C.

(57) ABSTRACT

The invention relates to the field of biochemistry, molecular biology, structural biology and medicine. More in particular, the invention relates to cross-β structures and the biological role of these cross-β structures. In one embodiment, the invention discloses a method for modulating extracellular protein degradation and/or protein clearance comprising modulating cross-β(beta) structure formation (and/or cross-β structure-mediated activity) of the protein present in the circulation.

1 Claim, 22 Drawing Sheets

U.S. PATENT DOCUMENTS

Figure 1:
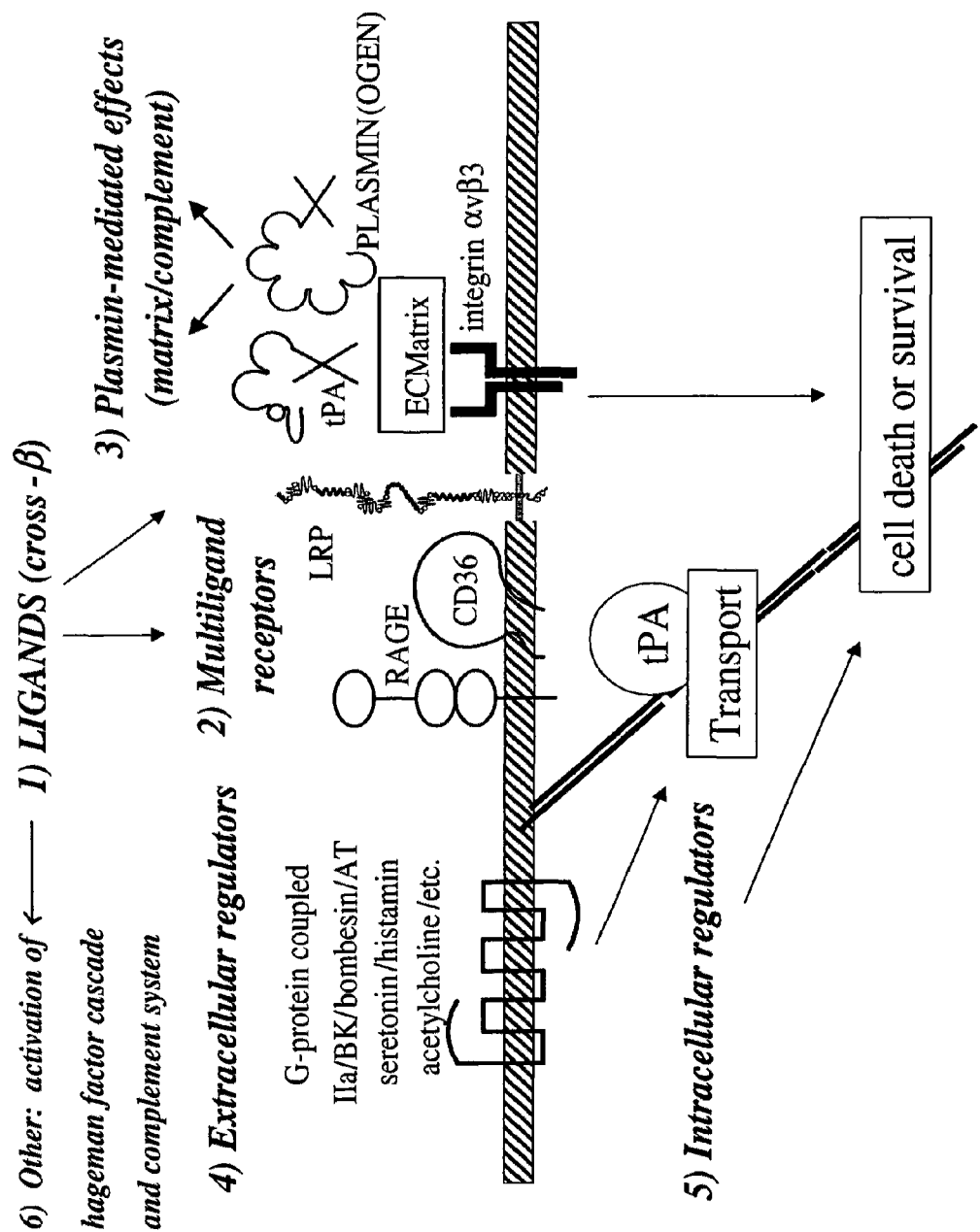

| | | | |
|---|---|---|---|
| 6,436,969 | B1 | 8/2002 | Khalifah et al. |
| 6,462,171 | B1 | 10/2002 | Soto-Jara et al. |
| 6,471,960 | B1 | 10/2002 | Anderson |
| 6,537,969 | B1 | 3/2003 | Blass |
| 6,641,815 | B2 | 11/2003 | Duffy et al. |
| 6,686,144 | B2 | 2/2004 | McLeod et al. |
| 6,689,275 | B1 | 2/2004 | Gupta |
| 6,960,465 | B1 | 11/2005 | Papoutsakis et al. |
| 7,041,287 | B2 | 5/2006 | Muzykantov et al. |
| 7,135,181 | B2 | 11/2006 | Jensen et al. |
| 7,172,875 | B2 | 2/2007 | Kuret et al. |
| 7,196,064 | B2 | 3/2007 | McAnalley et al. |
| 7,517,525 | B2 | 4/2009 | Prenner et al. |
| 2002/0065327 | A1 | 5/2002 | Jiao et al. |
| 2002/0102261 | A1* | 8/2002 | Raso ............... 424/146.1 |
| 2002/0114796 | A1 | 8/2002 | Eibl |
| 2002/0133019 | A1 | 9/2002 | Klunk et al. |
| 2002/0187157 | A1* | 12/2002 | Jensen et al. ........... 424/185.1 |
| 2002/0187158 | A1 | 12/2002 | Mahler et al. |
| 2003/0017995 | A1 | 1/2003 | Khalifah et al. |
| 2003/0050245 | A1 | 3/2003 | Gebbink et al. |
| 2003/0059921 | A1 | 3/2003 | Sahni et al. |
| 2003/0072770 | A1 | 4/2003 | McAnalley et al. |
| 2003/0086938 | A1 | 5/2003 | Jensen et al. |
| 2003/0087407 | A1 | 5/2003 | Soto-Jara et al. |
| 2003/0109435 | A1 | 6/2003 | Prenner et al. |
| 2003/0118593 | A1 | 6/2003 | Dan et al. |
| 2003/0143223 | A1 | 7/2003 | Cabezas et al. |
| 2003/0165458 | A1 | 9/2003 | Cabezas et al. |
| 2003/0176365 | A1 | 9/2003 | Blass |
| 2003/0236391 | A1 | 12/2003 | Klunk et al. |
| 2004/0013647 | A1 | 1/2004 | Solomon et al. |
| 2004/0253595 | A1 | 12/2004 | Nakamura et al. |
| 2005/0142208 | A1 | 6/2005 | Yoo et al. |
| 2005/0142611 | A1 | 6/2005 | Vodyanoy et al. |
| 2006/0045853 | A1 | 3/2006 | Kroon-Batenburg et al. |
| 2006/0058232 | A1 | 3/2006 | Luo et al. |
| 2006/0270599 | A1 | 11/2006 | Gebbink et al. |
| 2006/0292683 | A1 | 12/2006 | Gebbink et al. |
| 2007/0003552 | A1 | 1/2007 | Gebbink et al. |
| 2007/0015133 | A1 | 1/2007 | Gerard et al. |
| 2007/0015206 | A1 | 1/2007 | Gebbink et al. |
| 2007/0151133 | A1 | 7/2007 | Hunsaker |
| 2008/0044429 | A1 | 2/2008 | Johnson et al. |
| 2008/0118529 | A1 | 5/2008 | Gebbink et al. |
| 2008/0207488 | A1 | 8/2008 | Gebbink et al. |
| 2008/0220446 | A1 | 9/2008 | Gebbink et al. |
| 2008/0241165 | A1 | 10/2008 | Kroon-Batenburg et al. |
| 2008/0249606 | A1 | 10/2008 | Gebbink et al. |
| 2008/0267948 | A1 | 10/2008 | Gebbink et al. |
| 2008/0299212 | A1 | 12/2008 | Kim et al. |
| 2009/0142377 | A1 | 6/2009 | Gebbink et al. |
| 2009/0155254 | A1 | 6/2009 | Gebbink et al. |
| 2009/0191228 | A1 | 7/2009 | Gebbink et al. |
| 2009/0202980 | A1 | 8/2009 | Gebbink et al. |
| 2010/0015126 | A1 | 1/2010 | Gebbink et al. |

FOREIGN PATENT DOCUMENTS

| | | |
|---|---|---|
| EP | 0 494 848 A1 | 7/1992 |
| EP | 0589181 | 3/1994 |
| EP | 0 955 312 A2 | 11/1999 |
| EP | 1 130 031 A1 | 9/2001 |
| EP | 1 179 588 A1 | 2/2002 |
| EP | 1 152 004 B1 | 5/2003 |
| EP | 1 380 290 | 1/2004 |
| EP | 1 449 536 A1 | 8/2004 |
| EP | 1 978 362 A2 | 10/2008 |
| EP | 1 536 778 B1 | 12/2008 |
| EP | 1 257 582 B1 | 4/2009 |
| JP | 171638/1989 | 7/1998 |
| JP | 509457/1998 | 9/1998 |
| JP | 2001-519753 | 10/2001 |
| MO | 01/12598 A2 | 2/2001 |
| WO | WO 90/14102 | 11/1990 |
| WO | WO 91/18610 | 12/1991 |
| WO | WO 91/19488 | 12/1991 |
| WO | WO 92/11847 | 7/1992 |
| WO | WO 92/15677 | 9/1992 |
| WO | WO 94/01116 | 1/1994 |
| WO | WO 94/20083 | 9/1994 |
| WO | WO 94/28909 | 12/1994 |
| WO | WO 95/20979 | 8/1995 |
| WO | WO 96/15799 | 5/1996 |
| WO | WO 96/39834 | 12/1996 |
| WO | WO 97/21728 | 6/1997 |
| WO | WO 97/26919 | 7/1997 |
| WO | WO 97/46547 | 12/1997 |
| WO | WO 98/06418 | 2/1998 |
| WO | WO 99/02545 | 1/1999 |
| WO | WO 99/09999 | 3/1999 |
| WO | 99/21565 * | 5/1999 |
| WO | WO 99/21565 | 5/1999 |
| WO | WO 99/47072 | 9/1999 |
| WO | WO 00/04052 | 1/2000 |
| WO | WO 00 09562 A1 | 2/2000 |
| WO | WO 00/59493 | 10/2000 |
| WO | WO 00/66717 | 11/2000 |
| WO | WO 00/68263 | 11/2000 |
| WO | WO 01/07474 A1 | 2/2001 |
| WO | WO 01/12598 A2 | 2/2001 |
| WO | WO 01/50134 A2 | 7/2001 |
| WO | WO 01/53335 A3 | 7/2001 |
| WO | WO 01/58476 A2 | 8/2001 |
| WO | WO 01/62284 A2 | 8/2001 |
| WO | WO 01/62799 A2 | 8/2001 |
| WO | WO 01/77284 | 10/2001 |
| WO | WO 02/16333 A2 | 2/2002 |
| WO | WO 02/28441 | 4/2002 |
| WO | WO 02/053092 | 7/2002 |
| WO | WO 02/097444 A2 | 12/2002 |
| WO | WO 02/099098 A1 | 12/2002 |
| WO | WO03/002141 | 1/2003 |
| WO | WO 03/006893 A2 | 1/2003 |
| WO | WO 03/064446 A2 | 8/2003 |
| WO | WO 03/073106 A2 | 9/2003 |
| WO | WO 2004/004698 A2 | 1/2004 |
| WO | WO 2004/007545 | 1/2004 |
| WO | WO 2005/019434 A2 | 3/2005 |
| WO | WO 2005/042569 A1 | 5/2005 |
| WO | WO 2006/006172 A2 | 1/2006 |
| WO | WO 2006/098621 A2 | 9/2006 |
| WO | WO 2006/101387 | 9/2006 |
| WO | WO 2007/008069 A2 | 1/2007 |
| WO | WO 2007/008070 A2 | 1/2007 |
| WO | WO 2007/008071 A2 | 1/2007 |
| WO | WO 2007/008072 | 1/2007 |
| WO | WO 2007/008073 A2 | 1/2007 |
| WO | WO 2007/018400 A1 | 2/2007 |
| WO | WO 2007/094668 | 8/2007 |
| WO | WO 2007/108675 A1 | 9/2007 |

OTHER PUBLICATIONS

Wood et al., Abstract, Prolines and amyloidogenicity in fragments of the Alzheimer's peptide beta/A4. Biochemistry 34: 724-730, 1995.

Soto C et al., Abstract, Beta-sheet breaker peptides inhibit fibrillogenesis in a rat brain model of amyloidosis: implications for Alzheimer's therapy. Nat Med. 4(7):822-826, 1998.

Soto C et al., Abstract, Inhibition of Alzheimer's amyloidosis by peptides that prevent beta-sheet conformation. Biochem Biophys Res Commun. 226(3):672-680, 1996.

Permanne B et al., Reduction of amyloid load and cerebral damage in a transgenic mouse model of Alzheimer's disease by treatment with a beta-sheet breaker peptide. Faseb J. 16(8):860-862, 2002.

Hetenyi et al., Abstract, Computational studies on the binding of the beta-sheet breaker (BSB) peptides on amyloid betaA(1-42). J. Molec. Structure, 2001, pp. 25-31, vol. 542.

Bouma el al., "Glycation Induces Formation of Amyloid Cross-β Structure in Albumin," The Journal of Biological Chemistry, Oct. 24, 2003, pp. 41810-41819, vol. 278, No. 43.

Cardoso et al., "Aprotinin binding to amyloid fibrils," Eur. J. Biochem., 2000, pp. 2307-2311, vol. 267.

Chauhan et al., "Metal Cations Defibrillize the Amyloid Beta-Protein Fibrils," Neurochemical Research, 1997, pp. 805-809, vol. 22, No. 7.

Korol et al., "Glucose, memory, and aging," Am. J. Clin. Nutr., 1998, pp. 746S-771S, vol. 67 (Suppl.).

Maggio et al., "Brain Amyloid—A Physicochemical Perspective," Brain Pathology, 1996, pp. 147-162, vol. 6.

Reinbold, J., "Akuttherapie der diabetischen Notfalle," Notfallmedizin, 2002, pp. 82-84, vol. 28.

Testa et al, "The Effect of Different Glucose Endovenous Administrations on Amylin and Insulin Blood Concentration in Healthy Subjects," J. Biol. Res.—Boll. Soc. It. Biol. Sper., 1996, pp. 103-108, vol. 72, No. 3-4.

Kim et al., Thermodynamic beta-sheet propensities measured using a zinc-finger host peptide, Nature, 1993, pp. 267-270, vol. 362.

Levine III, et al., Screening for pharmacologic inhibitors of amyloid fibril formation, Methods Enzymol., 1999, pp. 467-476, vol. 309.

Minor et al., Context is a major determinant of beta-sheet propensity, Nature, 1994, pp. 264-267, vol. 371.

PCT International Preliminary Examination Report, PCT/NL03/00501, dated Oct. 28, 2004.

Walsh et al., Amyloid beta-protein fibrillogenesis, J. Biol. Chem., 1999, pp. 25945-25952, vol. 274.

Yutani et al., "The Process of Amyloid-like Fibril Formation by Methionine Aminopeptidase from a Hyperthermophile, *Pyrococcus furiosus*," Biochemistry, 2000, pp. 2769-2777, vol. 39.

Delgado et al., Antibodies against human cell receptors, CD36, CD41a and CD62P crossreact with porcine platelets, Cytometry Part B (Clinical Cytometry), 2003, pp. 62-67, vol. 56b.

Ockenhouse et al., Sequestrin, a CD36 recognition protein on Plasmodium falciparum malaria-infected erythrocytes identified by anti-idiotype antibodies, Proc. Natl. Acad. Sci. USA, 1991, pp. 3175-3179, vol. 88.

Chothia et al., Canonical structures for the hypervariable regions of immunoglobulins, J. Mol. Biol., 1987, pp. 901-917, vol. 196.

Adachi et al., Direct observation of photolysis-induced tertiary structural changes in hemoglobin, PNAS, Jun. 10, 2003, pp. 7039-7044, vol. 100, No. 12.

Baumketner et al., Amyloid beta-protein monomer structure: A computational and experimental study, Protein Science, 2006, pp. 420-428, vol. 15.

Bode et al., Antibody-directed Fibrinolysis, The Journal of Biological Chemistry (1989), pp. 944-948, vol. 264, No. 2.

Boehm et al., Antiangiogenic therapy of experimental cancer does not induce acquired drug resistance, Nature, 1997, pp. 404-407, vol. 390.

Bouma et al., Efficacy and Stability of a Subunit Vaccine Based on Glycoprotein E2 of Classical Swine Fever Virus, Vet Microbiol., 66, 101-114 (1999).

Bouma, B. et al., Adhesion Mechanism of Human Beta(2)-Glycoprotein 1 to Phospholipids Based on its Crystal Structure, EMBO J., 18, 5166-5174 (1999).

Brandenburg, K., Koch, M.H. & Seydel, T.J., Biophysical Characterisation of Lysozyme Binding to LPS Re and Lipid A, Eur. J. Biochem., 258, 686-695 (1998).

Butovsky, et al. Activation of Microglia by Aggregated Beta-Amyloid or Lipopolysaccharide Impairs MHC-II Expression and Renders them Cytotoxic whereas IFN-gamma and IL-4 Render them Protective, Mol. Cell Neurosci., (2005).

Claessen et al., A Novel Class of Secreted Hydrophobic Proteins is Involved in Aerial Hyphae formation in *Streptomyces coelicolor* by Forming Amyloid-like Fibrils, Genes & Development, 2003, pp. 1714-1726, vol. 17, Cold Spring Harbor Laboratory Press.

Cockerill et al., In vivo characterization of bioconjugate B cell toleragens with specificity for autoantibodies in antiphospholipid syndrome, International Immunopharmacology, Nov. 2003, pp. 1667-1675, vol. 3, No. 12.

Coraci et al., CD36, a Class B Scavenger Receptor, Is Expressed on Microglia in Alzheimer's Disease Brains and Can Mediate Production of Reactive Oxygen species in Response to β-Amyloid Fibrils, American Journal of Pathology, Jan. 2002, pp. 101-112, vol. 160, No. 1.

Cudic et al., Tetrahedron Letters, 2000, pp. 4527-4531, vol. 41.

De Laat, B., et al., IgG Antibodies That Recognize Epitope Gly40-Arg43 in Domain 1 of {beta}2-glycoprotein I Cause LAC and Their Presence Correlates Strongly with Thrombosis. Blood, 105, 1540-1545 (2005).

De Laat, et al., Beta2-glycoprotein I-dependent lupus anticoagulant highly correlates with thrombosis in the antiphospholipid syndrome, Blood, 104, 3598-3602 (2004).

Diaz-Avalos et al., Cross-beta Order and Diversity in Nanocrystals of an Amyloid-forming Peptide, Journal of Molecular Biology, 2003, pp. 1165-1175.

Doig et al., Binding of Laminin and Fibronectin by the Trypsin-resistant Major Structural Domain of the Crystalline Virulence Surface Array Protein of *Aeromonas salmonicida*, The Journal of Biological Chemistry, 1992, pp. 43-49, vol. 267, No. 1.

Dooley et al., Three-Dimensional Structure of an Open Form of the Surface Layer from the Fish Pathogen *Aeromonas salmonicida*, Journal of Bacteriology, Jan. 1989, pp. 190-197, vol. 171.

Dubois et al., Thrombin binding to GPIbalpha induces integrin alphaIIbbeta3 dependent platelet adhesion to fibrin in ex vivo flowing whole blood, Thrombosis and Haemostasis, Feb. 2004; pp. 233-237, vol. 91, No. 2.

Elangovan et al., The ubiquitin-interacting motif of 26S proteaosome subunit S5a induces A549 lung cancer cell death, Biophys. Res. Comm., 2007, pp. 226-230, vol. 364.

European Patent Office Notification for Application No. 03 762 927.6 dated Oct. 4, 2006.

European Patent Office Notification for Application No. 03 762 927.6 dated Jul. 26, 2007.

European Patent Office Oral Proceedings for Application No. 03 762 927.6 dated Feb. 18, 2008.

European Patent Office Summary of Facts and Submission for Application No. 03 762 927.6 dated May 30, 2008.

Faculty of 1000 Biology: Evaluations for Maas C et al., Biol Chem Jan. 26, 2007 282 (4): 2229-36, http://www.f1000biology.com/article/id/1060927/evaluation.

Fan et al., Preclinical study of influenza virus A M2 peptide conjugate vaccines in mice, ferrets, and rhesus monkeys, Vaccine, Aug. 13, 2004, pp. 2993-3003, vol. 22, No. 23-24, Butterworth Scientific, Guildford, GB.

Fassbender, K. et al., The LPS receptor (CDl4) Links Innate Immunity with Alzheimer's Disease, FASEB J., 18, 203-205 (2004).

Fleury et al., Abstract, Molecular assembly of plasminogen and tissue-type plasminogen activator on an evolving fibrin surface, Eur. J. Biochem., 1993, pp. 549-556, vol. 216.

Folkman, J., Clinical applications of research on angiogenesis, Semin. Med. Beth Israel Hosp., 1995b, pp. 1757-1763, vol. 333.

Folkman, J., Fighting cancer by attacking its blood supply, SE Am., 1996, pp. 150-154, vol. 275.

Folkman, Judah, Abstract, Angiogenesis in cancer, vascular, rheumatoid and other diseases, Nat. Med., 1995, pp. 27-31, vol. 1.

Frid et al., Congo red and protein aggregation in neurodegenerative diseases, Brain. Res. Rev., 2007, pp. 135-160, vol. 53, No. 1.

Fu et al. (2008) Sulfate stabilizes the folding intennediate more than the native structure of endostatin. Archives of Biochemistry and Biophysics 471: 232-239.

Fulmer, Tim, New Islets—No Immunosuppressives, Science-Business eXchange, Sep. 25, 2008, pp. 1-19, vol. 1, No. 34.

Garrido C. (2002) Size matters: of the small HSP27 and its large oligomers, Cell Death Differ., vol. 9, No. 5, pp. 483-485.

Ge et al., Fibrinogen Degradation Product Fragment D Induces Endothelial Cell Detachment by Activation of Cell-mediated Fibrinolysis, J. Clin. Invest, Dec. 1992, pp. 2508-2516, vol. 90.

Gebbink et al., Amyloids—A Functional Coat for Microorganisms, Nature Reviews Microbiology, Apr. 2005, pp. 333-341, vol. 3.

Genbank Public DNA Database, Accession No. 2B4X_I, Mourey et al., Sep. 27, 2005, pp. 1-3 <http://www.ncbi.nlm.nih.gov...> (visited Jan. 15, 2009).

Genbank Public DNA Database, Accession No. 2B4X_L, Mourey et al., Sep. 27, 2005, pp. 1-3 <http://www.ncbi.nlm.nih.gov...> (visited Jan. 15, 2009).

Geylis et al., Human monoclonal antibodies against amyloid-beta from healthy adults, Neurobiol. Aging, 2005, vol. 26, pp. 597-606.

Giannetti et al., Fibers of tau fragments, but not full length tau, exhibit a cross β-structure: Implications for the formation of paired helical filaments, Protein Science, 2000, pp. 2427-2434, vol. 9.

Goldsteins et al., Exposure of cryptic epitopes on transthyretin only in amyloid and in amyloidogenic mutants, Proceedings of the National Academy of Sciences of USA, Mar. 16, 1999, pp. 3108-3113, vol. 96, No. 6, National Academy of Science, Washington, DC, USA.

Gonzalez-McQuire et al., Fabrication of hydroxyapatite sponges by dextran sulphate/amino acid templating, Biomaterials, Jun. 3, 2005, pp. 6652-6656, vol. 26, No. 33.

Griffioen et al., Anginex, a designed peptide that inhibits angiogenesis, Biochem. J., 2001, pp. 233-242, vol. 354.

Grudzielanek et al., Solvational Tuning of the Unfolding, Aggregation and Amyloidogenesis of Insulin, Journal of Molecular Biology, Aug. 26, 2005, pp. 879-894, vol. 352, No. 4.

Gupta-Bansal et al., Congo red inhibits proteoglycan and serum amyloid P binding to amyloid beta fibrils, J. Neurochem. 1998, pp. 292-298, vol. 10, No. 1.

Gur et al., Editorial in Cell, Lon Takes in the Aromatic Fragrance of Unfolded Proteins, Genes Dev., 2008, pp. 2267-2277, vol. 22.

Han et al. (2007) Contributions of Zn(II)-binding to the structural stability of endostatin. FEBS Letters 581: 3027-3032.

Hatters et al., The molecular chaperone, alpha-crystallin, inhibits amyloid formation by apolipoprotein, C-11, J. Biol. Chem., 2001, pp. 33755-33761, vol. 276, No. 36.

He et al. (2006) Deficiency of disulfide bonds facilitating fibrillogenesis of endostatin. J. Biol. Chem. 281(2): 1048-1057.

Heckels et al., Vaccination Against Gonorrhoea: The Potential Protective Effect of Immunization with a Synthetic Peptide Containing a Conserved Epitope of Gonococcal Outer Membrane Protein 1B, Vaccine, Jun. 1, 1990, pp. 225-230, vol. 8, No. 3, Butterworth Scientific, Guildford, GB.

Hock et al., Generation of antibodies specific for beta-amyloid by vaccination of patients with Alzheimer disease, Nature Medicine, Nov. 2002, pp. 1270-1275, vol. 8, No. 11, Nature America, New York, US.

Hoppener et al., Islet Amyloid and Type 2 Diabetes Mellitus. N. Engl. J. Med., 343, 411-419 (2000).

Hoppener, J.W. et al., Extensive Islet Amyloid Fonnation Is Induced by Development of Type II Diabetes Mellitus and Contributes to Its Progression: Pathogenesis of Diabetes in a Mouse Mode, Diabetologia, 42, 427-434(1999).

Horbach et al., Lupus Anticoagulant is the Strongest Risk Factor for both Venous and Arterial Thrombosis in Patients with Systemic Lupus Erythematosus, Comparison between Different Assays for the Detection of Antiphospholipid Antibodies, Thromb. Haemost., 76, 916-924 (1996).

Horbach, et al., The Prevalence of a Non-phospholipid-binding Form of Beta2-Glycoprotein I in Human Plasma—Consequences for the Development of Anti-Beta2-glycoprotein 1 Antibodies. Thromb. Haemost., 80, 791-797 (1998).

Hrncic et al., Antibody-mediated resolution of light chain-associated amyloid deposits, American Journal of Pathology, Oct. 2000, pp. 1239-1246, vol. 157, No. 4, Philadelphia, PA, US.

Hu et al., Abstract, Procoagulant activity in cancer cells is dependent on tissue factor expression, Oncol Res., 1994, pp. 321-327, vol. 6, No. 7.

Hu et al., Angiogenin Enhances Actin Acceleration of Plasminogen Activation, Biochemical and Biophysical Communications, Dec. 15, 1993, pp. 682-687, vol. 197, No. 2.

Huang et al., Probing Three-Dimensional Structure of Bovine Serum Albumin by Chemical Cross-Linking and Mass Spectrometry, Journal of American Soc. Mass Spectrum, Aug. 2004, pp. 1237-1247, vol. 15, No. 8.

Hulst et al., Glycoprotein El of Hog Cholera Virus Expressed in Insect Cells Protects Swine from Hog Cholera, J Virol., 67, 5435-5442 (1993).

Husemann et al., Scavenger receptor class B type I (SR-Bi) mediates adhesion of neonatal murine microglia to fibrillar β-amyloid, Journal of Neuroimmunology, 2001, pp. 142-150, vol. 114.

Isik et al., Abstract, Vitronectin decreases microvascular endothelial cell apoptosis, J. Cell Physiol., May 1998, pp. 149-155, vol. 175, No. 2.

Jacobsen et al., Enhanced clearance of A beta in brain by sustaining the plasmin proteolysis cascade, PNAS, Jun. 24, 2008, pp. 8754-8759, vol. 105, No. 25.

Jhamb et al., Immobilized chaperones: A productive alternative to refolding of bacterial inclusion body proteins, Process Biochem., 2008, pp. 587-597, vol. 43.

Jurgens, G. et al., Investigation into the Interaction of Recombinant Human Serum Albumin with Re-lipopolysaccharide and Lipid A., J. Endotoxin. Res., 8, 115-126 (2002).

Kaganovich et al., Editorial in Cell, Misfolded Proteins Have a Parting of Ways, Nature, 2008, pp. 1088-1095, vol. 454.

Kawahara et al., Aluminum promotes the aggregation of Alzheimer's amyloid bet-protein in vitro, Biochemical and Biophysical Research Communications, Jan. 28, 1994, pp. 531-535, vol. 198, No. 2.

Kayed, R. et al., Common Structure of Soluble Amyloid Oligomers Implies Common Mechanism of Pathogenesis, Science, 300, 486-489 (2003) with Supporting Online Materials.

Keck et al., Proteasome inhibition by paired helical filament-tau in brains of patients with Alzheimer's disease, Journal of Neurochemistry, 2003, pp. 115-122, vol. 85.

Khoury et al., Microglia, Scavenger Receptors, and the Pathogenesis of Alzheimer's Disease, Neurobiology of Aging, 1998.

Kim et al., Molecular Packing of Lysozyme, Fibrinogen, and Bovine Serum Albumin on Hydrophilic and Hydrophobic Surfaces Studies by Infrared—Visible Sum Frequency Generation and Fluorescence Microscopy, J. Am. Chem. Soc., Articles, published on Web Feb. 12, 2003, pp. 3150-3158, vol. 125.

Kim Tae-Yoon et al., Both E7 and CpG-oligodeoxynucleotide are required for protective immunity against challenge with human papillomavirus 16 (E6/E7) immortalized tumor cells: Involvement of CD4+ and CD8+ T cells in protection, Cancer Research, Dec. 15, 2002, pp. 7234-7240, vol. 62, No. 24.

Korol et al., "Glucose, memory, and aging," Am. J. Clin. Nutr., 1998, pp. 7645-771S, vol. 67 (Suppl.).

Kost et al., Limited plasmin proteolysis of vitronectin. Characterization of the adhesion protein as morpho-regulatory and angiostatin-binding factor, European Journal of Biochemistry, Mar. 1, 1996, pp. 682-688, vol. 236, No. 2.

Kranenburg et al., "Tissue-Type Plasminogen Activator is a Multiligand Cross-Beta Structure Receptor," Current Biology, Oct. 29, 2002, pp. 1833-1839, vol. 12.

Kranenburg et al., Recombinant endostatin forms amyloid fibrils that bind and are cytotoxic to murine neuroblastoma cells in vitro, FEBS Letters, 2003, pp. 149-155.

Kuiper et al., Abstract, Clinical research on antiangiogenic therapy, Pharmacol Res., 1998, pp. 1-16, vol. 37, No. 1.

Landman, W.J., Arnyloid Arthropathy in Chickens, Vet. Q., 21, 78-82 (1999).

Levine et al. Induction of Anti Phospholipid Autoantibodies by Beta2-Glycoprotein I Bound to Apoptotic Thymocytes, J. Autoimmun., 11, 413-424 (1998).

Liu, Y. et al., LPS receptor (CD14): a Receptor for Phagocytosis of Alzheimer's Amyloid Peptide. Brain, (2005).

Lodish et al., Molecular Cell biology, 4th Edition, 2000, W.H. Freeman & Co., Figure 22.

Lowe et al., Journal of Molecular Recognition, 1998, pp. 194-199, vol. 11.

Lu Xiuhua et al., A mouse model for the evaluation of pathogenesis and immunity to influenza A (H5N1) viruses isolated from humans, Journal of Virology, Jul. 1999, pp. 5903-5911, vol. 73, No. 7, The American Soceity for Microbiology, US.

Lueking et al., Protein biochips: A new and versatile platform technology for molecular medicine, Drug. Discov. Today, 2005, pp. 789-794, vol. 10.

Luijkx, et al., Relative Immunogenicity of PorA Subtypes in a Multivalent *Neisseria meningitidis* Vaccine Is Not Dependent on Presentation Form, Infect Immun., 71, 6367-6371 (2003).

Lutters, et al. Dimers of Beta 2-Glycoprotein I Mimic the in Vitro Effects of Beta 2-Glycoprotein 1-Anti-Beta 2-Glycoprotein I Antibody Complexes., J. Biol. Chem., 276, 3060-3067 (2001).

Luykx et al., HPLC and tandem detections to monitor conformational properties of biopharmaceuticals, Journal of Chromatography B. 2005. pp. 45-52, vol. 821.

Maas et al., "A Role for Protein Misfolding in Immunogenicity of Biopharmaceuticals," J Biol Chem, Jan. 26, 2007, pp. 2229-2236, vol. 282, No. 4.

Maas et al., Editorial in Cell, Aggregates Set Off Factor XII, J. Clin. Invest., 2008, pp. 3208-3218, vol. 118.

Maas et al., Identification of fibronectin type I domains as amyloid-binding modules on tissue-type plasminogen activator and three homologs, Amyloid, Sep. 2008, pp. 166-180, vol. 15, No. 3.

Maas et al., Misfolded proteins activate Factor XII in humans, leading to kallikrein formation without initiating coagulation, Research article, The Journal of Clinical Investigation, Sep. 2008, pp. 3208-3218, vol. 118, No. 9. Maas et al., Identification of fibronectin type I domains as amyloid-binding modules on tissue-type plasminogen activator and three homologs, Amyloid, Sep. 2008, pp. 166-180, vol. 15, No. 3.

Machovich et al., Denatured Proteins as Cofactors for Plasminogen Activation, Archives of Biochemistry and Biophysics, Aug. 15, 1997, pp. 343-349, vol. 344, No. 2.

Machovich et al., Myosin as cofactor and substrate in fibrinolysis, FEBS Letters, 1997, pp. 93-96, vol. 407, No. 1.

Mackay et al., Protein interactions: is seeing believing?, Trends in Biochemical Sciences, 2007, pp. 530-531, vol. 32, No. 12.

Mahdavi et al., Vaccines Against Human Papillomavirus and Cervical Cancer: Promises and Challenges, The Oncologist, 2005, pp. 528-538, vol. 10.

Mandriota, et al., Vascular endothelial growth factor-induced in vitro angiogenesis and plasminogen activator expression are dependent on endogenous basic fibroblast growth factor, J. Cell Sci., 1997, pp. 2293-2302, vol. 110.

Marciani, Vaccine adjuvants: Role and mechanisms of action in vaccine immunogenicity, Drug Discovery Today, Oct. 15, 2003, pp. 934-943, vol. 8, No. 20.

Marks et al., Infective Endocarditis Successfully Treated in Extremely Low Birth Weight Infants With Recombinant Tissue Plasminogen Activator, Pediatrics, Jan. 2002, pp. 153-158, vol. 109, No. 1.

Marsh et al., The Structure of Tussah Silk Fibroin, World Scientific Series in 20th Century Chemistry—vol. 10, Selected Scientific Papers, pp. 1078-1083, vol. II—Biomolecular Sciences, reprinted from Acta Crystallographica, Nov. 1955, vol. 8, Part I I.

Matsuura et al., Anticardiolipin Antibodies Recognize Beta 2-Glycoprotein I Structure Altered by Interacting with an Oxygen Modified Solid Phase Surface, J. Exp. Med., 179, 457-462 (1994).

Matzinger, P, An Innate Sense of Danger, Ann. N.Y. Acad. Sci., 961, 341-342 (2002).

Morrison, et al., Direct Evidence for Hageman Factor (Factor XII) Activation by Bacterial Lipopolysaccharides (Endotoxins), J. Exp. Med., 140, 797-811 (1974).

Mueller et al., Editorial in Cell, Unruly Glycoproteins Are Discharged from the ER by SEL1L and Partners, Proc. Natl. Acad. Sci, 2008, pp. 12325-12330, vol. 105.

Munro et al., Consequences of the Non-specific Binding of a Protein to a Linear Polymer: Reconciliation of Stoichiometric and Equilibrium Titration Data for the Thrombin-Heparin Interaction, J. theor. Biol., 2000, pp. 407-418, vol. 203.

Muramatsu et al., In vitro evaluation of the heparin-coated Gyro C1E3 blood pump, Artificial Organs, Jul. 2001, pp. 585-590, vol. 25, No. 7.

Narang et al., Enhanced biosensor performance using an avidin-biotin bridge for antibody immobilization, Proc. SPIE, 1997, pp. 1987-1994, vol. 2980.

Nemes et al., Cross-linking of ubiquitin, HSP27, parkin and α-synuclein by γ-glutamyl-ε-lysine bonds in Alzheimer's neurofibrillary tangles, The FASEB Journal, Published online May 7, 2004.

Nesheim et al., Abstract, Thrombin, thrombomodulin and TAFI in the molecular link between coagulation and fibrinolysis, Thromb Haemost, Jul. 1997, pp. 386-391, vol. 78, No. 1.

Nguyen, Tam Luong, Three-dimensional Model of the Pore Form of Anthrax Protective Antigen. Structure and Biological Implications, Journal of Biomolecular Structure & Dynamics, 2004, pp. 253-265, vol. 22, No. 3.

Nieuwenhuizen et al., Identification of a Site in Fibrin(ogen) Which is Involved in the Acceleration of Plasminogen Activation by Tissue-Type Plasminogen Activator, Biochimica et Biopysica Acta, 1983, pp. 86-92, vol. 784.

NUNC (2009, updated) Immobilizer™ F96 MicroWell™ Plates (2009, updated) http://www.nuncbrand.com/us/page.aspx?ID_10212, p. 1.

Obrenovich et al., Glycation Stimulated Amyloid Formation, Sci. Aging Knowl. Environm., Jan. 14, 2004, pp. pe3, vol. 2004, No. 2.

O'Reilly et al., Endostatin: An Endogenous Inhibitor of Angiogenesis and Tumor Growth, Cell, Jan. 24, 1997, pp. 277-285.

O'Nuallain et al., Conformational Abs recognizing a generic amyloid fibril epitope, Proceedings of the National Academy of Sciences of USA, Feb. 5, 2002, pp. 1485-1490, vol. 99, No. 3, National Academy of Science, Washington, DC, USA.

Oomen et al., J. Mol. Biol., May 16, 2003, pp. 1083-1089, vol. 328, No. 5.

Orgel et al., The In Situ Supernnolecular Structure of Type I Collagen, Structure, Nov. 2001, pp. 1061-1069, vol. 9.

Ossowski et al., Abstract, Antibodies to plasminogen activator inhibit human tumor metastasis, Cell, Dec. 1983, pp. 611-619, vol. 35.

Ott et al., Enhancement of humoral response against human influenza vaccine with the simple submicron oil/water emulsion adjuvant MF59, Vaccine, 1995, pp. 1557-1562, vol. 13, No. 16.

Paris et al., Anti-angiogenic activity of the mutant Dutch Aβ peptide on human brain microvascular endothelial cells, Molecular Brain Research, 2005, pp. 212-230, vol. 136.

Paris et al., Inhibition of angiogenesis by Aβ peptides, Angiogenesis, 2004, pp. 75-85, vol. 7.

Partial European Search Report, EP 05 07 5656, dated Sep. 7, 2005.

PCT International Preliminary Examination Report, PCT/NL01/00155, dated May 10, 2002.

PCT International Search Report, PCT/NL01/00155, dated Sep. 4, 2001.

PCT International Search Report, PCT/NL2006/000143, dated Jan. 22, 2007.

PCT International Search Report, PCT/NL2006/000149, dated May 14, 2007.

PCT International Search Report, PCT/NL2006/000361, dated Mar. 29, 2007.

PCT International Search Report, PCT/NL2006/000362, dated Feb. 5, 2007.

PCT International Search Report, PCT/NL2006/000363, dated Dec. 21, 2006.

PCT International Search Report, PCT/NL2006/000364, dated Mar. 28, 2007.

PCT International Search Report, PCT/NL2006/000365, dated Jan. 12, 2007.

Poland, G.A., Vaccines against Avian Influenza—A Race against Time, N Engl J Med., 354, 1411-1413 (2006).

Radcliffe et al., A Critical Role of Lysine Residues in the Stimulation of Tissue Plasminogen Activator by Denatured Proteins and Fibrin Clots, Biochimica et Biopysica Acta, 1983, pp. 422-430, vol. 743.

Rao et al., Thermo and pH stable ATP-independent chaperone activity of heat-inducible Hsp70 from Pennisetum glaucum, Plant. Signal Behav., 2010, pp. 110-121, vol. 5, No. 2.

Reijerkerk et al., "No grip, no growth: the conceptual basis of excessive proteolysis in the treatment of cancer," European Journal of Cancer, 2000, pp. 1695-1705, vol. 36.

Renard et al., Catheter Complications Associated with Implantable Systems for Peritoneal Insulin Delivery, Diabetes Care, Mar. 1995, pp. 300-306, vol. 18, No. 3.

Rochet et al., Amyloid fibrillogenesis: themes and variations, Current Opinion in Structural Biology, 2000, pp. 60-68.

Rosenberg et al., "Effects of Protein Aggregates: An Immunologic Perspective," The AAPS Journal 2006, pp. E501-E507, vol. 8, No. 3.

Roth et al., Abstract, Differential Engagement of Platelet CD36 in Fibrin Clot Retraction Versus Aggregation, Blood and 45th Annual Meeting of the American Society of Hematology, Nov. 16, 2003, pp. 62b, vol. 102, No. 11.

Ruf et al., Abstract, Tissue factor in cancer angiogenesis and metastasis, Curr Opin Hematol., 1996, pp. 379-384, vol. 3, No. 5.

Salonen et al., (1985) Plasminogen and tissue-type plasminogen activator bind to immobilized fibronectin, J. Biol. Chem., vol. 260, No. 22, pp. 12302-12307.

Sara et al., Crystalline Bacterial Cell Surface Layers (S-Layers) from Cell Structure to Biomimetics, Prog. Biophys.. Molec. Biol., 1996, pp. 83-111, vol. 65.

Schmaier et al., The Elusive Physiologic Role of Factor XII, The Journal of Clinical Investigation, Sep. 2008, pp. 3006-3009, vol. 118, No. 9.

Schmidt et al., The biology of the receptor for advanced glycation end products and its ligands, Biochimica et Biophysica Acta, 2000, pp. 99-111, vol. 1498.

Serpell, Louise C., Alzheimer's amyloid fibrils: structure and assembly, Biochimica et Biophysica Acta, 2000, pp. 16-30, vol. 1502.

Sipe et al., Review: History of the Amyloid Fibril, Journal of Structural Biology, 2000, pp. 88-98.

Sousa et al., Familial Amyloid Polyneuropathy: Receptor for Advanced Glycation End Products-Dependent Triggering of Neuronal Inflammatory and Apoptotic Pathways, The Journal of Neuroscience, Oct. 1 2001, pp. 7576-7586, vol. 21, No. 19.

Sparknotes (2008, updated), Amino Acids and proteins, <http://www.sparknotes.com/health/aminoacids/section1.html>, pp. 1-7.

Speidel et al., Priming of Cytotoxic T Lymphocytes by Five Heataggregated Antigens in Vivo: Conditions, Efficiency, and Relation to Antibody Responses, European Journal of Immunology, /Sep. 1997, pp. 2391-2399, vol. 27, No. 9.

Stack et al., Abstract, Regulation of plasminogen activation by components of the extracellular matrix, Biochemistry, May 22, 1990, pp. 4966-4970, vol. 29, No. 20.

Steele et al., Editorial in Cell, HSFI Provides Protection from PrP, Proc. Natl. Acad. Sci., 2008, pp. 13626-13631, vol. 105.

Subang, R. et al., Phospholipid-Bound Beta2-GLycoprotein I Induces the Production of Anti-Phospholipid Antibodies, J. Autoimmun., 15, 21-32 (2000).

Sunde et al., "Common Core Structure of Amyloid Fibrils by Synchrotron X-ray Diffraction," J. Mol. Biol., 1997, pp. 729-739, vol. 273.

Takada et al., Detoxification of Lipopolysaccharide (LPS) by Egg White Lysozyme, FEMS Immunol. Med. Microbiol., 9, 255-263 (1994).

Tang et al., Anti-inflammatory properties of triblock siloxane copolymer-blended materials, Biomaterials, 1999, pp. 1365-1370, vol. 20, No. 15.

Thiru Malai et al., Emerging ideas on the molecular basis of protein and peptide aggregation, Curr. Opin. Struct. Biol., 2003, pp. 146-159, vol. 13, No. 2.

Tollis et al., Abstract, Recent Development in Avian Influenza Research: Epidemiology and Immuno prophylaxis, Veterinary Journal, 2002, pp. 202-215, vol. 164.

Torrent et al., Insights into alternative prion protein topologies induced under high hydrostatic pressure, J. Phys., Condense. Matter., 2004, pp. S1059-S1065, vol. 16, Issue 14.

Treanor et al., Dose-Related Safety and Immunogenicity of a Trivalent Baculovirus-Expressed Influenza-Virus Hemagglutinin Vaccine in Elderly Adults, J Infect Dis., 193, 1223-1228 (2006).

Treanor et al., Safety and Immunogenicity of an Inactivated Subvirion Influenza A (H5N1) Vaccine, N Engl J Med., 354, 1343-1351 (2006).

Tumpey et al., Mucosal delivery of inactivated influenza vaccine induces B-cell-dependent heterosubtypic cross-protection against lethal influenza A H5N1 virus infection, Journal of Virology, Jun. 2001, pp. 5141-5150, vol. 75, No. 11, The American Society for Microbiology, US.

Turn (biochemistry) (2009), available at http://en.wikipedia.ore/wiki/Beta-turn (last modified on Jul. 21, 2009).

UniProtKB/Swiss-Prot entry O97507, <http://www.expasy.org/cgi-bin/niceprot.pl/printable?ac=O97507>, Apr. 6, 2006 visited Feb. 25, 2008.

UniProtKB/Swiss-Prot entry P00748, <http://www.expasy.org/cgi-bin/niceprot.pl/printable?ac=p00748>, Jul. 21, 1986 visited Feb. 25, 2008.

UniProtKB/Swiss-Prot entry P98140, <http://www.expasy.org/cgi-bin/niceprot.pl/printable?ac=P98140>, Feb. 1, 1996 visited Feb. 25, 2008.

UniProtKB/Swiss-Prot entry Q04962, <http://www.expasy.org/cgi-bin/niceprot.pl/printable?ac=Q04962>, Feb. 1, 1996 visited Feb. 25, 2008.

UniProtKB/Swiss-Prot entry Q5M879, <http://www.uniprot.org/uniprot/Q5M8979>, Feb. 1, 2005 visited May 15, 2009.

UniProtKB/Swiss-Prot entry Q6PER0, <http://www.expasy.org/cgi-bin/niceprot.pl/printable?ac=Q6PER0>, Jul. 5, 2007 visited Feb. 25, 2008.

Van Beusekom et al., Abstract, Fibrin and basement membrane components, as a biocompatible and thromboresistant coating for metal stents, European Heart Journal, pp. 378, vol. 15.

Van Rijn et al., Classical Swine Fever Virus (CSFV) Envelope Glycoprotein E2 Containing One Structural Antigenic Unit Protects Pigs from Lethal CSFV Challenge, J Gen Virol., 77, 2737-2745 (1996).

Vartio et al., Monoclonal antibody against the N-terminal end of human plasma fibronectin, Biochem. J., 1983, pp. 147-151, vol. 215.

Vaughn et al., The establishment of two cell lines from the insect *Spodoptera frugiperda* (Lepidoptera; Noctuidae). In Vitro, 13, 213-217, (1977).

Verheijen et al., "Involvement of finger domain and kringle 2 domain of tissue-type plasminogen activator in fibrin binding and stimulation of activity by fibrin," EMBO 1986, vol. 5, pp. 3525-3530.

Vermeer, 1. "Uniquie protein structure offers a basis for commercial activity." Conceptuur, Dec. 2004, No. 41 (p. 18 is relevant and has been translated).

Voest, E.E., Abstract, Inhibitors of angiogenesis in a clinical perspective, Anticancer Drugs, Sep. 1996, pp. 723-727, vol. 7, No. 7.

Voropai et al. Spectral properties of thioflavin T and its complexes with amyloid fibrils, J. Appl. Spectrosc., 2003, pp. 868-874, vol. 70.

Wallberg et al., Vaccination with myelin oligodendrocyte glycoprotein adsorbed to alum effectively protects DBA/1 mice from experimental autoimmune encephalomyelitis, European Journal of Immunology, Jun. 2003, pp. 1539-1547, vol. 33, No. 6.

Wang et al., A Study of the Mechanism of Inhibition of Fibrinolysis by Activated Thrombin-activable Fibrinolysis Inhibitor, The Journal of Biological Chemistry, Oct. 16, 1996, pp. 27176-27181, vol. 273, No. 42.

Wang et al., Bacterial inclusion bodies contain amyloid-like structure, PLoS Biol., 2008, pp. 1791-1801, vol. 6, No. 8.

Welters et al., Chemically synthesized protein as tumour-specific vaccine: immunogenicity and efficacy of synthetic HPV16 E7 in the TC-1 mouse tumour model, Dec. 2, 2004, pp. 305-311, vol. 23, No. 3.

Wensvoort et al., Antigenic Differentiation of Pestivirus Strains with Monoclonal Antibodies Against Hog Cholera Virus, Vet Microbiol., 21, 9-20 (1989).

Wensvoort et al., Production of Monoclonal Antibodies Against Swine Fever Virus and Their Use in Laboratory Diagnosis, Vet Microbiol., 12, 101-108 (1986).

Wikipedia, 2009, updated, Hsp27, en.wikipedia.org/wiki/Hsp27, pp. 1-4.

Wilhelmus et al., Specific association of small heat shock proteins with the pathological hallmarks of Alzheimer's disease brains, Neuropathology and Applied Neurobiology, 2006, pp. 119-130, vol. 32.

Wu et al., The binding of thioflavin T and its neutral analog BTA-1 to protofibrils of the Alzheimer's disease Abeta (16-22) peptide probed by molecular dynamics simulations, J. Mol. Biol., 2008, pp. 718-729, vol. 384, No. 3.

Yakovlev et al., Biochemistry, 2000, pp. 15730-15741, vol. 39.

Yan et al., Cellular cofactors potentiating induction of stress and cytotoxicity by amyloid β-peptide, Biochimica et Biophysica Aeta, 2000, pp. 145-157, vol. 1502.

Zucker et al., Abstract, Vascular endothelial growth factor induces tissue factor and matrix metalloproteinase production in endothelial cells: conversion of prothrombin to thrombin results in progelatinase A activation and cell proliferation, Int J. Cancer, Mar. 2, 1998, p. 780-86, vol. 75, No. 5.
Office Action for U.S. Appl. No. 11/033,105 dated May 3, 2007.
Office Action for U.S. Appl. No. 11/033,105 dated Nov. 21, 2007.
Office Action for U.S. Appl. No. 11/033,105 dated Aug. 25, 2008.
Office Action for U.S. Appl. No. 11/033,105 dated May 22, 2009.
Office Action for U.S. Appl. No. 11/033,105 dated Dec. 22, 2009.
Office Action for U.S. Appl. No. 11/384.169 dated Oct. 28, 2008.
Office Action for U.S. Appl. No. 11/384,169 dated Jun. 10, 2009.
Office Action for U.S. Appl. No. 11/087,102 dated Nov. 23, 2007.
Office Action for U.S. Appl. No. 11/087,102 dated Jul. 23, 2009.
Office Action for U.S. Appl. No. 11/087,102 dated Jul. 6, 2010.
Office Action for U.S. Appl. No. 11/181,012 dated Mar. 22, 2007.
Office Action for U.S. Appl. No. 11/181,012 dated Sep. 25, 2007.
Office Action for U.S. Appl. No. 11/181,012 dated May 30, 2008.
Office Action for U.S. Appl. No. 11/181,012 dated Mar. 20, 2009.
Office Action for U.S. Appl. No. 11/181,012 dated Dec. 28, 2009.
Office Action for U.S. Appl. No. 11/995,308 dated Apr. 3, 2009.
Office Action for U.S. Appl. No. 11/995,308 dated Jan. 8, 2010.
Office Action for U.S. Appl. No. 11/995,308 dated Oct. 1, 2010.
Office Action for U.S. Appl. No. 11/661,537 dated Jun. 11, 2009.
Office Action for U.S. Appl. No. 11/661,537 dated Jan. 26, 2010.
Office Action for U.S. Appl. No. 11/181,040 dated May 31, 2007.
Office Action for U.S. Appl. No. 11/181,040 dated Jul. 15, 2008.
Office Action for U.S. Appl. No. 11/181,040 dated Nov. 27, 2007.
Office Action for U.S. Appl. No. 11/181,040 dated Jan. 12, 2009.
Office Action for U.S. Appl. No. 11/181,040 dated Oct. 29, 2009.
Office Action for U.S. Appl. No. 11/181,040 dated Jun. 23, 2010.
Chauhan et al., Media from Rhabdomyosarcoma and Neuroblastoma Cell Cultures Stimulate in Vitro Aggregation and Fibrillization of Amyloid Beta-Protein, Neurochemical Research, 1997, pp. 227-232, vol. 22, No. 2.
Dubois et al., Thrombin binding to GPIbα induces platelet aggregation and fibrin clot retraction supported by resting aIIbβ3 interaction with polymerized fibrin, Thromb Haemost, 2003, pp. 853-864. vol. 89.
Elghetany et al., Methods for Staining Amyloid in Tissues: A Review, Stain Technology, Jan. 1, 1988, pp. 201-211, vol. 63, No. 4.
European Search Report (08 153 132.9) dated Oct. 1, 2009.
European Search Report (EP 1 978 362 A3) dated Oct. 2, 2008.
Gadek, T., Strategies and Methods in the Identification of Antagonists of Protein-Protein Interactions, Structure-Guided Drug Discovery, pp. 21-24.
Hajduk et al., Discovering High-Affinity Ligands for Proteins, Science, Oct. 17, 1997, pp. 497-499, vol. 278.
Hubbard et al., Spontaneous pancreatic islet amyloidosis in 40 baboons, J. Med. Primatol, 2002, pp. 84-90, vol. 31, No. 2.
Klunk et al., Development of Small Molecule Probes for the Beta-Amyloid Protein of Alzheimer's Disease, Neurobiology of Aging, 1994, pp. 691-698. vol. 15, No. 6, Elsevier Science Ltd., USA.
Merlini et al., Interaction of the anthracycline 4'-iodo-4' deoxydoxorubicin with amyloid fibrils: Inhibition of amyloidogenesis, Proc. Natl. Acad. Sci., Mar. 1995, pp. 2959-2963. vol. 92.
Nyhlin et al., Advanced glycation end product in familial amyloidotic polyneuropathy (FAP), Journal of Internal Medicine, 2000, pp. 485-492, vol. 247.
Roth et al., Differential Engagement of Platelet CD36 in Fibrin clot retraction versus aggregation, Blood, Nov. 2003, 45th Annual Meeting of the American Society of Hematology, vol. 102. No. 11, San Diego, CA, USA.
U.S. Appl. No. 12/741,288, filed Aug. 30, 2010, Gebbink et al., Immunogenic Compostions Capable of Activating T-Cells.
U.S. Appl. No. 12/741,270, filed Aug. 26, 2010, Gebbink et al., Enhancement of Immunogenicity of Antigens.
Database WPI; Thomson Scientific, London, GB; AN 1985174924; XP 002631339 & JP 60 103964; Unitika Ltd; Jun. 8, 1985.
European Search Report; EP 10 18 5187 dated Aug. 29, 2011.
Kataoka, et al; Hepatocyte Growth Factor Activator Inhibitor Type 1 Is a Specific Cell Surface Binding Protein of Hepatocyte Growth Factor Activator (HGFA) and Regulates HGFA Activity in the Pericellular Microenvironment; The Journal of Biological Chemistry; vol. 275, No. 51, Dec. 22, 2000; pp. 40453-40462.
Adessi et al., Abstract, Beta-sheet breaker strategy for the treatment of Alzheimer's disease. Drug Development Res 56(2): 184-193, 2002.
Akiyama, et al; Abstract; Inflammation and Alzheimer's disease; Neurobiol Aging. May/Jun. 2000; 21(3); 383-421.
Arora et al., Inhibition of insulin amyloid formation by small stress molecules, FEBS Letters, 2004, pp. 121-125, vol. 564.
Bachmann, et al.; Recall Proliferation Potential of Memory CD8 + Cells and Antiviral Protection; The Journal of Immunology; 2005, 175: 4677-4685.
Baldwin et al., Stable-isotope-labeled peptides in study of protein aggregation, Methods Enzymol., 1999, pp. 576-591, vol. 309.
Blondelle et al., Abstract, Polyalanine-based peptides as models for self-associated beta-pleated-sheet complexes. Biochemistry 36: 8393-8400, 1997.
Bouma et al., Glycation Induces Formation of Amyloid Crossbeta Structure in Albumin, The Journal of Biological Chemistry, Oct. 24, 2003, vol. 278, No. 43, pp. 41810-41819.
Bronsveld et al., "Use of glucose-insulin-potassium (GIK) in human septic shock," Critical Care Medicine, 1985, pp. 566-570, vol. 13, No. 7.
Brownlie et al., Treatment of Murine Collagen-Induced Arthritis by the Stress Protein BiP Via Interleukin-4-Producing Regulatory T Cells, Arthritis & Rheumatism, Mar. 2006, pp. 85463, vol. 54.
Cardoso et al., "Aprotinin binding to amyloid fibris," Eur. J. Biochem 2000, pp. 2307-2311, vol. 267.
Chauhan et al., "Metal Cations Defibrillize the Amyloid BetaProtein Fibrils," Neurochemical Research, 1997, pp. 805-809, vol. 22, No. 7.
Coker, et al.; Moleculr chaperone properties of serum amyloid P component; FEBS Letters 473 (2000) 199202.
Efferson, et al; Stimulation of Human T Cells by an Influenza A Vector Expressing a CTL Epitope from the HER2/neu Protooncogene Results in Higher Numbers of Antigen-specific TCR[hi] Cells than Stimulation with Peptide, Divergent Roles of IL-2 and IL-15; Anitcancer Research 25: 715-724 (2005).
Esler et al., Deposition of soluble amyloid-beta onto amyloid templates: With application for the identification of amyloid fibril extension inhibitors, Methods Enzymol., 1999, pp. 350-374, vol. 309.
Golabek et al., The interaction bdween Apolipoprotein E and Alzheimer's amyloid betapeptide is dependent on beta-peptide conformation. J Biol Chem 271(18): 10602-10606, 1996.
Hetenyi et al., Abstract, Computational studies on the binding of thebeta-sheet breaker (BSB) peptides on amyloid betaA(1-42). J. Molec. Structure, 2001, pp. 25-31, vol. 542.
Hurtley et al., Interactions of Misfolded Influenza Virus Hemagglutinin with Binding Protein (BiP), The Journal of Cell Biology, Jun. 1989 , pp. 2117-2126, vol. 108.
Jackson et al., "Glucose Infusions Increase Plasma Levels of Amyloid Proteins in High Density Lipoproteins," Biomedicine, 1980, pp. 245, vol. 33.
Kim et al., Thermodynamic beta-sheet propensities measured using a zino-finger host peptide, Nature, 1993, pp. 267-270, vol. 362.
Kudva et al., Small heat shock proteins inhibit in vitro $A\beta_{-42}$ amyloidogenesis, FEBS Letters, 1997, pp. 117-121, vol. 416.
Levine III, et al., Screening for pharmacologic inhibitors of amyloid fibril formation, Methods Enzymol., 1999, pp. 46-76, vol. 309.
Maesaki et al., The structural basis of rho effector recognition revealed by the crystal structure of human rhoA complexed with the effector domain of PKN/PRK1, Mol. Cell., 1999, pp. 793-803, vol. 4.
Maggio et al., "Brain Amyloid-A Physicochemical Perspective," Brain Pathology, 1996, pp. 147-162, vol. 6.
Minor et al., Context is a major determinant of betasheet propensity, Nature, 1994, pp. 264-267, vol. 371.
Ono, et al.; Radioiodinated Flavones for in Vivo Imaging of $\beta$-Amyloid Plaques in the Brain; J. Med. Chem. 2005, 48, 7253-7260.
Partial European Search Report, EP 02 07 7797, dated Dec. 13, 2002.
PCT International Search Report, PCT/NL2003/000501, dated Mar. 31, 2004.

Pepys, M. B., "Pathogenesis, diagnosis and treatment of systemic amyloidosis," Philosophical Transactions of the Royal Society of London B Biological, 2001, pp. 203-211, vol. 356, No. 1406.

Permanne et al., Reduction of amyloid load and cerebral damage it a transgenic mouse model of Alzheimer's disease by treatment with a beta-sheet breaker peptide. Faseb J. 16(8):860-862, 2002.

Reinbold, J., "Akuttherapie der diabetischen Notfalle," Notfallmedizin, 2002, pp. 8284, vol. 28.

Reixach et al., Inhibition of beta-amyloid-induced neurotoxicity by imidazopyridoindoles derived from a synthetic combinatorial library, J. Struct. Biol. 2000, pp. 247-258, vol. 130.

Sigurdsson et al., Abstract, In vivo reversal of amyloid-beta lesions in the rat brain. J Neruopath Exp Neurol 59(1): 11-17, 2000.

Slavotinek et al., Unfolding the role of chaperones and chaperonins in human disease, Trends in Genetics, Sep. 2001, pp. 528-535, vol. 17, No. 9.

Soto C et al., Abstract, Inhibition of Alzheimer's amyloidosis by peptides that prevent betasheet conformation. Biochem Biophys Res Commun. 226(3):672-680, 1996.

Soto C et al,, Beta-sheet breaker peptides inhibit fibrillogenesis in a rat brain model of amyloidosis: implications for Alzheimer's therapy. Nat Med. 4(7):822-826, 1998.

Soto C., Abstract, Alzheimer's and prion disease as disorders of protein conformation: implications for the design of novel therapeutic approaches. J Mol Med. 77(5):412-418, 1999.

Soto C., Abstract, Beta-amyloid disrupting drugs. CNS Drugs 12(5): 347-356, 1999.

Soto C., Abstract, Plaque busters: strategies to inhibit amyloid formation in Alzheimer's disease. Mol Med Today. 5(8):343-350, 1999.

Testa et al, "The Effect of Different Glucose Endovenous Administrations on Amyli and Insulin Blood Concentration in Healthy Subjects," J. Biol. Res.—Boll. Soc. It. Biol. Sper., 1996, pp. 103-108, vol. 72, No. 3-4.

Walsh et al., Amyloid beta-protein fibrillogenesis, J. Biol. Chem., 1999, pp. 2594-2552, vol. 274.

Wasterlain et al., "Status Epilepticus in Immature Rats," Arch Neurol, Dec. 1976, pp. 821-827, vol. 33.

Wheeler, C.M.; Abstract; Preventive vaccines for cervical cancer; Salud p'ublica de M'exico, (Jul./Aug. 1997).

Wood et al Abstract, Prolines and amyloidogenicity in fragments of the Alzheimer's peptide beta/A4. Biochemistry 34: 724 730, 1995.

Yan et al., Receptor-dependent cell stress and amyloid accumulation in systemic amyloidosis, Nature Medicine, Jun. 2000, pp. 643-651, vol. 6, No. 6.

Yutani et al., "The Process of Amyloid-like Fibril Formation by Methionine Aminopeptidase from a Hyperthemophile, *Pyrococcus furiosus*," Biochemistry, 2000, pp. 2769-2777, vol. 39.

Zhang et al., The anatomy of protein beta-sheet topology, J. Mol. Biol., 2000, pp. 1075-1089, vol. 299.

Office Action for U.S. Appl. No. 11/982,161 dated May 28, 2010.

U.S. Appl. No. 11/033,105, filed Jan. 10, 2005, Gebbink, et al., Cross-β Structure Comprising Amyloid-Binding Proteins and Methods for Detection of the Crossβ Structure, for Modulating Cross-β Structures Fiber.

U.S. Appl. No. 11/886,867, filed Dec. 11, 2007, Gebbink, et al., Cross β Structure Comprising Amyloid-Binding Proteins and Methods for Detection of the Cross β Structure, for Modulating Cross β Structures Fibril.

U.S. Appl. No. 11/087,102, filed Mar. 21, 2005, Gebbink, et al., Cross β Structure Comprising Amyloid-Binding Proteins and Methods for Detection of the Cross β Structure, for Modulating Cross β Structures Fibril.

U.S. Appl. No. 11/995,308, filed Mar. 24, 2008, Gebbink, et al., A Method for Detecting and/or Removing a Protein Comprising a CrossB Structure from a Pharmaceutical Composition.

U.S. Appl. No. 11/181,040, filed Jul. 13, 2005, Gebbink, et al., A Method for Detecting and/or Removing Protein Comprising a CrossBeta Structures from a Pharmaceutical Composition.

U.S. Appl. No. 11/661,537, filed Apr. 24, 2007, Gebbink, et al., Adjuvation Through Cross-β Structures.

U.S. Appl. No. 11/995,497, Mar. 19, 2008, Gebbink, et al., Cross-Beta Structure Binding Compounds.

U.S. Appl. No. 12/224,087, filed Feb. 18, 2009, Gebbink, et al., Affinity Regions.

U.S. Appl. No. 12/225,291, filed Jan. 7, 2009, Gebbink, et al., Methods of Binding of Cross-Beta Structures by Chaperones.

U.S. Appl. No. 12/800,700, filed May 19, 2010, Bouma et al., Modulating Compounds.

U.S. Appl. No. 12/998,691, filed May 18, 2011, Bouma, et al., Cross-Beta Structures as Carriers in Vaccines.

European Search Report for Application No. 11153594.4.1223 dated Jun. 8, 2011.

Kisilevsky, et al. Characterization of Fibronectin Binding to Alzheimer's Beta Amyloid Precursor Proteins, Third International Conference on Alzheimer's Disease; S81-S82.

Yasuhara, et al. Hageman factor and its binding sites are present in senile plaques of Alzheimer's disease, Brian Research 654 (1994) 234-240.

Hinson et al., Pathogenic potential of IgG binding to water channel extracellular domain in neuromyelitis optica, Neurology, vol. 69, No. 24, pp. 2221-2231; 2007.

Johnstone et al., Monoclonal antibodies that recognize the native human thyrotropin receptor, Mol. Cell, Endocrinol., vol. 105, No. 2, pp. R1-R9; 1994.

Kisilevsky, et al. Characterization of Fibrorectin Binding to Alzheimer's Beta Amyloid Precursor Proteins, Third International Conference on Alzheimer's Disease; S81-S82; Jul. 12-17, 1992.

* cited by examiner

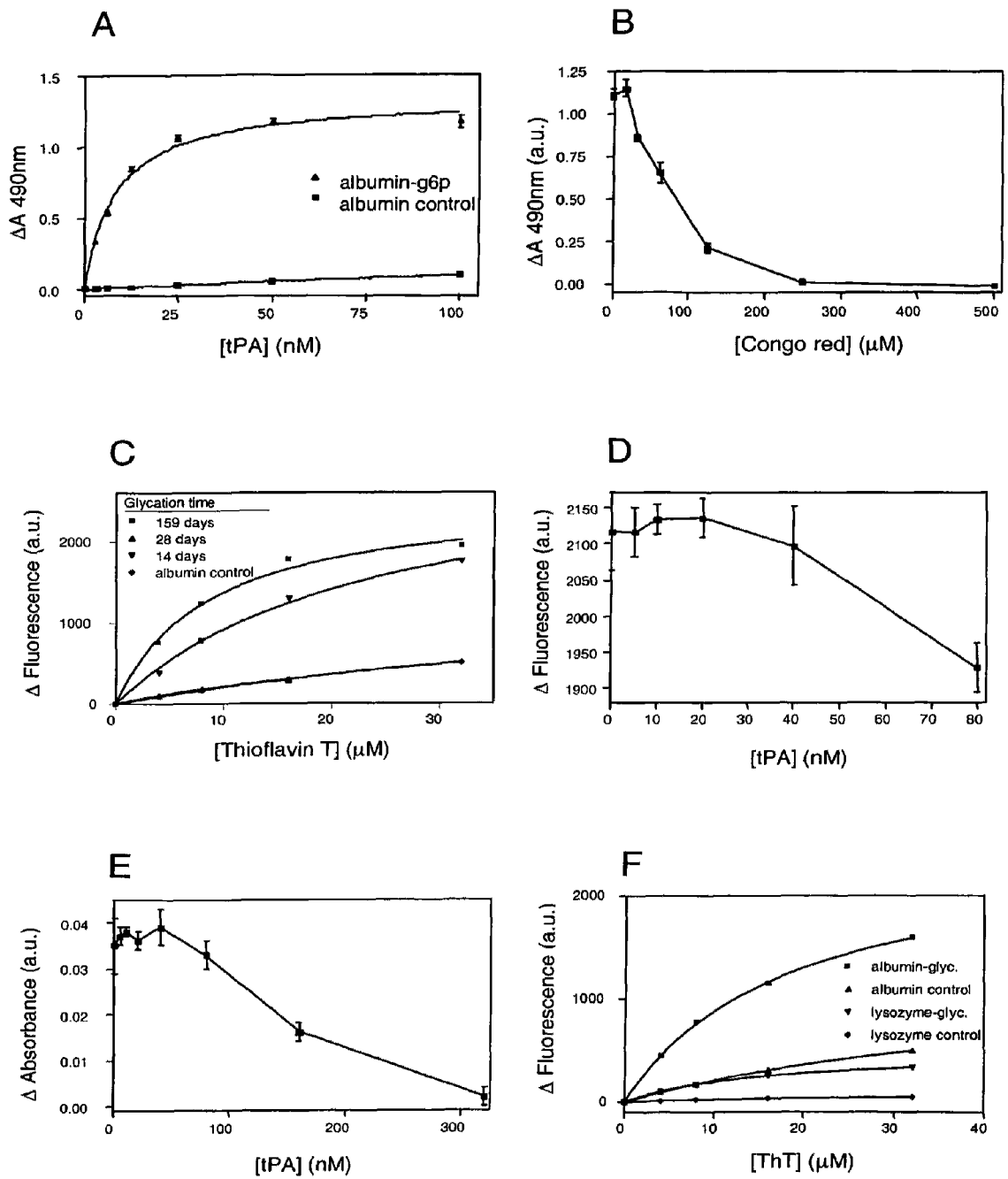
FIG. 8 (page 1)

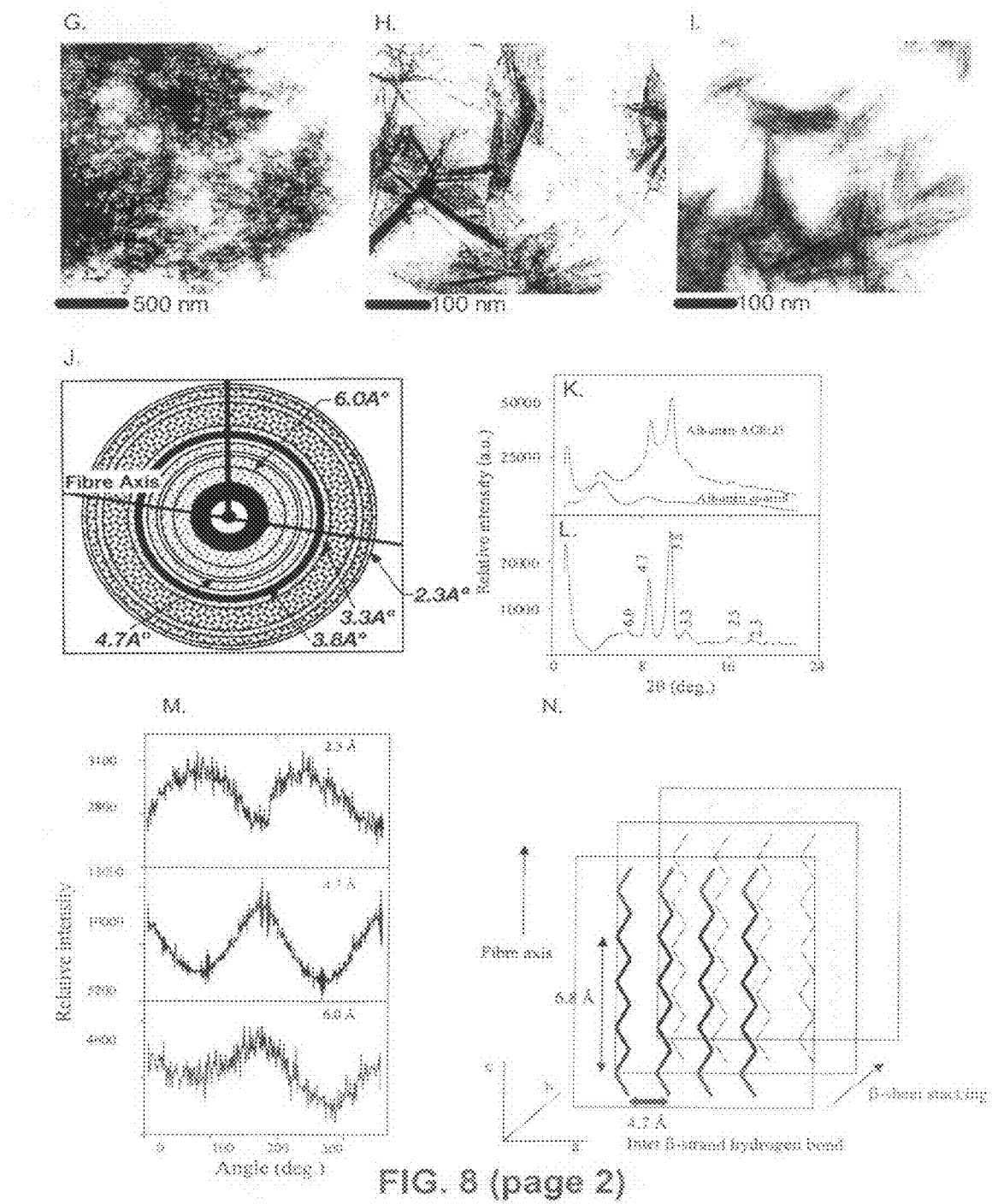
FIG. 8 (page 2)

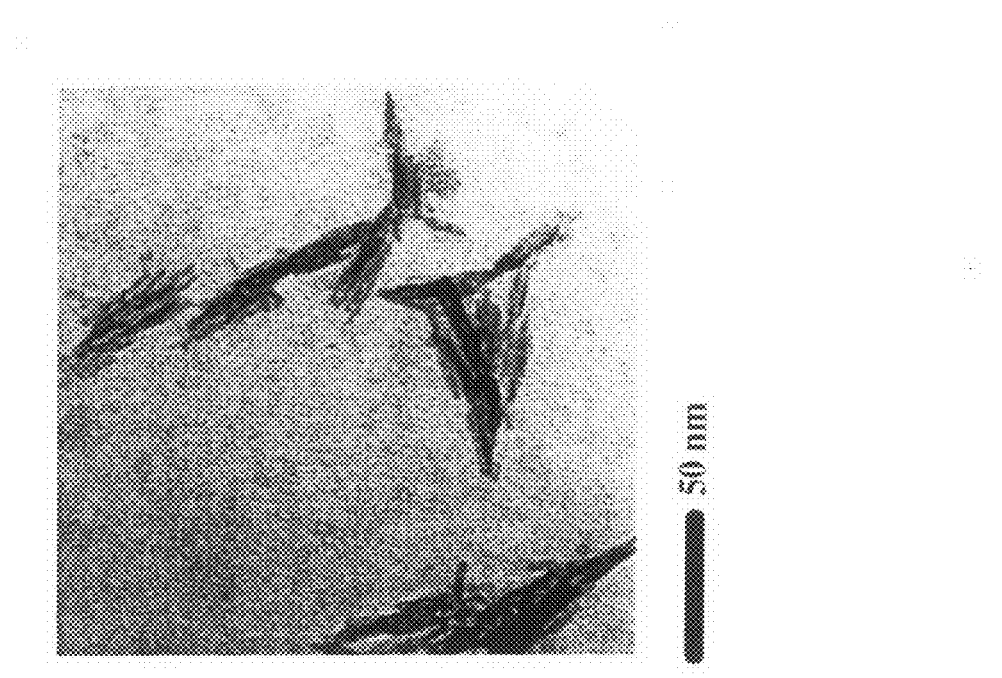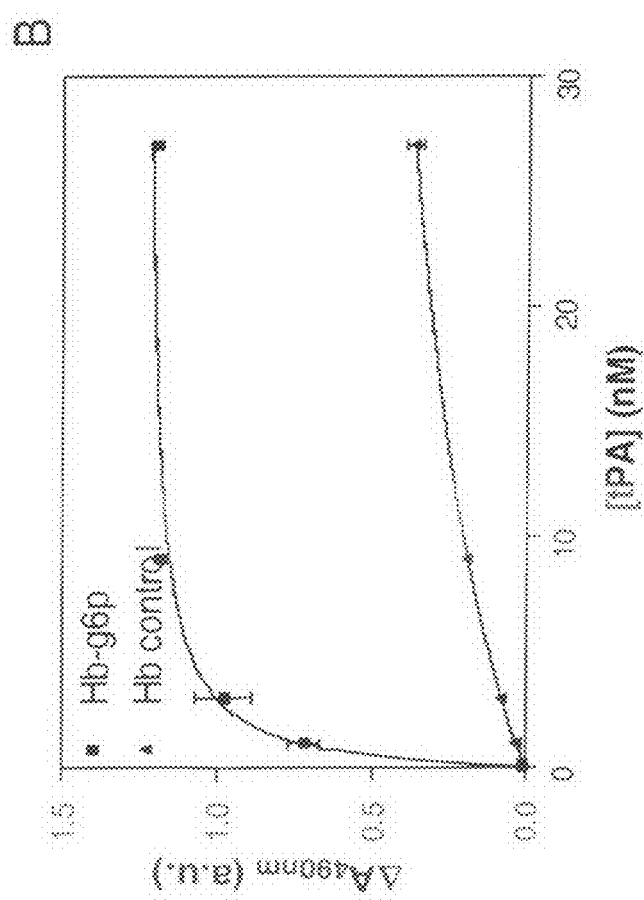
FIG. 9

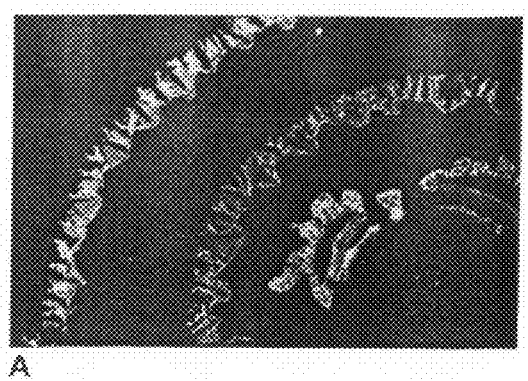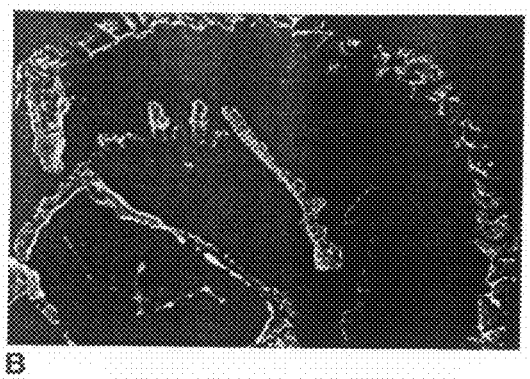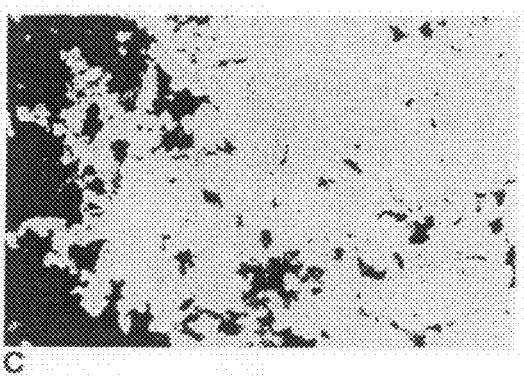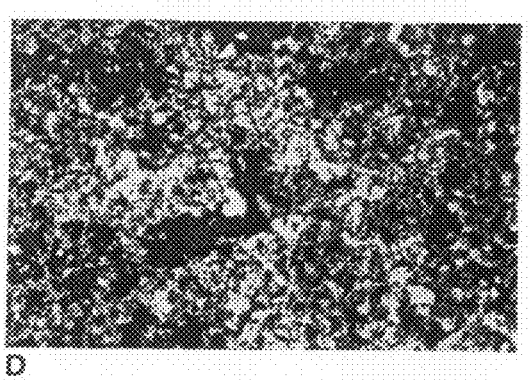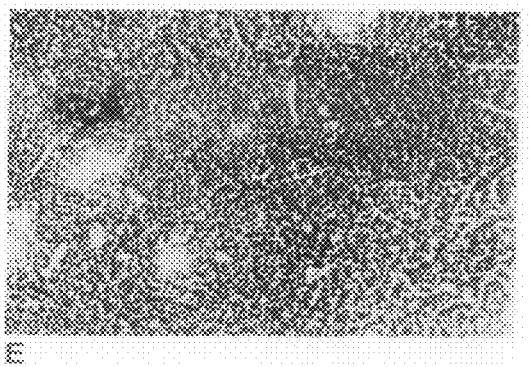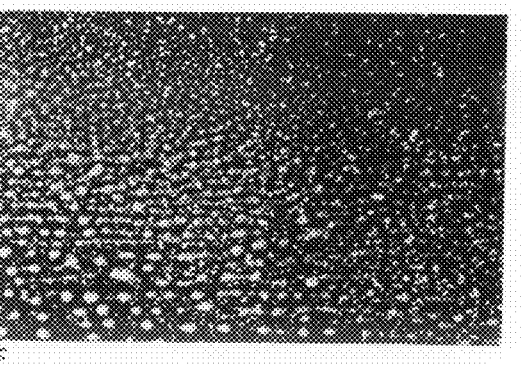
FIG. 10 (page 1)

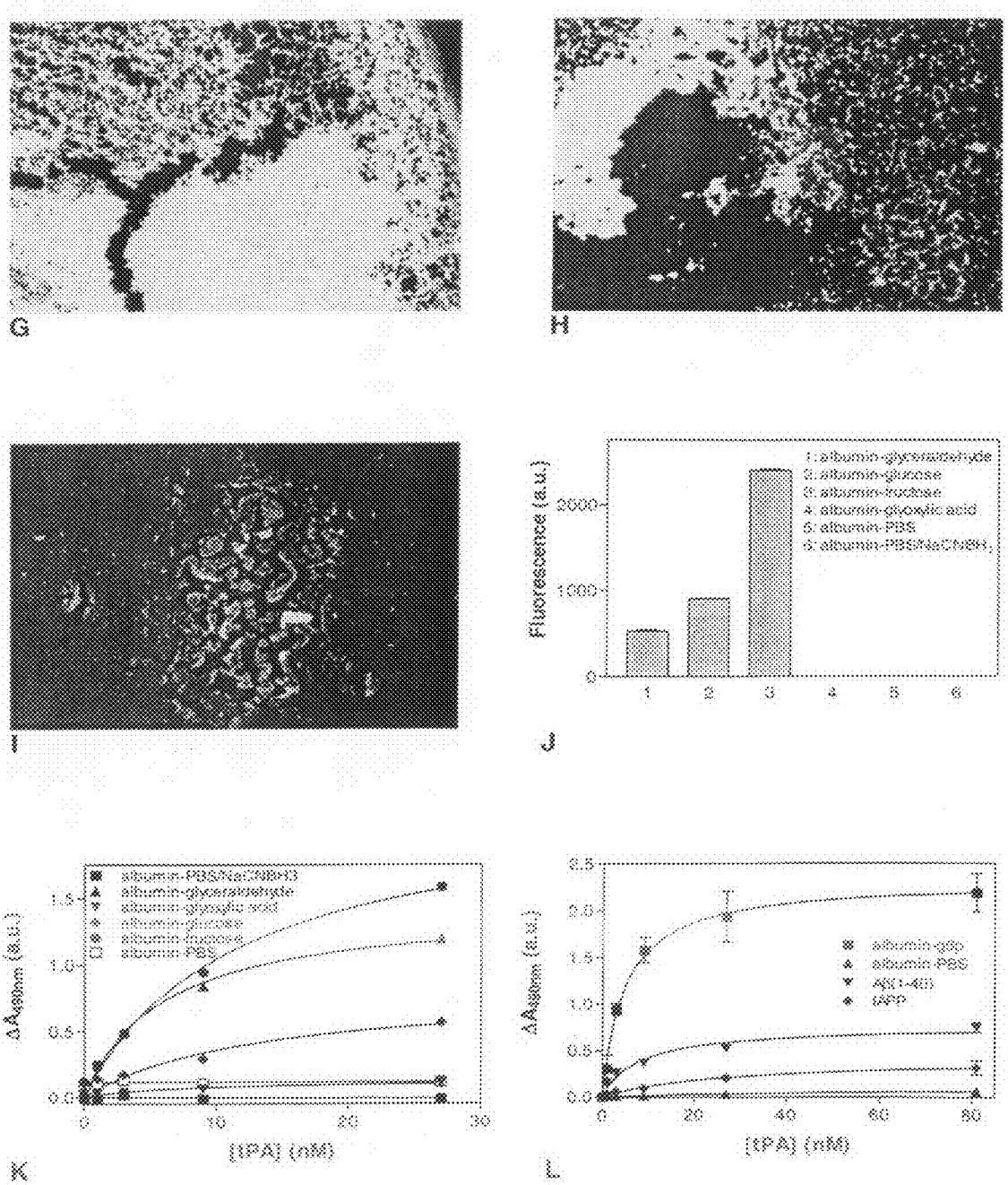
FIG. 10 (page 2)

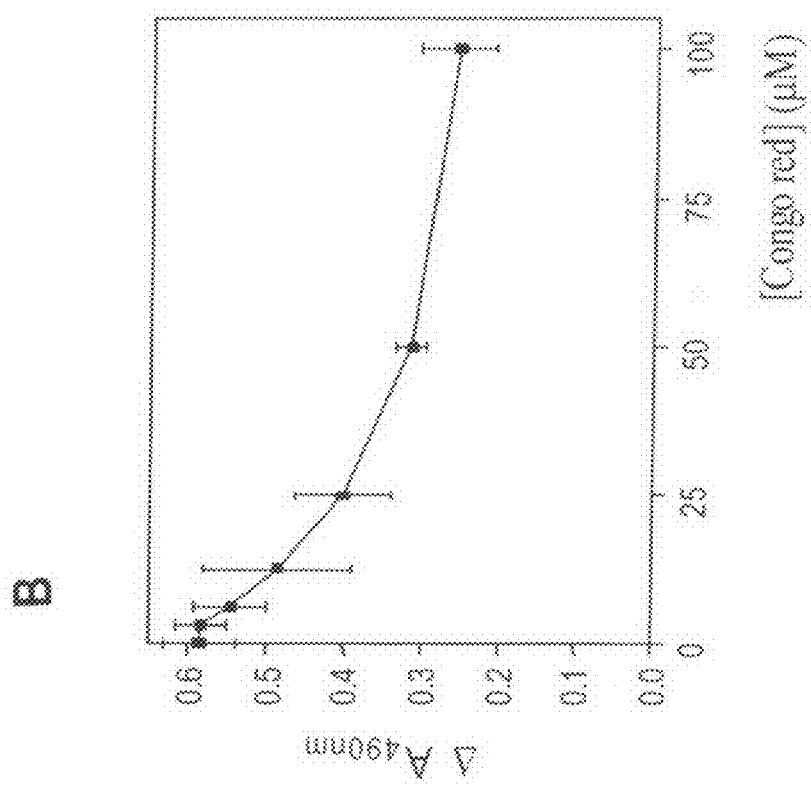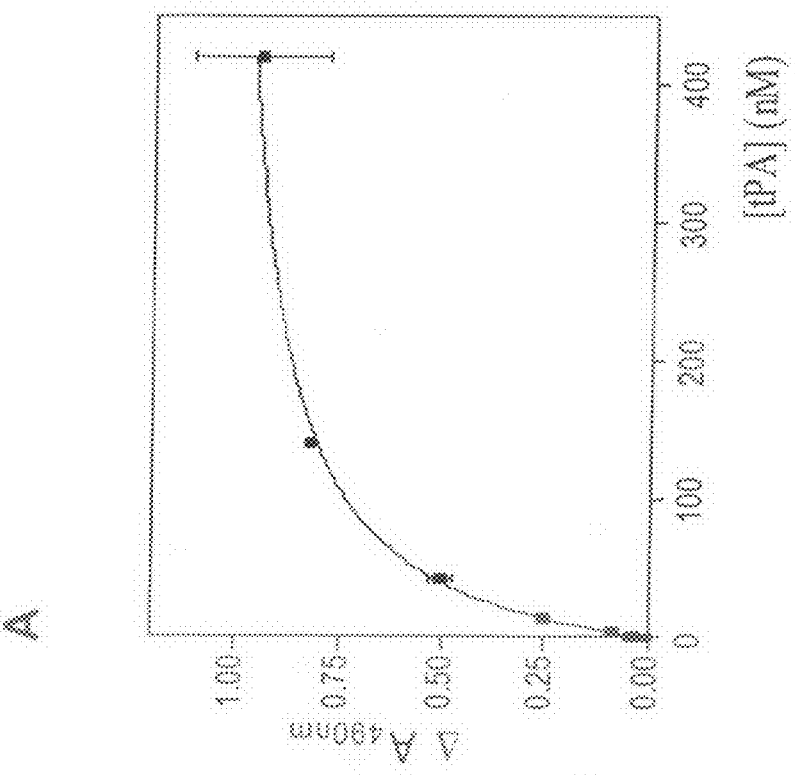
FIG. 11

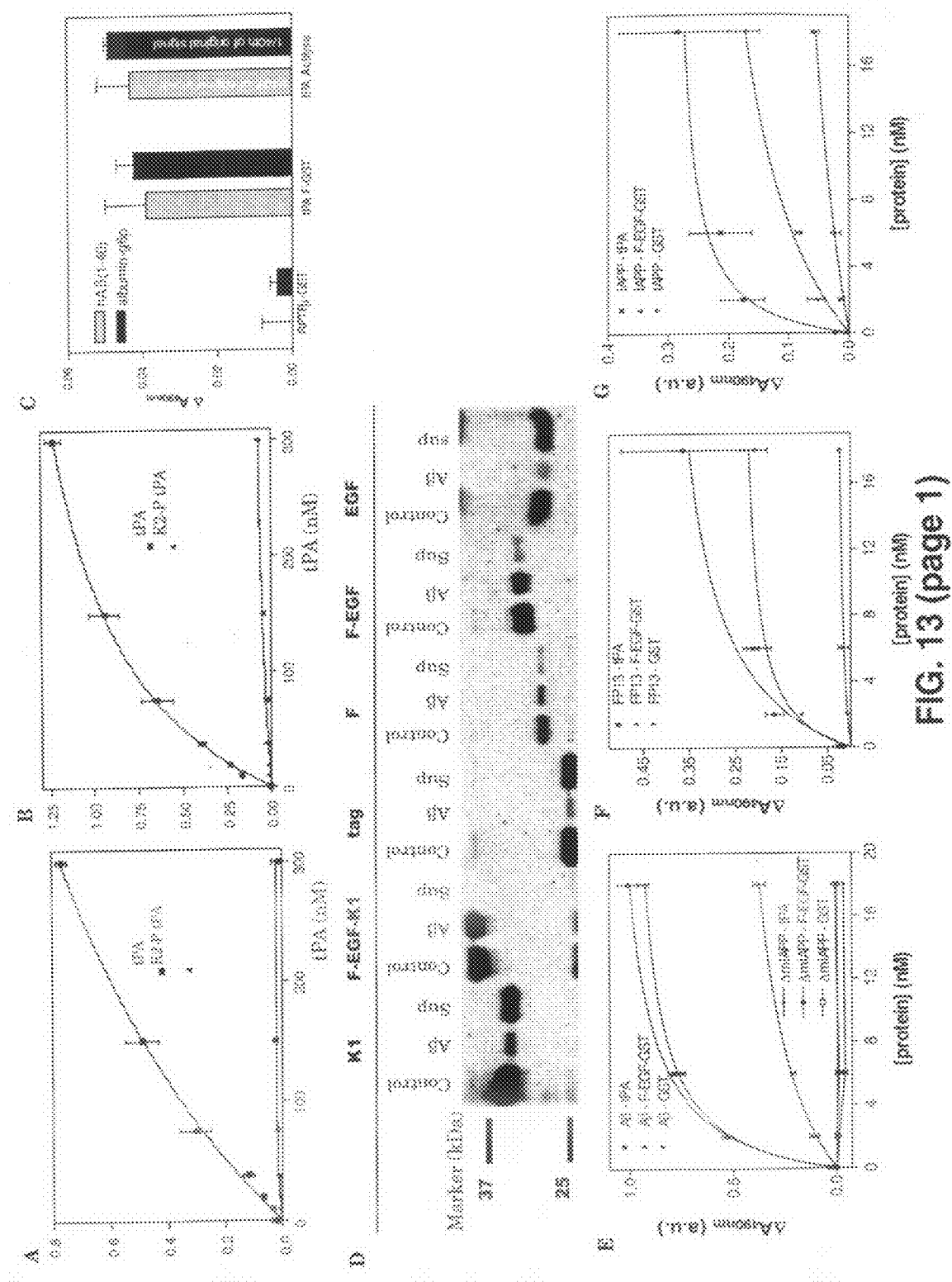
FIG. 13 (page 1)

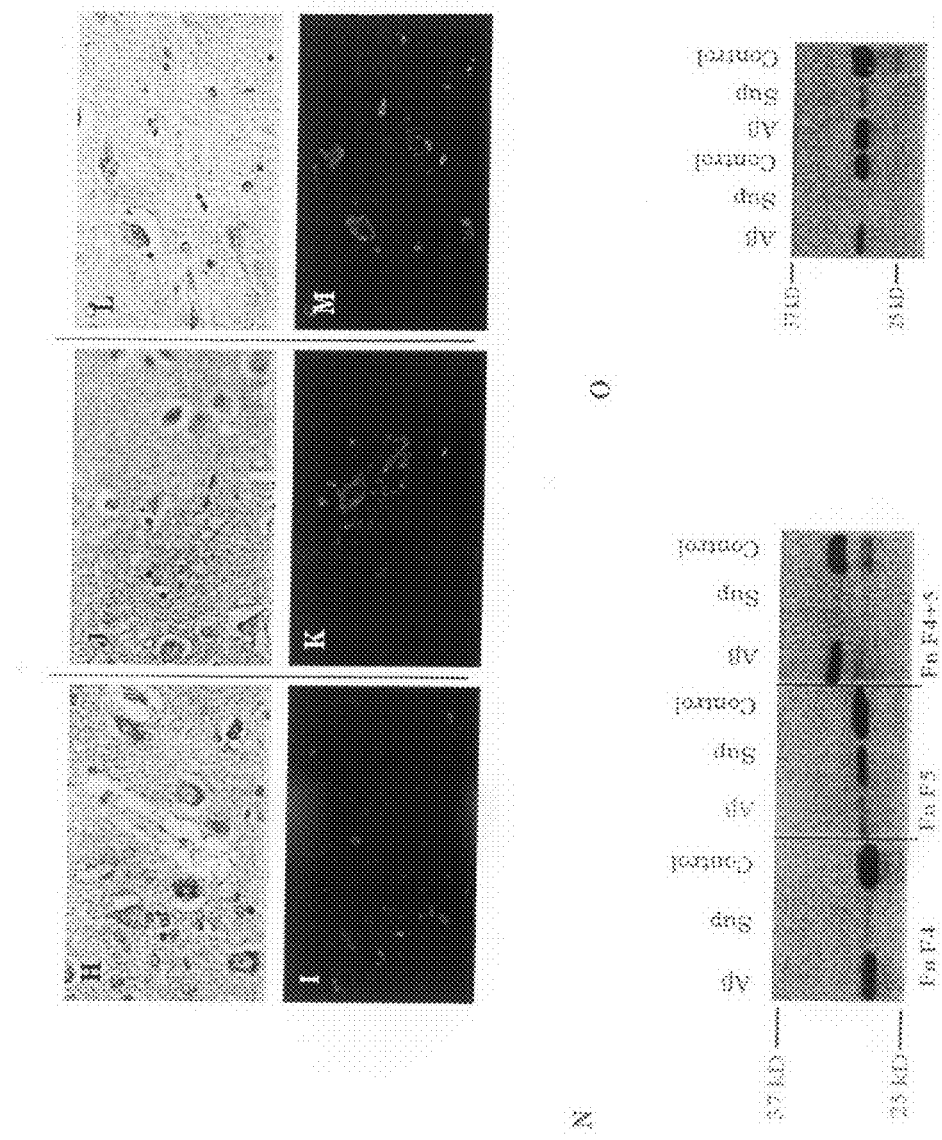
FIG. 13 (page 2)

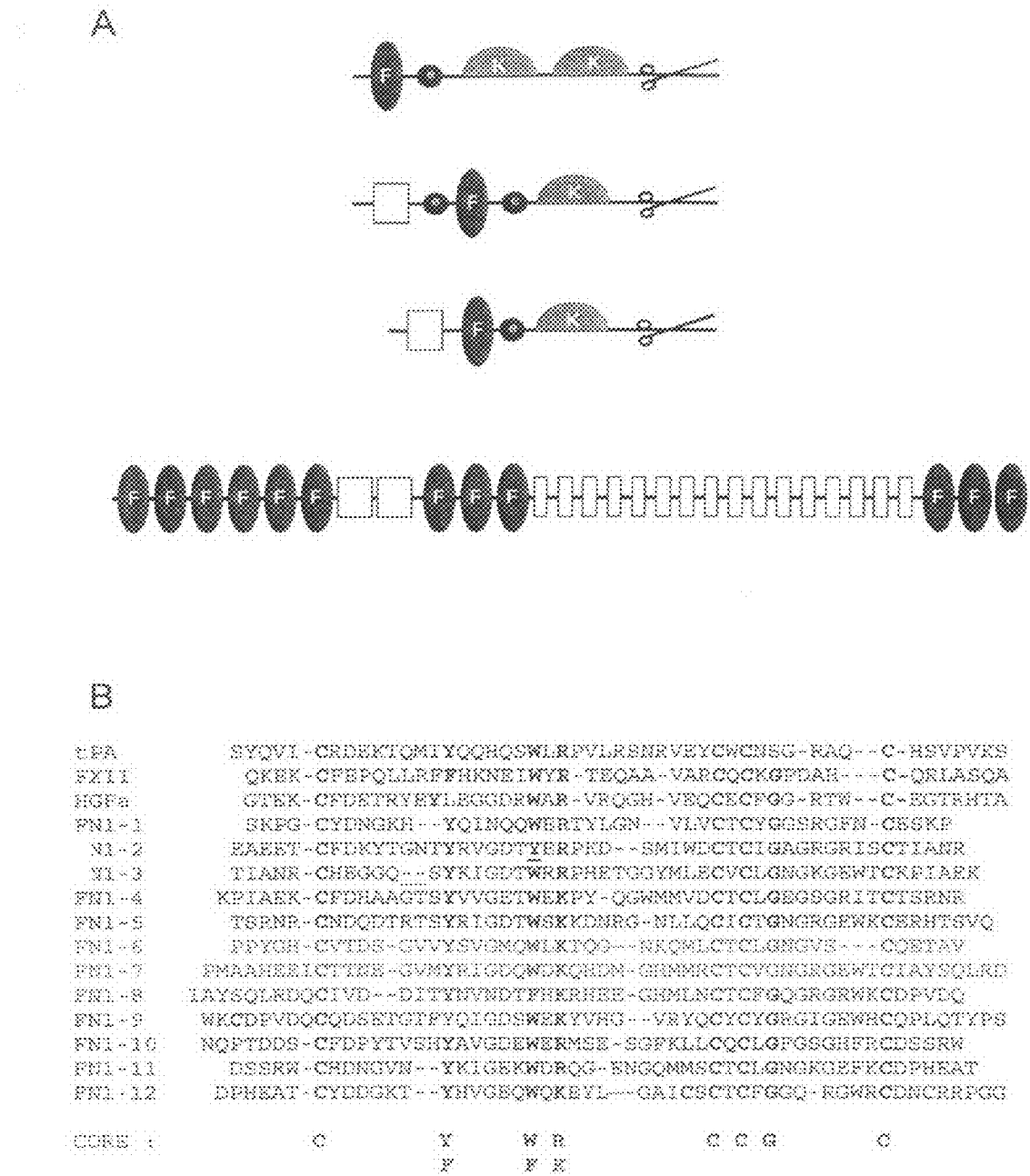
FIG. 14 (page 1)

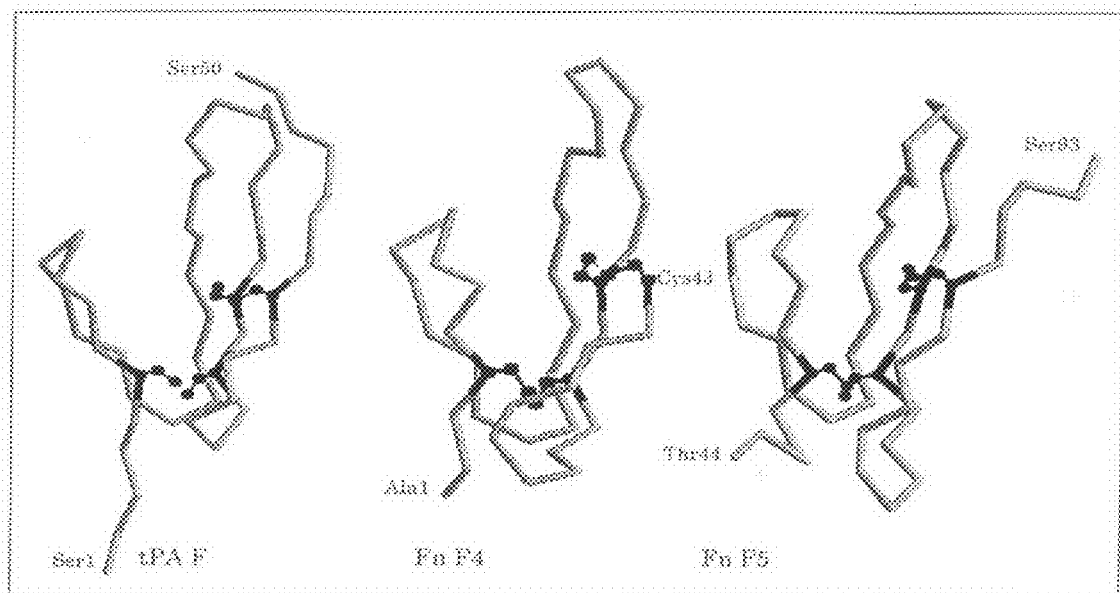
FIG. 14 (page 2)

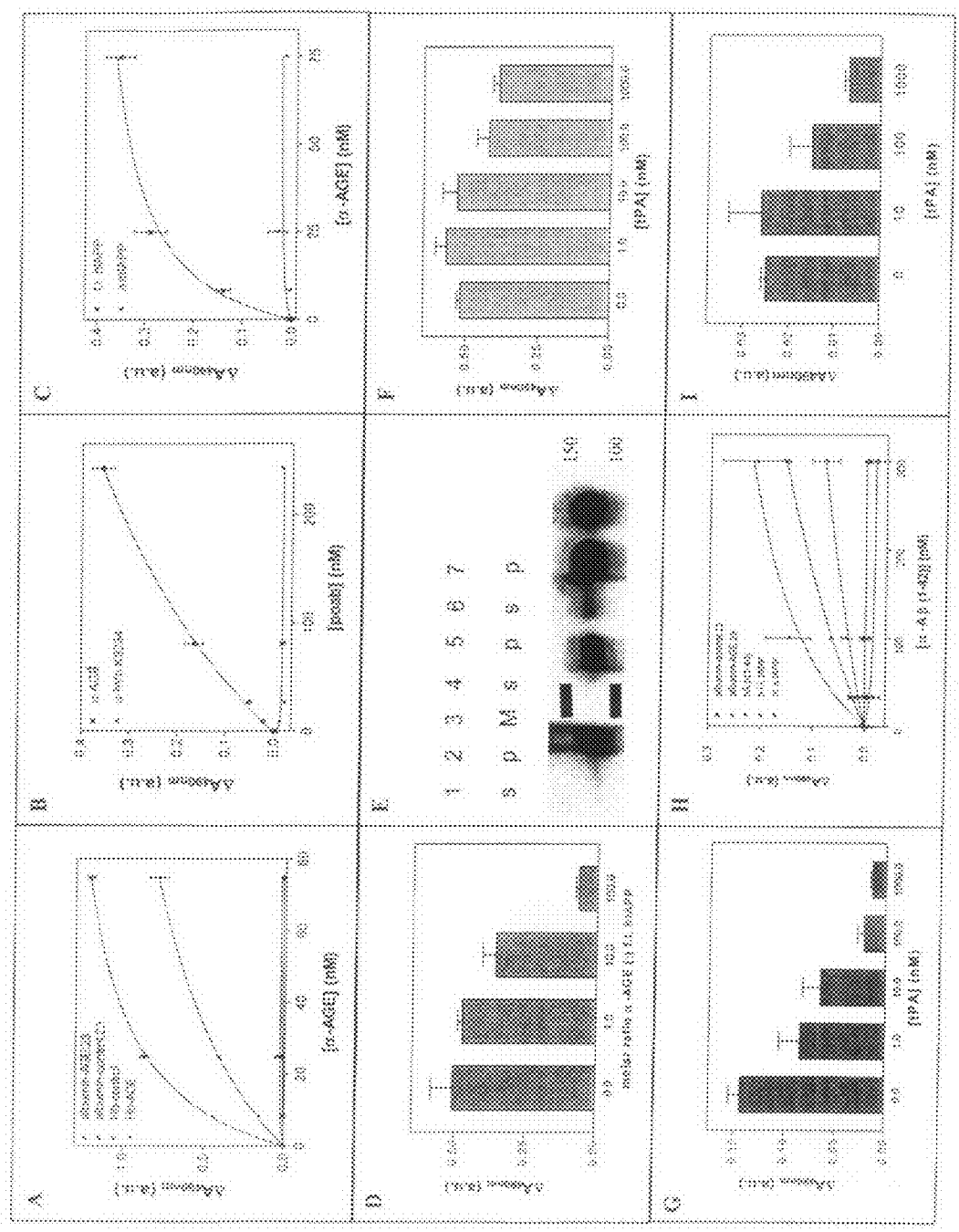
FIG. 15 (page 1)

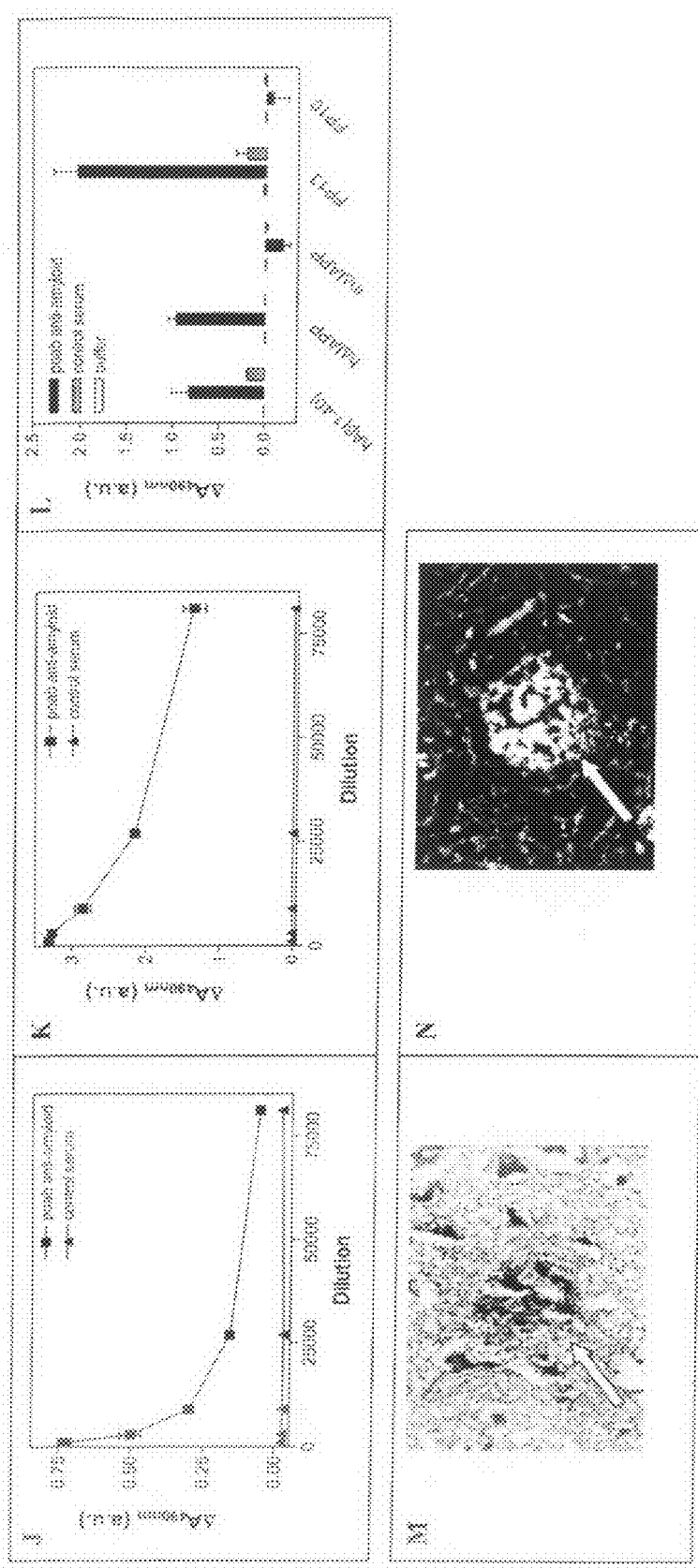
FIG. 15 (page 2)

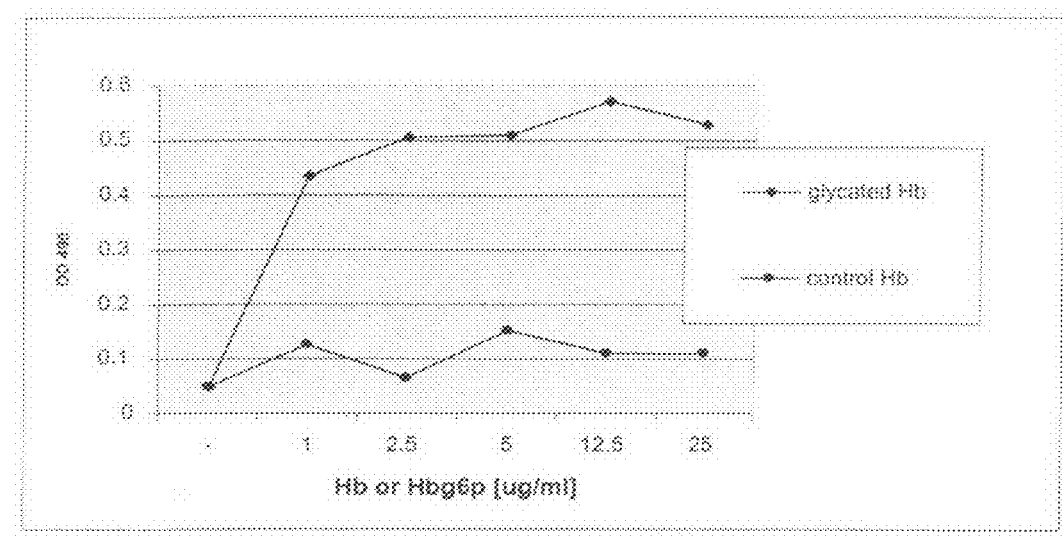
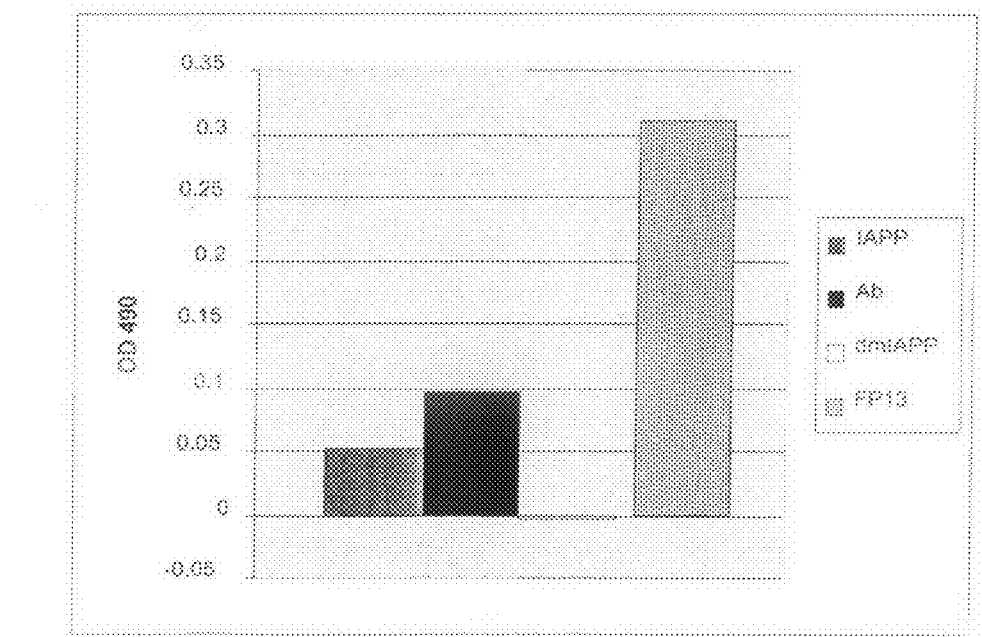
FIG. 16

CROSS-β STRUCTURE COMPRISING AMYLOID-BINDING PROTEINS AND METHODS FOR DETECTION OF THE CROSS-β STRUCTURE, FOR MODULATING CROSS-β STRUCTURES FIBER FORMATION AND MODULATING CROSS-β STRUCTURE-MEDIATED TOXICITY

CROSS-REFERENCE TO RELATED APPLICATIONS

This application is a divisional of application Ser. No. 11/033,105, filed Jan. 10, 2005, pending, which is a continuation of PCT International Patent Application PCT/NL2003/000501, filed Jul. 8, 2003, designating the United States of America, corresponding to PCT International Publication WO 2004/004698 A3 (published in English on Jan. 15, 2004). The disclosure of each of the previously referenced patent applications referenced is hereby incorporated by reference in its entirety.

STATEMENT ACCORDING TO 37 C.F.R. §1.52(e)(5)

Sequence Listing Submitted on Compact Disc

Pursuant to 37 C.F.R. §1.52(e)(1)(iii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "sequence listing.txt" which is 16 KB and created on Sep. 4, 2007.

TECHNICAL FIELD

The invention relates to the fields of biotechnology, biochemistry, molecular biology, structural biology and medicine. More in particular, the invention relates to cross-β structure, their binding proteins and their biological roles.

BACKGROUND

An increasing body of evidence suggests that unfolding of globular proteins can lead to toxicity.[1] Unfolded proteins can initiate protein aggregation and fibrillization by adopting a partially structured conformation. Such fibrillar aggregates can (slowly) accumulate in various tissue types and are associated with a variety of degenerative diseases. The term "amyloid" is used to describe these fibrillar deposits (or plaques). Diseases characterized by amyloids are referred to as amyloidosis and include Alzheimer disease (AD), light-chain amyloidosis, type II diabetes and spongiform encephalopathies. It has been found recently that toxicity is an inherent property of misfolded proteins. According to the present invention, this is the common mechanism for these conformational diseases.[1]

A cross-β structure is a secondary structural element in peptides or proteins. A cross-β structure can be formed upon denaturation, proteolysis or unfolding of proteins.[2] These secondary structure elements are typically absent in globular regions of proteins. The cross-β structure is found in amyloid fibers. Amyloid peptides or proteins are cytotoxic to cells. A cross-β structure includes stacked β-sheets. In a cross-β structure, the individual β-strands either run perpendicular to the long axis of a fibril or run in parallel to the long axis of a fibril. The direction of the stacking of the β-sheets in cross-β structures is perpendicular to the long fibril axis.

SUMMARY OF THE INVENTION

It is reported herein that glycation of proteins also induces the formation of the cross-β structure. These results, combined with existing literature information, indicate that a common structure is induced upon unfolding of globular proteins. Therefore, the present invention discloses a novel pathway involving a cross-β structure, which pathway will be called a "cross-β structure pathway." This pathway includes several cross-β structure-binding proteins, including so-called multiligand receptors, and is involved in degradation and/or clearance of unwanted or destroyed (denatured) proteins. Also reported herein is the identification of novel cross-β-binding proteins that contain a cross-β structure-binding module. These findings support the identification of a cross-β structure pathway. Multiple aspects of this novel pathway are outlined below.

In one embodiment, the present invention discloses that proteolyzed, denatured, unfolded, glycated, oxidized, acetylated or otherwise structurally altered proteins adopt cross-β structures. Examples of known cross-β structure-forming proteins are all proteins that cause amyloidosis or proteins that are found in disease-related amyloid depositions, for example, but not restricted to, Alzheimer β-amyloid (Aβ) and Islet Amyloid PolyPeptide (IAPP). The present invention discloses that fibrin, glycated proteins (for example, glycated albumin and glycated hemoglobin), and endostatin are also capable of adopting a cross-β structure.

The invention furthermore discloses the identification of the formation of a cross-β structure as a signal for protein degradation and/or protein clearance.

The serine protease tissue plasminogen activator (tPA) induces the formation of plasmin through cleavage of plasminogen. Plasmin cleaves fibrin and this occurs during lysis of a blood clot. Although not essential for fibrinolysis in mice,[3,4] tPA has been recognized for its role in fibrinolysis for a long time.[5,6] Activation of plasminogen by tPA is stimulated by fibrin or fibrin fragments, but not by its precursor, fibrinogen.[7-10] This can be in part explained by the strong binding of tPA to fibrin and weak binding to fibrinogen. The binding sites in fibrin and in tPA responsible for binding and activation of tPA have been mapped and studied in detail.[8-21] However, the exact structural basis for the interaction of tPA with fibrin was unknown. In addition to fibrin and fibrin fragments, many other proteins have been described that are similarly capable of binding tPA and stimulating tPA-mediated plasmin formation.[22-36] Like with fibrin and fibrin fragments, the exact nature of the interaction(s) between these ligands for tPA and tPA were not known. Moreover, it was unknown why and how all of these proteins, which lack primary sequence homology, bind tPA. The present invention discloses tissue-type plasminogen activator (tPA) as a protein capable of binding cross-β structures. Furthermore, the invention discloses the finger domain (also named fibronectin type I domain) and other comparable finger domains as a cross-β structure-binding module. The present invention further discloses that proteins which bind to these fingers will be typically capable of forming cross-β structures.

Since fibrin contains the cross-β structure, the present invention also discloses that the generation of cross-β structures plays a role in physiological processes. The invention discloses that the generation of cross-β structures is part of a signaling pathway, the "cross-β structure pathway," that regulates protein degradation and/or protein clearance. Inadequate function of this pathway may result in the development of diseases, such as conformational diseases[37] and/or amyloidosis.

The present invention furthermore discloses that the cross-β structure is a common denominator in ligands for multiligand receptors.[38] The invention discloses, therefore, that multiligand receptors belong to the "cross-β structure pathway."

The best studied example of a receptor for a cross-β structure is RAGE.[39-44] Examples of ligands for RAGE are Aβ, protein-advanced glycation end-products (AGE) adducts (including glycated-BSA), amphoterin and S100. RAGE is a member of a larger family of multiligand receptors[38] that includes several other receptors, some of which, including CD36, are known to bind cross-β structure-containing proteins (see also FIG. 1). At present, it is not clear what the exact nature of the structure or structures is in the ligands of these receptors that mediates the binding to these receptors. It is reported herein that glycation of proteins also induces the formation of a cross-β structure. Therefore, it is disclosed that all of these receptors form part of a mechanism to deal with the destruction and removal of unwanted or even damaging proteins or agents. These receptors play a role in recognition of infectious agents or cells, recognition of apoptotic cells and in internalization of protein complexes and/or pathogens. It is furthermore disclosed that all of these receptors recognize the same or similar structure, the cross-β structure, to respond to undesired molecules. It is shown herein that tPA binds cross-β structures, providing evidence that tPA belongs to the multiligand receptor family. As disclosed herein, tPA and the other multiligand receptors bind the cross-β structure and participate in the destruction of unwanted biomolecules. A prominent role of the protease tPA in the pathway lies in its ability to initiate a proteolytic cascade that includes the formation of plasmin. Proteolysis is likely to be essential for the degradation and subsequent removal of extracellular matrix components. The effect of tPA on the extracellular matrix will affect cell adhesion, cell migration, cell survival and cell death, through, for example, integrin-mediated processes. Based on these studies, strong evidence is provided that at least three other proteins, FXII (factor XII), hepatocyte growth factor activator (HGFa), and fibronectin, that contain one or more finger domain(s) are also part of the "cross-β structure pathway."

The role of FXII is especially important, since it activates the intrinsic coagulation pathway. Activation of the intrinsic pathway, the resulting formation of vasoactive peptides, and the activation of other important proteins contribute to the process of protection and/or clearance of undesired proteins or agents. The "cross-β structure pathway" is modulated in many ways. Factors that regulate the pathway include modulators of synthesis and secretion, as well as modulators of activity. The pathway is involved in many physiological and pathological processes. Therefore, the invention furthermore provides a method for modulating extracellular protein degradation and/or protein clearance comprising modulating the activity of a receptor for cross-β structure-forming proteins. Examples of receptors for cross-β structure-forming proteins include RAGE, CD36, Low density lipoprotein-Related Protein (LRP), Scavenger Receptor B-1 (SR-B1), and SR-A. The invention discloses that FXII, HGFa and fibronectin are also receptors for cross-β structures.

The present invention discloses that tissue-type plasminogen activator (tPA) is a cross-β structure-binding protein, a multiligand receptor and a member of the "cross-β structure pathway." The invention discloses that tPA mediates cross-β structure-induced cell dysfunction and/or cell toxicity. The invention discloses that tPA mediates, at least in part, cell dysfunction and/or toxicity through activation of plasminogen. The plasminogen-dependent effects are inhibited by B-type carboxypeptidase activity B and, thus, a role for carboxyterminal lysine residues in the cross-β structure pathway is disclosed.

The present invention relates, amongst others, to the structure(s) in fibrin and other proteins that bind tPA, to the binding domain in tPA, and to the pathway(s) regulated by this structure. The present invention discloses a presence of cross-β structures in proteins and peptides that are capable of binding tPA. The herein-disclosed results indicate a strong correlation between the presence of a cross-β structure and the ability of a molecule to bind tPA. Furthermore, the results indicate the presence of an amyloid structure in fibrin. This indicates that under physiological conditions, a cross-β structure can form, a phenomenon that has been previously unrecognized. The formation of cross-β structures has thus far only been associated with severe pathological disorders. tPA binds denatured proteins, which indicates that a large number of proteins, if not all proteins, can adopt a conformation containing cross-β structures or cross-β-like structure(s). Taken together, the formation of cross-β structures is likely to initiate and/or participate in a physiological cascade of events necessary to adequately deal with removal of unwanted molecules, i.e., misfolded proteins, apoptotic cells or even pathogens. FIG. 1 shows a schematic representation of the "cross-β structure pathway." This pathway regulates the removal of unwanted biomolecules during several processes, including fibrinolysis, formation of neuronal synaptic networks, clearance of used, unwanted and/or destroyed (denatured) proteins, induction of apoptosis and clearance of apoptotic cells and pathogens. If insufficiently or incorrectly regulated or disbalanced, the pathway may lead to severe disease.

Thus, in a first embodiment, the invention discloses a method for modulating extracellular protein degradation and/or protein clearance comprising modulating cross-β(beta) structure formation (and/or cross-β structure-mediated activity) of the protein present in the circulation.

There are two major regular protein-folding patterns, which are known as the β(beta)-sheet and the a-helix. An antiparallel β-sheet is formed when an extended polypeptide chain folds back and forth upon itself; with each section of the chains running in the direction opposite to that of its immediate neighbors. This gives a structure held together by hydrogen bonds that connect the peptide bonds in neighboring chains. Regions of a polypeptide chain that run in the same direction form a parallel β-sheet. A cross-β structure is composed of stacked β-sheets. As disclosed herein, a broad range of proteins is capable of adopting a cross-β structure and, moreover, these cross-β structure-comprising proteins are all capable of binding and stimulating tPA, thus promoting destruction of unwanted or damaging proteins or agents.

An extracellular protein is typically defined as a protein present outside a cell or cells.

Protein degradation and/or protein clearance includes the breakdown and removal of unwanted proteins, for example, unwanted and/or destroyed (for example, denatured) proteins. Also included is the removal of unwanted biomolecules during several processes, including fibrinolysis, formation of neuronal synaptic networks, clearance of used, unwanted and/or destroyed (denatured) proteins, induction of apoptosis and clearance of apoptotic cells and pathogens.

The term "in the circulation" is herein defined as a circulation outside a cell or cells, for example, but not restricted to, the continuous movement of blood.

In yet another embodiment, the invention discloses a method for increasing extracellular protein degradation and/or protein clearance comprising increasing cross-β structure formation and/or cross-β structure-mediated activity of a protein present in the circulation. Increase of cross-β structure formation of a particular protein leads, for example, to activation of tPA, which, in turn, induces the formation of plasmin through cleavage of plasminogen and thus results in an increase in the degradation and/or protein clearance.

In one embodiment, the invention discloses a method for increasing extracellular protein degradation and/or protein clearance comprising providing a compound capable of increasing cross-β structure formation (and/or cross-β structure-mediated activity) of a protein present in the circulation. In another embodiment, the compound capable of increasing cross-β structure formation is glucose. Under certain circumstances, the addition of glucose to a protein leads to an irreversible, non-enzymatic glycation reaction in which predominantly a glucose molecule is attached to the free amino groups of lysine residues in a protein. In addition, N-termini and free amino groups of arginine residues are prone to glycation. It is disclosed herein within the experimental part that glycation leads to cross-β structure formation. Hence, the invention discloses a method for increasing extracellular protein degradation and/or protein clearance comprising providing a compound capable of increasing cross-β structure formation of the protein present in the circulation.

Other examples of compounds capable of increasing (or mimicking) cross-β structure formation in a protein are apolar solutions, urea (as disclosed herein within the experimental part), and ions (for example $Zn^{2+}$). However, it is clear that there are also other ways to increase or mimic cross-β structure formation, for example, by denaturation, low pH, temperature, mutations or protein modification in general (for example, oxidation).

In addition to a method for increasing extracellular protein degradation and/or protein clearance comprising increasing cross-β structure formation of the protein present in the circulation via any of the above-described methods to degrade and/or remove, preferably, the protein which comprises the cross-β structure, it is also possible to degrade and/or remove a protein which does not comprise a cross-β structure. This is, for example, accomplished by providing a compound comprising a cross-β structure and a compound comprising tPA-like activity at or near the protein which needs to be degraded and/or removed. An example of a compound comprising a cross-β structure is fibrin or a fragment thereof comprising the cross-β structure. An example of a compound comprising tPA-like activity is tPA.

In another embodiment, the invention discloses a method for decreasing extracellular protein degradation and/or protein clearance comprising decreasing cross-β structure formation of the protein present in the circulation. For instance, the invention discloses a method for decreasing extracellular protein degradation and/or protein clearance comprising providing a compound capable of decreasing cross-β structure formation of the protein present in the circulation. Decreasing of cross-β structure formation is, for example, accomplished by shielding or blocking of the groups involved in the formation of a cross-β structure. Examples of compounds capable of decreasing cross-β structure formation are Congo red, antibodies, β-breakers, phosphonates, heparin, amino-guanidine or laminin.[45] Yet another way to decrease cross-β structure formation in a protein is by removal of a glucose group involved in the glycation of the protein.

In yet another embodiment, the invention discloses a method for modulating extracellular protein degradation and/or protein clearance comprising modulating tPA or tPA-like activity. tPA induces the formation of plasmin through cleavage of plasminogen. Plasmin cleaves fibrin and this occurs during lysis of a blood clot. Activation of plasminogen by tPA is stimulated by fibrin or fibrin fragments, but not by its precursor fibrinogen. The term "tPA-like activity" is herein defined as a compound capable of inducing the formation of plasmin, possibly in different amounts, and/or other tPA-mediated activities. Preferably, tPA-like activity is modified such that it has a higher activity or affinity towards its substrate and/or a cofactor. This is, for example, accomplished by providing the tPA-like activity with multiple binding domains for cross-β structure-comprising proteins. Preferably, the tPA-like activity is provided with multiple finger domains. It is herein disclosed that the three-dimensional structures of the tPA finger domain and the fibronectin finger domains 4-5 reveal striking structural homology with respect to local charge-density distribution. Both structures contain a similar solvent-exposed stretch of five amino acid residues with alternating charge; for tPA, Arg7, Glu9, Arg23, Glu32, Arg30, and for fibronectin, Arg83, Glu85, Lys87, Glu89, Arg90, located at the fifth finger domain, respectively. The charged-residue alignments are located at the same side of the finger module. Hence, the tPA-like activity is provided with one or more extra finger domain(s) which comprise(s) ArgXGlu(X)13Arg(X)6ArgXGlu (SEQ ID NO: 1) or ArgXGluXLysXGluArg (SEQ ID NO: 2).

The activity of tPA and/or the tPA-mediated activation of plasminogen is increased by the binding to fibrin fragments or other protein fragments that have a lysine or an arginine at the carboxy-terminal end. B-type carboxypeptidases, including, but not limited to, carboxypeptidase B (CpB) or Thrombin Activatable Fibrinolysis Inhibitor (TAFI, also named carboxypeptidase U or carboxypeptidase R), are enzymes that cleave off carboxy-terminal lysine and arginine residues of fibrin fragments that would otherwise bind to tPA and/or plasminogen and stimulate plasmin formation.

In one embodiment, the invention discloses a method for increasing extracellular protein degradation and/or protein clearance comprising providing a compound capable of increasing tPA-like and/or tPA-mediated activity or activities. In another embodiment, the invention discloses a method for increasing extracellular protein degradation and/or protein clearance comprising providing a compound capable of increasing tPA-like activity, wherein the compound comprises a cross-β structure. In another embodiment, the invention discloses a method for increasing extracellular protein degradation and/or protein clearance comprising providing a compound capable of inhibiting B-type carboxypeptidase activity. In an additional embodiment, the compound comprises carboxypeptidase inhibitor (CPI) activity.

In yet another embodiment, the invention discloses a method for decreasing extracellular protein degradation and/or protein clearance comprising providing a compound capable of decreasing tPA-like activity. In one aspect, the invention discloses a method for decreasing extracellular protein degradation and/or protein clearance comprising providing a compound capable of decreasing tPA-like activity or tPA-mediated activity or activities, wherein the compound is a protein and/or a functional equivalent and/or a functional fragment thereof. For example, such a compound capable of decreasing tPA-like activity is an inhibitor of tPA or a substrate of tPA which binds and does not let go. Examples of a compound capable of decreasing tPA-like activity or tPA-mediated activity include, but are not limited to, lysine, arginine, e-amino-caproic acid or tranexamic acid, serpins (for example, neuroserpin, PAI-1), tPA-Pevabloc, antibodies that inhibit tPA-like activity or tPA-mediated activity or B-type carboxypeptidase(s). For example, providing lysine results in the prevention or inhibition of binding of a protein comprising a C-terminal lysine-residue to the Kringle domain of plasminogen. Hence, tPA activation is prevented or inhibited. Preferably, the compound capable of decreasing tPA-like activity or tPA-mediated activity or activities reduce the tPA-like activity or tPA-mediated activity or activities and, even more preferably, the tPA-like activity or tPA-mediated activity or activities is completely inhibited.

A functional fragment and/or a functional equivalent are typically defined as a fragment and/or an equivalent capable of performing the same function, possibly in different amounts. For example, a functional fragment of an antibody capable of binding to a cross-β structure would be the Fab' fragment of the antibody.

In yet another embodiment, the invention discloses a method for modulating extracellular protein degradation and/or protein clearance comprising modulating an interaction between a compound comprising a cross-β structure and a compound comprising tPA-like activity. In another embodiment, the invention discloses a method for decreasing extracellular protein degradation and/or protein clearance comprising decreasing an interaction between a compound comprising a cross-β structure and a compound comprising tPA-like activity. Such a compound is, for example, a chemical, a proteinaceous substance or a combination thereof. In an additional embodiment, the invention discloses a method for decreasing extracellular protein degradation and/or protein clearance comprising providing a compound capable of decreasing an interaction between a compound comprising a cross-β structure and a compound comprising tPA-like activity. In one aspect, the invention discloses a method for decreasing extracellular protein degradation and/or protein clearance according to the invention, wherein the compound is a protein and/or a functional equivalent and/or a functional fragment thereof. In another aspect, the protein is an antibody and/or a functional equivalent and/or a functional fragment thereof.

Other examples are Congo red or Thioflavin. The invention also discloses a method for decreasing extracellular protein degradation and/or protein clearance comprising decreasing an interaction between a compound comprising a cross-β structure and a compound comprising tPA-like activity, wherein the interaction is decreased by providing a compound capable of competing with the interaction. More in particular, the compound capable of competing with the interaction comprises a finger domain and, even more particularly, the finger domain comprises a stretch of at least 5 amino acid residues with alternating charge, for example, ArgXGlu$(X)_{13}$Arg$(X)_6$ArgXGlu (SEQ ID NO: 1) or ArgXGluXLysX-GluArg (SEQ ID NO: 2). In one aspect, the compound is fibronectin, FXII, HGFa or tPA.

In another embodiment, the invention also comprises a method for increasing extracellular protein degradation and/or protein clearance comprising increasing an interaction between a compound comprising a cross-β structure and a compound comprising tPA-like activity. This is, for example, accomplished by providing a compound capable of increasing an interaction between a compound comprising a cross-β structure and a compound comprising tPA-like activity. In one aspect, the compound capable of increasing an interaction between a compound comprising a cross-β structure and a compound comprising tPA-like activity is a protein and/or a functional equivalent and/or a functional fragment thereof. For example, an antibody which stabilizes the interaction between a compound comprising a cross-β structure and a compound comprising tPA-like activity, rendering the tPA-like activity in a continuous activated state, results in increased protein degradation and/or protein clearance. However, it is appreciated that increasing an interaction between a compound comprising a cross-β structure and a compound comprising tPA-like activity is also accomplished by mutations in either the compound comprising a cross-β structure or in the compound comprising tPA-like activity, like swapping of domains (for example, by providing the compound comprising tPA-like activity with other or more finger domains obtainable from tPA, fibronectin, FXII or HGFa), or by including binding domains of, for example, RAGE or CD36.

In yet another embodiment, the invention discloses a method for modulating extracellular protein degradation and/or protein clearance comprising modulating an interaction of a compound comprising tPA-like activity and the substrate of the activity. It is clear that there are multiple ways by which the interaction can either be increased or decreased. An increase in the interaction between a compound comprising tPA-like activity and the substrate of the activity is, for example, accomplished by providing the compound comprising tPA-like activity with a mutation or mutations which improve the affinity of the compound with tPA-like activity for its substrate.

In yet another embodiment, the invention discloses a method for removing cross-β structures from the circulation, using a compound comprising a cross-β structure-binding domain. In one aspect, the compound is tPA or the finger domain of tPA. It is clear that the invention also comprises other cross-β structure-binding domains, including, but not limited to, the finger domains of HGFa, FXII and fibronectin (SEQ ID NOs: 3-17). It is clear that the invention also comprises antibodies that bind cross-β structures.

The present invention further discloses the use of a novel strategy to prevent the formation of, or to decrease/diminish, (amyloid) plaques involved in a conformational disease, type II diabetes and/or aging (e.g., Alzheimer's disease). Plaques are typically defined as extracellular fibrillar protein deposits (fibrillar aggregates) and are characteristic of degenerative diseases. The "native" properties of the constituent amyloid proteins may vary: some are soluble oligomers in vivo (e.g., transthyretin in familial amyloid polyneuropathy), whereas others are flexible peptides (e.g., amyloid-b in Alzheimer's disease (AD)). The basic pathogenesis of conformational diseases, for example, neurodegenerative disorders (AD, prion disorders), is thought to be related to abnormal pathologic protein conformation, i.e., the conversion of a normal cellular and/or circulating protein into an insoluble, aggregated, β-structure-rich form which is deposited in the brain. These deposits are toxic and produce neuronal dysfunction and death. The formation of cross-β structures has thus far only been associated with severe pathological disorders. The results herein show that tPA and other receptors for cross-β structure-forming proteins can bind denatured proteins, indicating that a large number of proteins are capable of adopting a conformation containing cross-β or cross-β-like structures. Taken together, the formation of a cross-β structure initiates or participates in a physiological cascade of events necessary to adequately deal with removal of unwanted molecules, i.e., misfolded proteins, apoptotic cells or even pathogens. By increasing cross-β structure formation in a protein involved in a conformational disease, the pathway for protein degradation and/or protein clearance is activated and the protein is degraded, resulting in a decreasing plaque or, in another aspect, the plaque is completely removed. Hence, the effects of the conformational disease are diminished or, alternatively, completely abolished.

In a further embodiment, the invention discloses the use of a compound capable of increasing cross-β structure formation for diminishing plaques involved in a conformational disease. In another embodiment, the invention discloses the use of a compound capable of binding to a cross-β structure for diminishing plaques and/or inhibiting cross-β structure-mediated toxicity involved in a conformational disease. In one use of the invention, the compound is a protein and/or a functional equivalent and/or a functional fragment thereof and, in another aspect, the protein is tPA, a finger domain, an antibody and/or a functional equivalent and/or a functional fragment thereof. Examples of such antibodies are 4B5 or 3H7.

In a yet further embodiment, the invention discloses the use of a compound capable of increasing tPA-like activity for diminishing plaques involved in a conformational disease. In one aspect, the tPA-like activity is modified such that it has a higher activity or affinity towards its substrate and/or cofactor. This is, for example, accomplished by providing the tPA-like activity with multiple binding domains for cross-β structure-comprising proteins. In another aspect, the binding domain comprises a finger domain and, in an additional aspect, the finger domain comprises a stretch of at least five amino acid residues with alternating charge, for example ArgXGlu(x)$_{13}$Arg(X)$_6$ArgXGlu (SEQ ID NO: 1) or ArgX-GluXLysXGluArg (SEQ ID NO: 2). In an additional embodiment, the finger domain is derived from fibronectin, FXII, HGFa or tPA.

In yet another embodiment, the invention discloses the use of a compound capable of binding to a cross-β structure for the removal of cross-β structures. In one aspect, the compound is a protein and/or a functional equivalent and/or a functional fragment thereof. In an additional aspect, the compound comprises tPA or tPA-like activity and/or a functional equivalent and/or a functional fragment thereof. In a further embodiment, the functional fragment comprises a finger domain. In one embodiment, the finger domain comprises a stretch of at least five amino acid residues with alternating charge, for example, ArgXGlu(X)$_{13}$Arg(X)$_6$ArgXGlu (SEQ ID NO: 1) or ArgXGluXLysXGluArg (SEQ ID NO: 2). In yet an additional embodiment, the finger domain is derived from fibronectin, FXII, HGFa or tPA. In another embodiment, the protein is an antibody and/or a functional equivalent and/or a functional fragment thereof. With this use, the invention discloses, for example, a therapeutic method to remove cross-β structure-comprising proteins from, for example, the circulation, such as via extracorporeal dialysis. For example, a patient with sepsis is subjected to such use by dialysis of the blood of that patient through means which are provided with, for example, immobilized finger domains. One could, for example, couple the finger domains to a carrier or to the inside of the tubes used for dialysis. In this way, all cross-β structure-comprising proteins will be removed from the blood stream of the patient, thus, relieving patients of the negative effects caused by the cross-β structure-comprising proteins. Besides finger domain-comprising compounds, it is also possible to use other cross-β structure-binding compounds, like antibodies or Congo Red. It is also clear that the use could be applied in hemodialysis of kidney patients.

In yet another embodiment, the invention discloses the use of a compound capable of increasing or stabilizing an interaction of a compound comprising a cross-β structure and a compound comprising tPA-like activity for diminishing plaques involved in a conformational disease. Examples of a compound capable of increasing or stabilizing an interaction of a compound comprising a cross-β structure and a compound comprising tPA-like activity are given herein. In another use, the invention is used to treat the conformational disease Alzheimer or diabetes. It is clear that the invention not only discloses a use to decrease/diminish plaques involved in a conformational disease, but also that the onset of the disease can also be inhibited or even completely prevented. Examples of diseases which can be prevented and/or treated according to the invention are conformational disease, amyloidosis-type diseases, atherosclerosis, diabetes, bleeding, thrombosis, cancer, sepsis and other inflammatory diseases, Multiple Sclerosis, auto-immune diseases, disease associated with loss of memory or Parkinson and other neuronal diseases (epilepsy).

In another embodiment, the invention discloses the use of an antibody capable of recognizing a cross-β structure epitope for determining the presence of plaque involved in a conformational disease. In yet another embodiment, the invention discloses the use of a cross-β structure-binding domain (such as a finger domain from, for example, tPA) for determining the presence of a plaque involved in a conformational disease.

These uses of the invention provide a new diagnostic tool. It was not until the present invention that a universal b-structure epitope was disclosed and that a diagnostic assay could be based on the presence of the cross-β structure. Such use is particularly useful for diagnostic identification of conformational diseases or diseases associated with amyloid formation, such as Alzheimer or diabetes. It is clear that this diagnostic use is also useful for other diseases which involve cross-β structure formation, like all amyloidosis-type diseases, atherosclerosis, diabetes, bleeding, cancer, sepsis and other inflammatory diseases, Multiple Sclerosis, auto-immune diseases, disease associated with loss of memory or Parkinsons and other neuronal diseases (epilepsy). For example, one can use a finger domain (of, for example, tPA) and provide it with a label (radioactive, fluorescent, etc.). This labeled finger domain may be used either in vitro or in vivo for the detection of cross-β structure-comprising proteins and, thus, for determining the presence of a plaque involved in a conformational disease. One can, for example, use an ELISA assay to determine the amount of sepsis in a patient or one can localize a plaque involved in a conformational disease.

In yet another embodiment, the invention discloses a recombinant tPA comprising an improved cross-β structure-binding domain or multiple cross-β structure-binding domains. In one aspect, tPA is provided with multiple, possibly different, finger domains. A recombinant tPA comprising an improved cross-β structure-binding domain or multiple cross-β structure-binding domains is used for different purposes, for example, in a method for the improved treatment of thrombolysis or for the removal of cross-β structure-comprising proteins from the circulation of a patient in need thereof. Another use of a recombinant tPA comprising an improved cross-β structure-binding domain or multiple cross-β structure-binding domains is in diagnostic assays such as, for example, in a BSE detection kit or in imaging experiments. This imaging with a recombinant tPA comprising an improved cross-β structure-binding domain or multiple cross-β structure-binding domains is, for example, useful for detection of apoptosis. For example, labeled tPA, such as, but not limited to, radio-labeled tPA, is inoculated in an individual, followed by detection and localization of labeled tPA in the body. It is clear that recombinant tPA comprising a cross-β structure-binding domain or multiple cross-β structure-binding domains are also useful in therapeutic applications.

Because this invention has made clear that the cross-β structure is harmful when present in certain parts of the body, like the brain, for example, and the damage is effected by the combination of cross-β structures with tPA, a method is provided to inhibit cross-β structure-mediated effects comprising providing an effective amount of a protein comprising a finger domain to block the binding sites of the cross-β structure for tPA. Cross-β structure-mediated effects may even be further diminished by providing an effective amount of B-type carboxypeptidase activity to inhibit the tPA activity.

In another embodiment, the local cross-β structure-mediated effect can be used against tumors. To that effect, cross-β structure-mediated effects are locally induced to increase local cytotoxicity and/or fibrinolysis comprising locally administering an effective amount of cross-β structures and/or cross-β structure-inducing compounds in conjunction with tPA or a compound with tPA-like activity and/or CPI or a compound with CPI-like activity.

The present invention discloses in a further embodiment a method which is carried out ex vivo, e.g., by dialysis. According to this embodiment, the circulating fluid (blood) of a subject is brought in a system outside the body for clearing cross-β structures from the circulation. In one aspect, such a system is a flow-through system connected to the body circulation with an inlet and an outlet. The cross-β structures are cleared by binding to a cross-β binding compound as defined hereinbefore. It is very important that no elements, such as the cross-β binding compounds from the system, are brought into the subject's circulation. For that reason, among others, preferred systems are dialysis systems. The invention further discloses devices for carrying out methods as disclosed herein. Thus, the invention discloses a separation device for carrying out a method according to the invention wherein the apparatus comprises a system for transporting circulation fluids ex vivo, the system provided with means for connecting to a subject's circulation for entry into the system and return from the system to the subject's circulation, the system comprising a solid phase, the solid phase comprising at least one compound capable of binding cross-β structures. Compounds for binding cross-β structures have been disclosed herein. In one aspect, the device is a dialysis apparatus.

The invention also provides for detection of cross-β structures in samples. Such samples may be tissue samples, biopsies and the like, body fluid samples, such as blood, serum, liquor, CSF, urine, and the like. The invention thus discloses a method for detecting cross-β structures in a sample, comprising contacting the sample with a compound capable of binding cross-β structures, allowing for binding of cross-β structures to the compound and detecting the complex formed through binding.

Cross-β binding compounds have been defined hereinbefore. Detection of the complex or one of its constituents can be done through any conventional means involving antibodies or other specific binding compounds, further cross-β binding compounds, etc. Detection can be direct such as by labeling the complex or a binding partner for the complex or its constituents, or even by measuring a change in a physical or chemical parameter of the complex versus unbound material. It may also be indirect by further binding compounds provided with a label. A label may be a radioactive label, an enzyme, a fluorescent molecule, etc.

The invention further discloses devices for carrying out the diagnostic methods. Thus, the invention discloses a diagnostic device for carrying out a method according to the invention, comprising a sample container, a means for contacting the sample with a cross-β binding compound, a cross-β binding compound and a means for detecting bound cross-β structures. In one embodiment, the device comprises a means for separating unbound cross-β structures from bound cross-β structures which can be typically done by providing the cross-β binding compounds on a solid phase.

BRIEF DESCRIPTION OF THE DRAWINGS

FIG. 1 is a schematic representation of the "cross-β structure pathway." The cross-β structure is found in a number of proteins (1). The formation of a cross-β structure can be triggered by several physiological or pathological conditions and subsequently initiates a cascade of events, the "cross-β structure pathway." Among the factors that trigger or regulate the formation of a cross-β structure within a given protein are: 1) the physicochemical properties of the protein, 2) proteolysis, 3) regulated post-translational modification, including cross-linking, oxidation, phosphorylation, glycosylation and glycation, 4) glucose, and 5) zinc. Certain mutations within the sequence of a protein are known to increase the ability of the protein to adopt a cross-β structure and form amyloid fibers. These mutations are often found in hereditary forms of amyloidosis, for example in AD. The present invention discloses multiple novel examples of proteins capable of adopting a cross-β structure. Several proteins are known to bind cross-β-containing proteins (2). These proteins are part of the herein disclosed signaling cascade ("cross-β structure pathway") that is triggered upon formation of a cross-β structure. The "cross-β structure pathway" is modulated in many ways (3, 4, 5). Factors that regulate the pathway include modulators of synthesis and secretion including NO regulators, as well as modulators of activity, including protease inhibitors. The pathway is involved in many physiological and pathological processes including, but not limited to, atherosclerosis, diabetes, amyloidosis, bleeding, inflammation, multiple sclerosis, Parkinson's disease, sepsis, hemolytic uremic syndrome (7). Given the established role for tPA in long term potentiation, the "cross-β structure pathway" may also be involved in learning.

FIG. 2 illustrates a cross-β structure in fibrin. Panel A depicts Thioflavin T fluorescence of a fibrin clot. A fibrin clot was formed in the presence of Thioflavin T and fluorescence was recorded at indicated time points. Background fluorescence of buffer, Thioflavin T and a clot formed in the absence of Thioflavin T, was substracted. Panel B is a graph depicting circular dichroism analysis of fibrin-derived peptides 85, 86 and 87. Ellipticity (Dg.$cm^2$/dmol) is plotted against wavelength (nm). The CD spectra demonstrates that peptides 85 and 86, but not peptide 87, contain β-sheets. Panel C shows that X-ray fiber diffraction analysis of peptide 85 reveals that the peptide forms cross-β sheets. Panel D is a graph showing plasminogen activation assay with fibrin peptides 85, 86 and 87. It is seen that peptides 85 and 86, both containing a cross-β structure, stimulate the formation of plasmin by tPA, whereas peptide 87, which lacks a cross-β structure, does not.

FIG. 3 is a set of graphs depicting binding of tPA, plasminogen and plasmin to Aβ. Aβ was coated onto plastic 96-well plates. Increasing concentrations of either (A) tPA or (B) plasmin(ogen) were allowed to bind to the immobilized peptide. After extensive washing, tPA and plasmin(ogen) binding was assessed by enzyme-linked immunosorbent assays using anti-tPA and anti-plasminogen antibodies. Binding of (C) tPA and (D) plasmin to Aβ in the presence of 50 mM ϵ-aminocaproic acid (ϵ-ACA) was assessed as in A and B.

FIG. 4 is a set of graphs illustrating stimulation of tPA-mediated plasmin formation by Aβ and synergistic stimulation of cell detachment by plasminogen and Aβ. Panel A depicts that plasminogen (200 μg/ml) and tPA (200 pM) were incubated with Aβ (5 μM) or control buffer. Samples were taken from the reaction mixture at the indicated periods of time and plasmin activity was measured by conversion of the chromogenic plasmin substrate S-2251 at 405 nm. Panel B shows that N1E-115 cells were differentiated and received the indicated concentrations of plasmin in the presence or absence of 25 μM Aβ. After 48 hours, the dead cells were washed away and the remaining adherent cells were stained with methylene blue. Plasmin cannot prevent Aβ-induced cell detachment. Panel C illustrates that N1E-115 cells were differentiated and received the indicated concentrations of plasminogen in the presence or absence of 10 μM Aβ. After 24 hours, cell detachment was assessed. Aβ or plasminogen alone does not affect cell adhesion, but cause massive cell detachment when added together. Panel D is an immunoblot analysis of plasmin formation and laminin degradation. Differentiated N1E-115 cells were treated with or without Aβ (10 μM) in the absence or presence of added plasminogen. Addition of Aβ results in the formation of plasmin (bottom panel) and in degradation of laminin (top panel).

Figure 5:
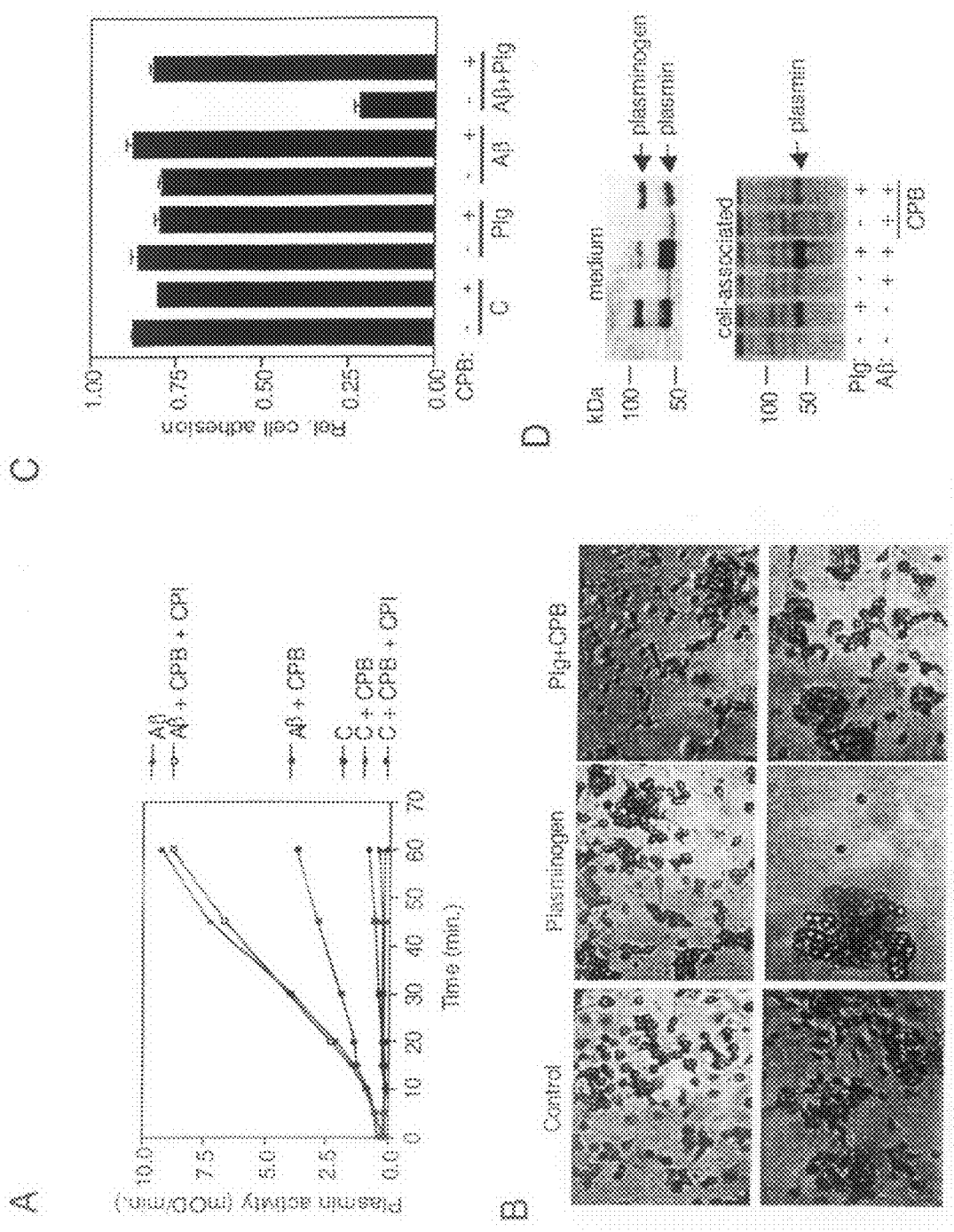

FIG. 5 depicts graphs illustrating that carboxypeptidase B inhibits Aβ-stimulated tPA-mediated plasmin formation and cell detachment. Panel A shows that plasminogen (200 μg/ml) and tPA (200 pM) were incubated with Aβ (5 μM) or control buffer. Samples were taken from the reaction mixture at the indicated periods of time and plasmin activity was measured by conversion of the chromogenic plasmin substrate S-2251 at 405 nm. The reaction was performed in the absence or the presence of 50 μg ml$^{-1}$ carboxypeptidase B (CpB) and in the absence or presence of 3.5 μM carboxypeptidase inhibitor (CPI). CpB greatly attenuates A-stimulated plasmin formation. Panel B shows that N1E-115 cells were differentiated and treated with Aβ (10 μM), plasminogen (Plg, 20 μg ml$^{-1}$) and/or CpB (1 μM) as indicated. After 24 hours, the cells were photographed. Panel C illustrates that, subsequently, the cells were washed once with PBS and the remaining cells were quantified as percentage-adhered cells by methylene blue staining. In Panel D, the cells were treated as in Panels B and C and medium and cell fractions were collected and analyzed by Western blot using an anti-plasmin(ogen) antibody. Aβ stimulates plasmin formation that is inhibited by CpB.

Figure 6:
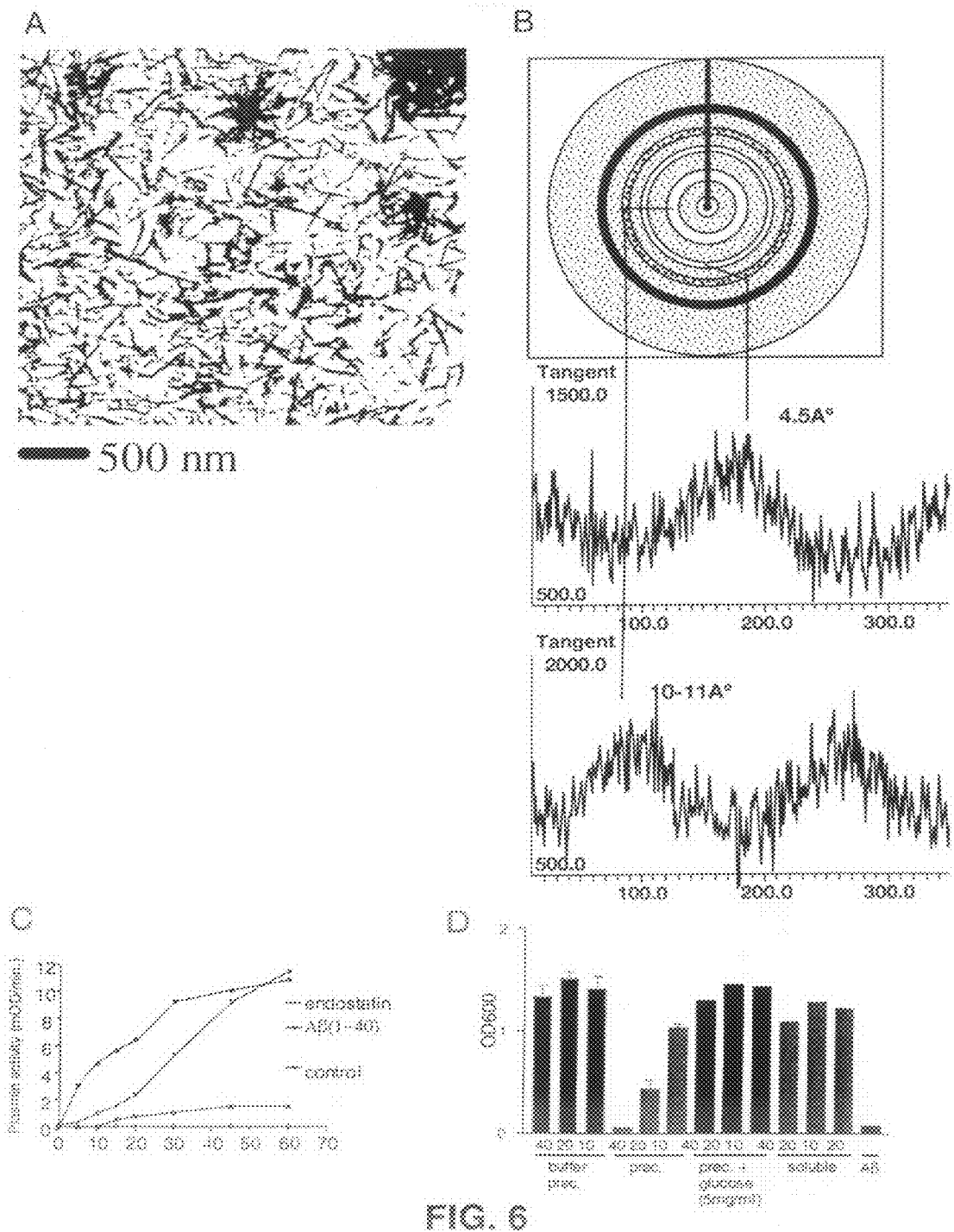

FIG. 6 is a set of graphs illustrating that endostatin can form fibers comprising cross-β structure and stimulates plasminogen activation. In Panel A, TEM shows the formation of endostatin fibers. Panel B contains an X-ray analysis that reveals the presence of cross-β structure in precipitated (prec.) endostatin. Panel C is a plasminogen activation assay demonstrating the stimulating activity of cross-β structure-containing endostatin on tPA-mediated plasmin formation. Aβ is shown for comparison. Panel D is an analysis of endostatin-induced cell death by methylene blue staining. It is seen that only the precipitated form is capable of efficiently inducing cell death. Direct cell death, but not cell detachment, is protected in the presence of sufficient glucose. Buffer prec. indicates control buffer.

Figure 7:
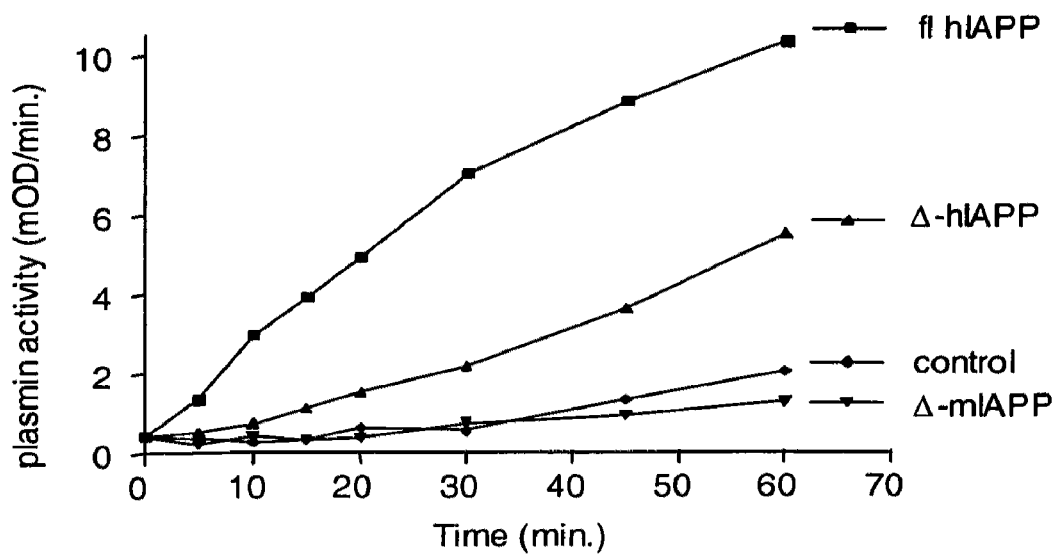

FIG. 7 is a graph showing that IAPP stimulates tPA-mediated plasminogen activation. Both full length (fl-hIAPP) and truncated amyloid core (Δ-hIAPP), but not mouse IAPP (Δ-mIAPP), stimulate tPA-mediated plasminogen activation.

FIG. 8 is a set of graphs illustrating glycated albumin: Thioflavin T and tPA binding, TEM images, X-ray fiber diffraction. Panel A is an ELISA showing binding of tPA to albumin-g6p. Panel B shows competition of tPA binding to albumin-g6p by Congo red as determined using ELISA. Panel C shows fluorescence measurements of Thioflavin T binding to albumin-g6p, which is incubated for two, four, or 23 weeks. Panel D shows that inhibition of the fluorescent signal is obtained upon incubation of 430 nM of albumin-g6p with 19 μM of Thioflavin T by tPA. Panels E and F illustrate that spectrophotometric analysis at 420 nm shows that increasing amounts of tPA result in a decrease of the specific absorbance obtained upon incubation of 500 nM of albumin-g6p with 10 μM of Thioflavin T. Panels G, H and I are electron micrographs showing (G) amorphous precipitates of four weeks glycated albumin-g6p, (H) bundles of fibrillar aggregates of 23 weeks incubated albumin-g6p, and (I) two weeks glycated albumin-g6p. Panel J is an X-ray scattering of albumin-g6p (23 weeks). Scattering intensities are color coded on a linear scale and decreases in the order white-grey-black. Scattering from amorphous control albumin is subtracted, as well as scattering from the capillary glass wall and from air. d-spacings and the direction of the fiber axis are given and preferred orientations are indicated with arrows. Panel K is radial scan of albumin control and albumin-g6p (23 weeks). Panel L is a radial scan of albumin-g6p (23 weeks), showing repeats originating from fibrous structure, after subtracting background scattering of amorphous precipitated albumin. d-spacings (in Å) are depicted above the peaks. Panel M contains tangential scans along the 20 scattering-angles corresponding to indicate d-spacings. The scans show that the 4.7 Å repeat, which corresponds to the hydrogen-bond distance within individual β-sheets, and the 6 Å repeat, are oriented perpendicular to the 2.3 Å repeat that runs parallel to the fiber axis. Panel N is a schematic drawing of the orientation of the cross-β structures in albumin-g6p (23 weeks) amyloid fibers.

FIG. 9 illustrates fibers formation of human hemoglobin. Panel A depicts binding of tPA to in vitro glycated Hb-g6p. Panel B is an electron micrograph showing in vitro glycated Hb, which aggregates in an amorphous and fibrous manner.

FIG. 10 shows that amyloid properties of albumin-AGE are introduced irrespective of the carbohydrate or carbohydrate derivative used for glycation. Panels A-I illustrate-Congo red fluorescence of air-dried albumin preparations. Fluorescence was measured with albumin incubated with buffer (Panel A) or with buffer and NaCNBH$_3$ (Panel B), with amyloid core peptide of human IAPP(Panel C), Aβ (Panel D), with albumin incubated with g6p (Panel E), glucose (Panel F), fructose (Panel G), glyceraldehyde (Panel H), and glyoxylic acid (Panel I). Panel J shows that Thioflavin T-amyloid fluorescence was measured in solution with the indicated albumin preparations. Panels K and L show that binding of amyloid-binding serine protease tPA to albumin preparations was assayed using an ELISA set-up. In Panel K, binding of tPA to albumin-glucose, -fructose, -glyceraldehyde, -glyoxylic acid, and albumin-buffer controls is shown. In Panel L, binding of tPA to positive controls albumin-g6p, Aβ and IAPP is shown, as well as to albumin incubated with control buffer.

FIG. 11 illustrates analysis of Congo red and tPA binding to Aβ. Panel A shows binding of tPA to immobilized Aβ as measured using an ELISA. Panel B illustrates the influence of increasing concentrations of Congo red on binding of tPA to Aβ. In the ELISA, 10 μg ml$^{-1}$ of Aβ (1-40) was coated and incubated with 40 nM of tPA and 0-100 μM of Congo red.

Figure 12:
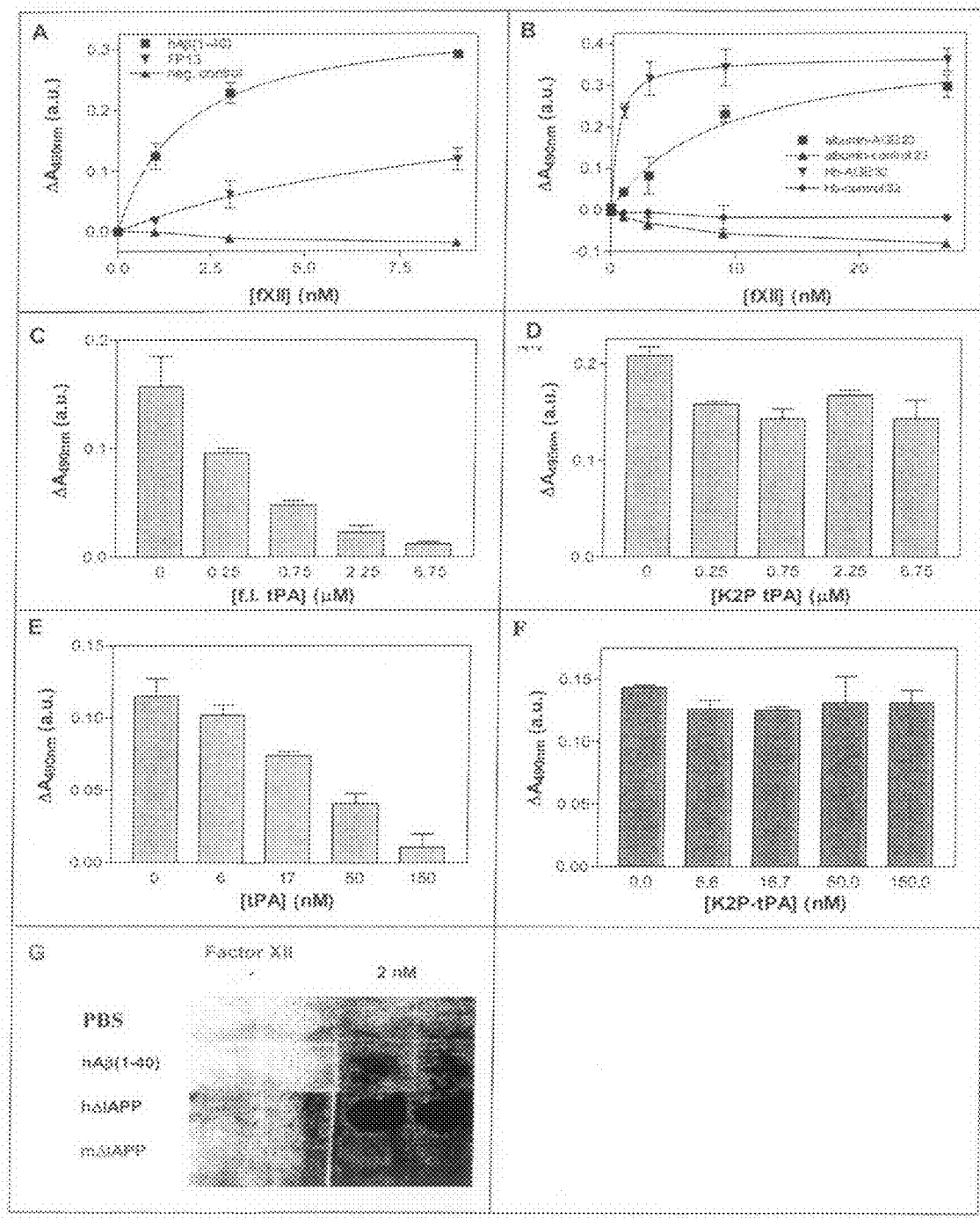

FIG. 12 illustrates binding of human FXII to amyloid peptides and proteins that contain the cross-β structure fold. Panels A and B show binding of FXII to prototype amyloid peptides hAβ (1-40) and human fibrin fragment α$_{147-159}$ FP13, and albumin-AGE and Hb-AGE, that all contain cross-β structure, were tested in an ELISA. FXII does not bind to negative controls mouse A islet amyloid polypeptide (ΔmIAPP), albumin-control and Hb-control, all three lacking the amyloid-specific structure. $k_D$'s for hAβ (1-40), FP13, albumin-AGE and Hb-AGE are approximately 2, 11, 8 and 0.5 nM, respectively. Panels C and D depict that coated hAβ (1-40) was incubated with 2.5 nM FXII in binding buffer, in the presence of a concentration series of human recombinant tissue-type plasminogen activator (ACTILYSE®, full-length tPA), or RETEPLASE® (K2P-tPA). The f.l. tPA- and K2P-tPA concentration was, at maximum, 135 times the $k_D$ for tPA binding to hAβ (1-40) (50 nM). Panels E and F show that coated amyloid albumin-AGE was incubated with 15 nM FXII in binding buffer, in the presence of a concentration series of f.l. tPA or K2P-tPA. The tPA concentration was, at maximum, 150 times the $k_D$ for tPA binding to albumin-AGE (1 nM). Panel G illustrates that binding of FXII to hAβ (1-40) and the prototype amyloid human amylin fragment hΔIAPP was tested using dot blot analysis. 10 μg of the peptides that contain cross-β structure as well as the negative control peptide mΔIAPP and phosphate-buffered saline (PBS) were spotted in duplicate. FXII specifically bound to hAβ (1-40) as well as to hΔIAPP.

FIG. 13 illustrates that finger domains bind to amyloid (poly)peptides. Panel A depicts binding of tPA and K2-P tPA to albumin-g6p. Panel B shows binding of tPA and K2-P tPA to Aβ (1-40). The tPA antibody used for detection recognizes both tPA and K2-P-tPA with equal affinity (not shown). Panel C shows binding of tPA-F-GST and tPA to immobilized Aβ (1-40) and albumin-g6p. Control RPTPμ-GST does not bind Aβ or albumin-g6p. Panel D is a pull-down assay with insoluble Aβ fibers and tPA domains. Conditioned BHK medium from stably transfected cell lines expressing tPA F, F-EGF, EGF, F-EGF-K1 and K1 with a C-terminal GST tag, as well as the tag alone, was used. "Control," medium before the pull-down, "Aβ," washed amyloid Aβ pellet, after the pull-down, "Sup," medium after extraction with Aβ. Samples were analyzed on Western blot using rabbit anti-GST antibody Z-5. Panels E-G are ELISA showing binding of tPA F-EGF-GST and f.l. recombinant tPA to amyloid Aβ (Panel E), FP13 (Panel F) and IAPP (Panel G). mΔIAPP was coated as non-amyloid negative control (Panel E). Peptides were immobilized on ELISA plates and overlayed with concentration series of tPA and F-EGF-GST. GST was used as a negative control. Binding was detected using rabbit anti-GST antibody Z-5. Panels H-M depict immunohistochemical analysis of binding of tPA F-EGF-GST to amyloid deposits in human brain inflicted by AD. Brain sections were overlayed with tPA F-EGF-GST (Panels H and J) or negative control GST (Panel L). The same sections were incubated with Congo red (Panels I, K and M) to locate amyloid deposits. Panels N and O are pull-down assays with insoluble Aβ fibers and finger domains. Recombinant F domains with a C-terminal GST tag were expressed by stably transfected BHK cells. "Control," medium before the pull-down, "Aβ," washed amyloid Aβ pellet, after the pull-down, "Sup," medium after extraction with Aβ. Samples were analyzed on Western blot using rabbit anti-GST antibody Z-5.

FIG. 14 illustrates the finger module. Panel A is a schematic representation of the location of the finger domain in tPA, factor XII, HGFa and fibronectin ("FN"). Panel B is an alignment of the amino acid sequence of the finger domain of the respective proteins. Specifically: tPA, FXII, HGFa, FN F1, FN F2, FN F3, FN F4, FN F5, FN F6, FN F7, FN F8, FN F9, FN F10, FN F11, and FN F12 (SEQ ID NOs: 3-17 respectively). Panel C is a representation of the peptide backbone of the tPA finger domain and the fourth and fifth finger domain of FN. Conserved disulfide bonds are shown in ball and stick.

FIG. 15 shows that antibodies elicited against amyloid peptides cross-react with glycated proteins, and vice versa. Panels A-C are ELISA with immobilized g6p-glycated albumin-AGE:23 and Hb-AGE, their non-glycated controls (Panel A), Aβ (1-40) (Panel B), and IAPP and mΔIAPP (Panel C). For the Aβ ELISA, polyclonal anti-human vitronectin antibody α-hVn K9234 was used as a negative control. Panel D shows binding of α-AGE1 to immobilized Aβ (1-40) on an ELISA plate after pre-incubation of α-AGE 1 with IAPP fibers. Panel E is a pull-down assay with anti-AGE1 antibody and amyloid fibers of Aβ (16-22) (lanes 1-2), Aβ (1-40) (lanes 4-5) and IAPP (lanes 6-7). After pelleting and washing of the fibers, samples were boiled in non-reducing sample buffer and analyzed by SDS-PAGE. s=supernatant after amyloid extraction, p=amyloid pellet after extraction, m=molecular marker. Panels F and G depict that in an ELISA set-up, immobilized Aβ (1-40) (Panel F) and IAPP (Panel G) are co-incubated with tPA and 250 or 18 nM α-AGE1, respectively. Panel H shows that in an ELISA set-up binding of α-Aβ (1-42) H-43 to immobilized positive control Aβ (1-40), and to IAPP and albumin-AGE:23 is tested. Albumin-control: 23 and mΔIAPP are used as negative controls. Panel I depicts binding of 100 nM α-Aβ (1-42) H-43 to IAPP, immobilized on an ELISA plate, in the presence of a concentration series of tPA. Panels J and K are ELISA showing binding of a polyclonal antibody in mouse serum elicited against albumin-AGE:23 and Aβ (1-40) (ratio 9:1) ("poab anti-amyloid") and of a polyclonal antibody elicited against a control protein ("control serum") to immobilized IAPP (Panel J) and albumin-AGE:23 (Panel K). Serum was diluted in PBS with 0.1% v/v Tween20. Panel L is an ELISA showing binding of mouse poab anti-amyloid serum to amyloid Aβ (1-40), hΔIAPP and fibrin fragment $\alpha_{148-160}$ FP13. Control serum with antibodies raised against an unrelated protein, buffer and immobilized non-amyloid mΔIAPP and fibrin fragment $\alpha_{148-157}$ FP10 were used as negative controls. Panel M is an immunohistochemical analysis of the binding of rabbit anti-AGE2 to a spherical amyloid plaque (arrow) in a section of a human brain afflicted by AD. Magnification 400×. Panel N is a Congo red fluorescence of the same section. Magnification 630×.

FIG. 16 illustrates that monoclonal anti-cross-β structure antibody 3H7 detects glycated hemoglobin, Aβ, IAPP and FP13. ELISA showing binding of mouse monoclonal anti-cross-β structure antibody 3H7 to (Panel A) glycated hemoglobin vs. control unglycated hemoglobin or (Panel B) Aβ, hIAPP, ΔmIAPP and fibrin fragment $\alpha_{148-160}$ FP13.

Figure 17:
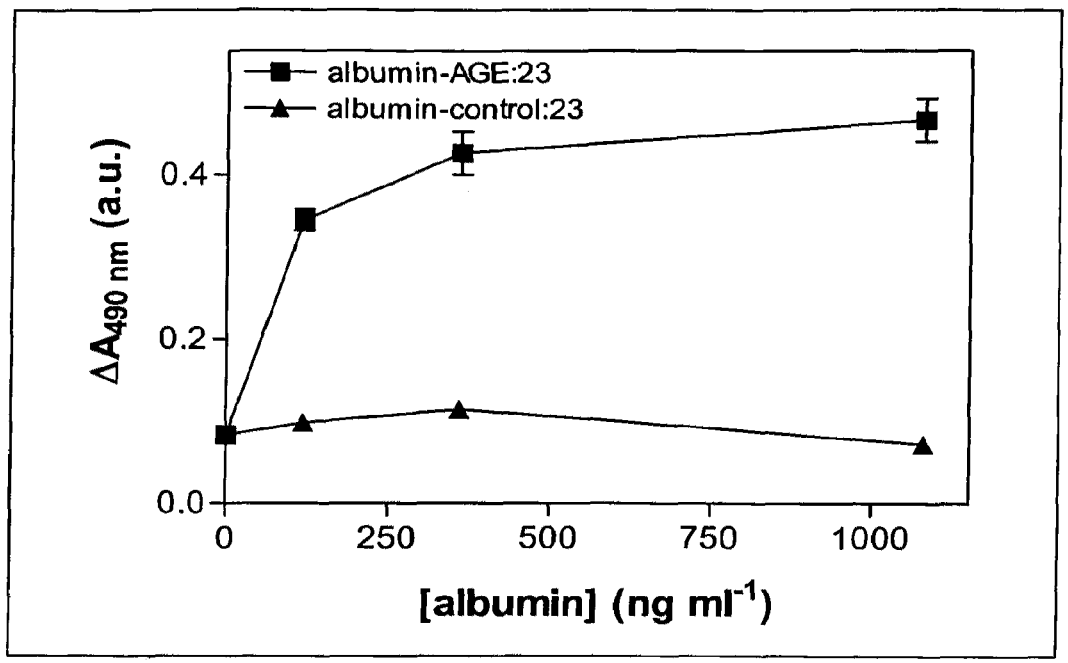

FIG. 17 is a sandwich ELISA for detection of amyloid albumin-AGE or amyloid hemoglobin in solution. Immobilized recombinant tPA on Exiqon protein Immobilizers was overlayed with albumin-AGE:23 solution or albumin-control:23 solution at the indicated concentrations. Bound amyloid structures were detected with anti-Aβ (1-42) H-43 (A).

DETAILED DESCRIPTION OF THE INVENTION

The invention discloses (i) the identification of a "cross-β structure pathway," (ii) the identification of multiligand receptors as being cross-β structure receptors, (iii) the identification of the finger domain as a cross-β-binding module and (iv) the identification of finger-containing proteins, including tPA, FXII, HGFa and fibronectin as part of the "cross-β structure pathway."

This invention further discloses compounds not previously known to bind cross-β structure.

As disclosed herein, the invention describes compounds and methods for the detection and treatment of diseases associated with the excessive formation of a cross-β structure. Such diseases include known conformational diseases including Alzheimer disease and other types of amyloidosis. The present invention also discloses that other diseases not yet known to be associated with excessive formation of cross-β structures are also caused by excessive formation of cross-β structures. Such diseases include atherosclerosis, sepsis, diffuse intravascular coagulation, hemolytic uremic syndrome, preeclampsia, rheumatoid arthritis, autoimmune diseases, thrombosis and cancer.

According to the invention, the compound or means for binding the cross-β structure is a cross-β structure-binding molecule, such as a finger domain or a molecule containing one or more finger domains, or is a peptidomimetic analog of one or more finger domains. The compound can also be an antibody or a functional fragment thereof directed to the cross-β structure.

According to the invention, the compound or means for binding the cross-β structure may also be a multiligand receptor or fragment thereof. The compound may be, e.g., RAGE, CD36, Low density lipoprotein Related Protein (LRP), Scavenger Receptor B-1 (SR-B 1), SR-A, or a fragment of one of these proteins.

The finger domains, finger-containing molecules or antibodies may be human, mouse, rat or from any other species.

According to the invention, amino acids of the respective proteins may be replaced by other amino acids which may increase/decrease the affinity, the potency, bioavailability and/or half-life of the peptide. Alterations include conventional replacements (acid-acid, bulky-bulky and the like), introducing D-amino acids, making peptides cyclic, etc.

Further, the invention discloses compounds and methods:
1) for detecting the presence of the cross-β structure;
2) for inhibiting the formation of amyloid fibers;
3) for modulating cross-β structure-induced toxicity; and
4) for the removal of cross-β structure-containing molecules from the circulation.

This invention also discloses methods for preparing an assay to measure cross-β structure in sample solutions.

This invention also discloses methods for detecting cross-β structure in tissue samples or other samples obtained from living cells or animals.

This invention further discloses compounds and methods for preparing a composition for inhibiting cross-β structure fibers formation.

This invention still further discloses compounds and methods for preparing a composition for modulating cross-β structure-induced toxicity.

Abbreviations: Aβ, beta-amyloid peptide; AD, Alzheimer disease; AGE, advanced glycation end-products; CpB, carboxypeptidase B; COI (carboxypeptidase inhibitor); ELISA, enzyme-linked immunosorbent assay (ELISA); FN, fibronectin; F, finger or fibronectin type I domain; FXII, factor XII (Hageman factor); HGFa, hepatocyte growth factor activator; IAPP, islet amyloid polypeptide; PCR, polymerase chain reactions (PCR); RAGE, receptor for AGE; tPA, tissue-type plasminogen activator.

The invention discloses compounds and methods for the detection and treatment of diseases associated with the excessive formation of cross-β structure.

The cross-β structure can be part of an Aβ fibers or part of another amyloid fiber. The cross-β structure can also be present in denatured proteins.

The invention discloses methods to detect the cross-β structure. In one embodiment, a cross-β structure-binding compound or means for binding the cross-β structure such as a finger domain or a molecule comprising one or more finger modules, is bound or affixed to a solid surface, such as a microtiter plate. The solid surfaces useful in this embodiment would be known to one of skill in the art. For example, one embodiment of a solid surface is a bead, a column, a plastic dish, a plastic plate, a microscope slide, a nylon membrane, etc. After blocking, the surface is incubated with a sample.

After removal of an unbound sample, bound molecules comprising the cross-β structure are subsequently detected using a second cross-β structure-binding compound, such as an anti-cross-β structure antibody or a molecule containing a finger module. The second cross-β structure compound is bound to a label such as an enzyme, i.e., peroxidase. The detectable label may also be a fluorescent label, a biotin, a digoxigenin, a radioactive atom, a paramagnetic ion, and a chemiluminescent label. It may also be labeled by covalent means such as chemical, enzymatic or other appropriate means with a moiety such as an enzyme or radioisotope. Portions of the above-mentioned compounds of the invention may be labeled by association with a detectable marker substance (e.g., radiolabeled with $^{125}I$ or biotinylated) to provide reagents useful in detection and quantification of a compound or its receptor-bearing cells or its derivatives in solid tissue, and fluid samples such as blood, cerebral spinal fluid, urine or others. Such samples may also include serum used for tissue culture or medium used for tissue culture.

In another embodiment, the solid surface can be microspheres, for example, for agglutination tests.

In one embodiment, the compound containing a finger module is used to stain tissue samples. In one aspect, the compound or means for binding the cross-β structure is fused to a protein or peptide, such as glutathion-S-transferase. Alternatively, the compound is coupled to a label. The detectable label may be a fluorescent label, a biotin, a digoxigenin, a radioactive atom, a paramagnetic ion, or a chemiluminescent label. It may also be labeled by covalent means such as chemical, enzymatic or other appropriate means with a moiety such as an enzyme or radioisotope. Portions of the above-mentioned compounds of the invention may be labeled by association with a detectable marker substance (e.g., radiolabeled with $^{125}I$, $^{99m}Tc$, $^{131}I$, chelated radiolabels, or biotinylated) to provide reagents useful in detection and quantification of a compound or its receptor-bearing cells or its derivatives in solid tissue, and fluid samples such as blood, cerebral spinal fluid or urine. The compound or means for binding the cross-β structure is incubated with the sample and after washing, is visualized with antibodies directed against the fused protein or polypeptide, such as glutathion-S-transferase.

In an embodiment, the sample is tissue from patients with or expected to suffer from a conformational disease. Alternatively, the tissue is derived from animals or from cells cultured in vitro.

The methods of the invention disclose a new diagnostic tool. It was not until the present invention that a universal β-structure epitope was disclosed and that a diagnostic assay could be based on the presence of the cross-β structure. Such use is particularly useful for diagnostic identification of conformational diseases or diseases associated with amyloid formation, such as Alzheimer or diabetes. It is clear that this diagnostic use is also useful for other diseases which involve cross-β structure formation, like all amyloidosis-type diseases, atherosclerosis, diabetes, bleeding, cancer, sepsis and other inflammatory diseases, Multiple Sclerosis, auto-immune diseases, disease associated with loss of memory or Parkinson and other neuronal diseases (epilepsy). For example, one can use a finger domain (of, for example, tPA) and provide it with a label (radioactive, fluorescent, etc.). This labeled finger domain may be used either in vitro or in vivo for the detection of cross-β structure-comprising proteins, hence, for determining the presence of a plaque involved in a conformational disease. One can use, for example, an ELISA assay to determine the amount of sepsis in a patient or one can localize a plaque involved in a conformational disease.

In another embodiment, this invention discloses a method for inhibiting the formation of amyloid fibers or to modulate cross-β structure-induced toxicity. The compound is a cross-β-binding module, such as a finger domain, a finger domain-containing molecule, a peptidomimetic analog, and/or an anti-cross-β structure antibody, and/or a multiligand receptor or a fragment thereof.

According to the invention, the inhibition of fiber formation has the consequence of decreasing the load of fibers.

The inhibition of fiber formation or modulating cross-β structure toxicity may also have the consequence of modulating cell death. The cell can be any cell, but may be a neuronal cell, an endothelial cell, or a tumor cell. The cell can be a human cell or a cell from any other species.

The cell may typically be present in a subject. The subject to which the compound is administered may be a mammal or a human.

The subject may be suffering from amyloidosis, from another conformational disease, from prion disease, from chronic renal failure and/or dialysis-related amyloidosis, from atherosclerosis, from cardiovascular disease, from autoimmune disease, or the subject may be obese. The subject may also be suffering from inflammation, rheumatoid arthritis, diabetes, retinopathy, sepsis, diffuse intravascular coagulation, hemolytic uremic syndrome, and/or preeclampsia. The diseases which may be treated or prevented with the methods of the present invention include, but are not limited to, diabetes, Alzheimer disease, senility, renal failure, hyperlipidemic atherosclerosis, neuronal cytotoxicity, Down's syndrome, dementia associated with head trauma, amyotrophic lateral sclerosis, multiple sclerosis, amyloidosis, an autoimmune disease, inflammation, a tumor, cancer, male impotence, wound healing, periodontal disease, neuropathy, retinopathy, nephropathy or neuronal degeneration.

The administration of compounds according to the invention may be constant or for a certain period of time. The compound may be delivered hourly, daily, weekly, monthly (e.g., in a time release form) or as a one time delivery. The delivery may also be continuous, e.g., intravenous delivery.

A carrier may also be used to deliver the compound to a subject. The carrier may be a diluent, an aerosol, an aqueous solution, a non-aqueous solution, or a solid carrier. This invention also discloses pharmaceutical compositions including therapeutically effective amounts of polypeptide compositions and compounds, together with suitable diluents, preservatives, solubilizers, emulsifiers, adjuvants and/or carriers. Such compositions may be liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), antioxidants (e.g., ascorbic acid, sodium metabisulfite), preservatives (e.g., Thimerosal benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, microemulsions, micelles, uni-lamellar or multi-lamellar vesicles, erythrocyte ghosts, or spheroplasts.

The administration of compounds according to the invention may comprise intralesional, intraperitoneal, intramuscular or intravenous injection; infusion; liposome-mediated delivery; topical, intrathecal, gingival pocket, per rectum, intrabronchial, nasal, oral, ocular or otic delivery. In a further embodiment, the administration includes intrabronchial administration, anal, intrathecal administration or transdermal delivery.

According to the invention, the compounds may be administered hourly, daily, weekly, monthly or annually. In another embodiment, the effective amount of the compound comprises from about 0.000001 mg/kg body weight to about 100 mg/kg body weight.

The compounds according to the invention may be delivered locally via a capsule which allows sustained release of the agent over a period of time. Controlled or sustained release compositions include formulation in lipophilic depots (e.g., fatty acids, waxes, oils). Also included in the invention are particulate compositions coated with polymers (e.g., poloxamers or poloxalenes) and the agent coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and/or oral.

The effective amount of the compounds according to the invention may comprise 1 ng/kg body weight to about 1 gr/kg body weight. The actual effective amount will be based upon the size of the compound and its properties.

The activity of tPA and/or the tPA-mediated activation of plasminogen is increased by the binding to fibrin fragments or other protein fragments that have a lysine or an arginine at the carboxy-terminal end. B-type carboxypeptidases including, but not limited to, carboxypeptidase B (CpB) or Thrombin Activatable Fibrinolysis Inhibitor (TAFI, also named carboxypeptidase U or carboxypeptidase R), are enzymes that cleave off carboxy-terminal lysine and arginine residues of fibrin fragments that would otherwise bind to tPA and/or plasminogen and stimulate plasmin formation.

Because this invention has made clear that the cross-β structures are harmful when present in certain parts of the body like, for example, the brain and the damage is effected by the combination of cross-β structures with tPA, a method is disclosed to inhibit cross-β structure-mediated effects comprising providing an effective amount of a protein comprising a finger domain to block the binding sites of the cross-β structure for tPA. The cross-β structure-mediated effects may even be further diminished comprising providing an effective amount of B-type carboxypeptidase activity to inhibit the tPA activity.

The invention discloses the use of a compound capable of binding to a cross-β structure for the removal of cross-β structures. The compound or means for binding the cross-β structure is a cross-β-binding molecule, such a protein and/or a functional equivalent and/or a functional fragment thereof. In another aspect, the compound comprises a finger domain or a finger domain-containing molecule or a functional equivalent or a functional fragment thereof. In yet another aspect, the finger domain is derived from fibronectin, FXII, HGFa or tPA. It is clear that the invention also comprises antibodies that bind cross-β structures. In another embodiment, the protein is an antibody and/or a functional equivalent and/or a functional fragment thereof. With this use, the invention discloses, for example, a therapeutic method to remove cross-β structure-comprising proteins from, for example, the circulation, such as via extracorporeal dialysis. For example, a patient with sepsis is subjected to such use by dialysis of blood of the patient through means which are provided with, for example, immobilized finger domains. One could, for example, couple the finger domains to a solid surface or to the inside of the tubes used for dialysis. In this way, all cross-β structure-comprising proteins will be removed from the bloodstream of the patient, thus, relieving the patient of the negative effects caused by the cross-β structure-comprising proteins. Besides finger domain-comprising compounds, it is also possible to use other cross-β structure-binding compounds, like antibodies or soluble multiligand receptors. It is also clear that the use could be applied in hemodialysis of kidney patients.

As used herein, "finger" encompasses a sequence that fulfills the criteria outlined in FIG. 14. The sequence encompasses approximately 50 amino acids, containing four cysteine residues at distinct spacing. In one aspect, the finger domains of tPA, FXII, HGFa or fibronectin are used (SEQ ID NOs: 3-17). Alternatively, the "finger" may be a polypeptide analog or peptidomimetic with similar function, e.g., by having three-dimensional conformation. It is feasible that such analogs have improved properties.

EXAMPLES

Example 1

Reagents

Bovine serum albumin (BSA) fraction V pH 7.0 and D-glucose-6-phosphate di-sodium (g6p), D, L-glyceraldehyde, and chicken egg-white lysozyme were from ICN (Aurora, Ohio, USA). Rabbit anti-recombinant tissue-type plasminogen activator (tPA) 385R and mouse anti-recombinant tPA 374B were purchased from American Diagnostica (Veenendaal, The Netherlands). Anti-laminin (L9393) was from Sigma. Swine anti-rabbit immunoglobulins/HRP (SWARPO) and rabbit anti-mouse immunoglobulins/HRP (RAMPO) were from DAKO Diagnostics B.V. (The Netherlands). Alteplase (recombinant tissue-type plasminogen activator, tPA) was obtained from Boehringer-Ingelheim (Germany). Reteplase (Rapilysin), a recombinant mutant tPA containing only kringle 2 and the catalytic domain (K2P-tPA) was obtained from Roche, Hertfordshire, UK, and porcine pancreas carboxypeptidase B (CpB) was from Roche, Mannheim, Germany. Carboxypeptidase inhibitor (CPI) was from Calbiochem (La Jolla, Calif., USA). Tween 20 was purchased from Merck-Schuchardt (Hohenbrunn, Germany). Congo red was obtained from Aldrich (Milwaukee, Wis., USA). Thioflavin T and lyophilized human hemoglobin (Hb) were from Sigma (St. Louis, Mo., USA). Lyophilized human fibrinogen was from Kordia (Leiden, The Netherlands). Chromogenic plasmin substrate S-2251 was purchased from Chromogenix (Milan, Italy). Oligonucleotides were purchased from Sigma-Genosys (U.K.). Boro glass capillaries (0.5 mm Ø) were from Mueller (Berlin, Germany).

Example 2

Synthetic Peptides

Peptide Aβ (1-40), containing amino acids as present in the described human Alzheimer peptide (DAEFRHDSGYEVH-HQKLVFFAEDVGSNKGAIIGLMVGGVV) (SEQ ID NO: 18), fibrin peptides 85 (or FP13) (KRLEVDIDIKIRS) (SEQ ID NO: 19), 86 (or FP12) (KRLEVDIDIKIR) (SEQ ID NO: 20) and 87 (or FP10) (KRLEVDIDIK) (SEQ ID NO: 21), derived from the sequence of human fibrin(ogen) and the islet amyloid polypeptide (IAPP) peptide or derivatives (fl-hIAPP: KCNTATCATQRLANFLVHSSNNFGAILSSTNVGSNTY (SEQ ID NO: 22), ΔhIAPP(SNNFGAILSS) (SEQ ID NO:23), ΔmIAPP (SNNLGPVLPP) (SEQ ID NO: 24) were obtained from Pepscan, Inc. (The Netherlands) or from the peptide synthesis facility at the Netherlands Cancer Institute (NCI, Amsterdam, The Netherlands). The peptides were dissolved in phosphate buffered saline (PBS) to a final concentration of 1 mg ml$^{-1}$ and stored for three weeks at room temperature (RT) to allow formation of fibers. During this period, the suspension was vortexed twice weekly. After three weeks, the suspension was stored at 4° C. Freeze-dried Aβ (1-40) from the NCI allowed to form cross-β structure in the same way. Cross-β structure formation was followed in time by examination of Congo red binding and green birefringence under polarized light.

Example 3

Congo Red Binding and Thioflavin T Fluorescence of a Fibrin Clot

For Thioflavin T-fluorescence measurements, 1 mg ml$^{-1}$ of fibrinogen was incubated at 37° C. with 2 U ml$^{-1}$ of factor IIa in 150 mM NaCl, 20 mM Tris-HCl pH 7.5, 10 mM CaCl$_2$, 50 μM Thioflavin T. Background fluorescence of a clot was recorded in the absence of Thioflavin T and background Thioflavin T fluorescence was measured in the absence of factor IIa. Fluorescence was measured on a Hitachi F-4500 fluorescence spectrophotometer (Ltd., Tokyo, Japan), using Sarstedt REF67.754 cuvettes. Apparatus settings: excitation at 435 nm (slit 10 nm), emission at 485 nm (slit 10 nm), PMT voltage 950 V, measuring time 10 seconds, delay 0 seconds. For detection of Congo red binding, a fibrin clot was formed at room temperature as described above (Thioflavin T was omitted in the buffer). The clot was incubated with Congo red solution and washed according to the manufacturer's recommendations (Sigma Diagnostics, MO, USA). The clot was analyzed under polarized light.

Example 4

Initial Preparation of Glycated Albumin, Hemoglobin (Hb) and Lysozyme

For preparation of advanced glycation end-product modified bovine serum albumin (albumin-g6p), 100 mg ml$^{-1}$ of albumin was incubated with PBS containing 1 M of g6p and 0.05% m/v NaN$_3$, at 37° C. in the dark. One albumin solution was glycated for two weeks, a different batch of albumin— was glycated for four weeks. Glycation was prolonged up to 23 weeks with part of the latter batch. Human Hb at 5 mg ml$^{-1}$ was incubated for ten weeks at 37° C. with PBS containing 1 M of g6p and 0.05% m/v of NaN$_3$. In Addition, a Hb solution of 50 mg ml$^{-1}$ was incubated for eight weeks with the same buffer. For preparation of glyceraldehyde-modified albumin (albumin-glyceraldehyde) and chicken egg-white lysozyme (lysozyme-glyceraldehyde), filter-sterilized protein solutions of 15 mg ml$^{-1}$ were incubated for two weeks with PBS containing 10 mM of glyceraldehyde. In controls, g6p or glyceraldehyde was omitted in the solutions. After incubations, albumin and lysozyme solutions were extensively dialyzed against distilled water and subsequently stored at −20° C. Protein concentrations were determined with Advanced protein-assay reagent ADV01 (Cytoskeleton, Denver, Colo., USA). Glycation was confirmed by measuring intrinsic-fluorescent signals from advanced glycation end-products; excitation wavelength 380 nm, emission wavelength 435 nm.

Example 5

Further Experiment Involving Glycation

For preparation of albumin-AGE, 100 mg ml$^{-1}$ bovine serum albumin (fraction V, catalogue #A-7906, initial fractionation by heat shock, purity $\geq$98% (electrophoresis), remainder mostly globulins, Sigma-Aldrich, St. Louis, Mo., USA) was incubated at 37° C. in the dark, with phosphate-buffered saline (PBS, 140 mM sodium chloride, 2.7 mM potassium chloride, 10 mM disodium hydrogen phosphate, 1.8 mM potassium di-hydrogen phosphate, pH 7.3), 1 M D-glucose-6-phosphate disodium salt hydrate (anhydrous) (ICN, Aurora, Ohio, USA) and 0.055% (m/v) NaN$_3$. Bovine albumin has 83 potential glycation sites (59 lysine and 23 arginine residues, N-terminus). Albumin was glycated for two weeks (albumin-AGE:2), four weeks (albumin-AGE:4) or 23 weeks (albumin-AGE:23). In controls, g6p was omitted. After incubation, solutions were extensively dialyzed against distilled water and subsequently stored at 4° C. Protein concentrations were determined with advanced protein-assay reagent ADV01 (Cytoskeleton, CO, USA). Alternatively, albumin was incubated for 86 weeks with 1 M g6p, 250 mM DL-glyceraldehyde (ICN, Aurora, Ohio, USA)/100 mM NaCNBH$_3$, 1 M β-D-(−)-fructose (ICN, Aurora, Ohio, USA), 1 M D(+)-glucose (BDH, Poole, England), 500 mM glyoxylic acid monohydrate (ICN, Aurora, Ohio, USA)/100 mM NaCNBH$_3$, and corresponding PBS and PBS/NaCNBH$_3$ buffer controls. Glycation was confirmed (i) by observation of intense brown staining, (ii) by the presence of multimers on SDS-polyacrylamide gels, (iii) by assaying binding of AGE-specific antibodies moab anti-albumin-g6p 4B5[46] and poab anti-fibronectin-g6p (Ph. De Groot/I. Bobbink, UMC Utrecht; unpublished data), and (iv) by measuring intrinsic fluorescent signals from AGE (excitation wavelength 380 nm, emission wavelength 445 nm). Autofluorescent signals of albumin controls were less than 4% of the signals measured for albumin-AGE and were used for background corrections.

Example 6

Isolation of Hb from Human Erythrocytes

Human Hb was isolated from erythrocytes in EDTA-anticoagulated blood of three healthy individuals and of 16 diabetic patients. 100 μl of whole blood was diluted in 5 ml of physiological salt (154 mM NaCl), cells were gently spun down, and resuspended in 5 ml of physiological salt. After 16 hours incubation at room temperature, cells were again spun down. Pelleted cells were lysed by adding 2 ml of 0.1 M of boric acid, pH 6.5 and subsequently, cell debris was spun down. Supernatant was collected and stored at −20° C.

Example 7

Determination of GlycoHb Concentrations

Concentrations of glycated Hb, also named glycohemoglobin, or named Hb$_{A1c}$, in EDTA-blood of human healthy donors or diabetic patients, were determined using a turbidimetric inhibition immunoassay with hemolyzed whole blood, according to the manufacturer's recommendations (Roche Diagnostics, Mannheim, Germany). Standard deviations are 2.3% of the measured Hb$_{A1c}$ concentrations.

Example 8

Binding of Congo Red to Glycated Albumin

Binding of Congo red to albumin-AGE glycated for 86 weeks with carbohydrates glucose, fructose and glucose-6-phosphate, or with carbohydrate derivatives glyceraldehyde and glyoxylic acid, was tested using air-dried samples. For this purpose, 5 μg albumin was applied to a glass cover slip and air dried. Samples were incubated with Congo red and subsequently washed according to the manufacturer's recommendations (Sigma Diagnostics, St Louis, Mo., USA). Pictures were taken on a Leica DMIRBE fluorescence microscope (Rijswijk, The Netherlands) using 596 nm and 620 nm excitation and emission wavelengths, respectively.

Example 9

Endostatin Preparations

Endostatin was purified from *Escherichia coli* essentially as described.[47] In short, Bl21.DE3 bacteria expressing endostatin were lysed in a buffer containing 8 M urea, 10 mM Tris (pH 8.0), 10 mM imidazole and 10 mM β-mercaptoethanol. Following purification over Ni$^{2+}$-agarose, the protein sample was extensively dialyzed against H$_2$O. During dialysis, endostatin precipitates as a fine white solid. Aliquots of this material were either stored at −80° C. for later use, or were freeze-dried prior to storage. Soluble endostatin produced in the yeast strain *Pichia pastoris* was kindly provided by Dr. Kim Lee Sim (EntreMed, Inc., Rockville, Mass., USA). Aggregated endostatin was prepared from soluble endostatin as follows. Soluble yeast endostatin was dialyzed overnight in 8 M urea and subsequently three times against H$_2$O. Like bacterial endostatin, yeast endostatin precipitates as a fine white solid.

Example 10

Congo Red Staining

Freeze-dried bacterial endostatin was resuspended in either 0.1% formic acid (FA) or in dimethyl-sulfoxide and taken up in a glass capillary. The solvent was allowed to evaporate and the resulting endostatin material was stained with Congo red according to the manufacturer's protocol (Sigma Diagnostics, St. Louis, Mo., USA).

Example 11

Circular Dichroism Measurements

UV circular dichroism (CD) spectra of peptide and protein solutions (100 μml$^{-1}$ in H$_2$O) were measured on a JASCO J-810 CD spectropolarimeter (Tokyo, Japan). Averaged absorption spectra of five or ten single measurements from 190-240 nm or from 190-250 nm, for fibrin peptides 85, 86, 87 or for albumin, glycated albumin and human Aβ (16-22), respectively, are recorded. The CD spectrum of Aβ (16-22) was measured as a positive control. Aβ (16-22) readily adopts amyloid fiber conformation with cross-β structure when incubated in H$_2$O[45]. For albumin and Aβ (16-22), relative percentage of the secondary structure elements present was estimated using k2d software.[48]

Example 12

X-Ray Fiber Diffraction

Aggregated Endostatin was Solubilized in 0.1% FA, Lyophilized Fibrin Peptides were dissolved in $H_2O$ and glycated albumin was extensively dialyzed against water. Samples were taken up in a glass capillary. The solvent was allowed to evaporate over a period of several days. Capillaries containing the dried samples were placed on a Nonius kappaCCD diffractometer (Bruker-Nonius, Delft, The Netherlands). Scattering was measured using sealed tube MoK$\alpha$ radiation with a graphite monochromator on the CCD area detector during 16 hours. Scattering from air and the glass capillary wall were subtracted using in-house software (VIEW/EVAL, Dept. of Crystal- and Structural Chemistry, Utrecht University, The Netherlands).

Example 13

Transmission Electron Microscopy

Endostatin, hemoglobin and albumin samples were applied to 400 mesh specimen grids covered with carbon-coated collodion films. After five minutes, the drops were removed with filter paper and the preparations were stained with 1% methylcellulose and 1% uranyl acetate. After washing in $H_2O$, the samples were dehydrated in a graded series of EtOH and hexanethyldisilazane. Transmission electron microscopy (TEM) images were recorded at 60 kV on a JEM-1200EX electron microscope (JEOL, Japan).

Example 14

Enzyme-Linked Immunosorbent Assay: Binding of tPA to Glycated Albumin, Hb and A$\beta$(1-40)

Binding of tPA to albumin-g6p (four-week and 23-week incubations), albumin-glyceraldehyde, control albumin, human Hb-g6p (ten-week incubation), Hb control, or to A$\beta$ (1-40) was tested using an enzyme-linked immunosorbent assay (ELISA) set-up. Albumin-g6p and control albumin (2.5 µg ml$^{-1}$ in coat buffer, 50 mM $Na_2CO_3$/$NaHCO_3$ pH 9.6, 0.02% m/v $NaN_3$, 50 µl/well) were immobilized for one hour at room temperature in 96-well protein Immobilizer plates (Exiqon, Vedbaek, Denmark). A$\beta$ (1-40) (10 µg ml$^{-1}$ in coat buffer) was immobilized for 75 minutes at room temperature in a 96-well peptide Immobilizer plate (Exiqon, Vedbaek, Denmark). Control wells were incubated with coat buffer only. After a wash step with 200 µl of PBS/0.1% v/v Tween 20, plates were blocked with 300 µl of PBS/1% v/v Tween 20, for two hours at room temperature while shaking. All subsequent incubations were performed in PBS/0.1% v/v Tween 20 for one hour at room temperature while shaking, with volumes of 50 µl per well. After each incubation, wells were washed five times with 200 µl of PBS/0.1% v/v Tween 20. Increasing amounts of f.l. tPA or K2-P tPA was added in triplicate to coated wells and to control wells. Antibody 385R and subsequently SWARPO, or antibody 374B and subsequently RAMPO, were added to the wells at a concentration of 1 µg ml$^{-1}$. Bound peroxidase-labeled antibody was visualized using 100 µl of a solution containing 8 mg ortho-phenylene-diamine and 0.0175% v/v of $H_2O_2$ in 20 ml of 50 mM citric acid/100 mM $Na_2HPO_4$ pH 50. Staining was stopped upon adding 50 µl of a 2-M $H_2SO_4$ solution. Absorbance was read at 490 nm on a $V_{max}$ kinetic microplate reader (Molecular Devices, Sunnyvale, Calif., USA).

Competition experiments were performed with 20 or 40 nM of tPA with, respectively, albumin-g6p or A$\beta$ (1-40) and with increasing amounts of Congo red in PBS/0.08% v/v Tween 20/2% v/v EtOH.

Example 15

ELISA: Binding of tPA to Albumin-AGE

Binding of the cross-β structure marker tPA to albumin-AGE was tested using an ELISA setup. We showed that tPA binds to prototype amyloid peptides human A$\beta$ (140) and human IAPP[49] (this application). Therefore, we used tPA binding to these two peptides as positive control. The 86-week glycated samples and controls were coated to Greiner microlon plates (catalogue #655092, Greiner, Frickenhausen, Germany). Wells were blocked with Superblock (Pierce, Rockford, Ill., USA). All subsequent incubations were performed in PBS/0.1% (v/v) Tween 20 for one hour at room temperature while shaking, with volumes of 50 µl per well. After incubation, wells were washed five times with 300 µl PBS/0.1% (v/v) Tween 20. Increasing concentrations of tPA were added in triplicate to coated wells as well as to control wells. During tPA incubations of 86-week incubated samples, at least a 123,000 times molar excess of ∈-amino caproic acid (∈ACA, 10 mM) was added to the solutions. ∈ACA is a lysine analogue and is used to avoid potential binding of tPA to albumin via its kringle 2 domain.[50] Monoclonal antibody 374b (American Diagnostica, Instrumentation laboratory, Breda, The Netherlands) and, subsequently, RAMPO (Dako diagnostics, Glostrup, Denmark) was added to the wells at a concentration of 0.3 µg ml$^{-1}$. Bound peroxidase-labeled antibody was visualized using 100 µl of a solution containing 8 mg ortho-phenylene-diamine in 20 ml 50 mM citric acid/100 mM $Na_2HPO_4$ pH 5.0 with 0.0175% (v/v) $H_2O_2$. Staining was stopped upon adding 50 µl of a 2 M $H_2SO_4$ solution. Absorbance was read at 490 nm on a $V_{max}$ kinetic microplate reader (Molecular Devices, CA, USA). Background signals from non-coated control wells were substracted from corresponding coated wells.

Example 16

Thioflavin T Fluorescence of Glycated Albumin and Lysozyme, and tPA

Initially, for fluorescence measurements, 500 nM of albumin-g6p, albumin-glyceraldehyde, control albumin, lysozyme-glyceraldehyde, or control lysozyme were incubated with increasing amounts of Thioflavin T, in 50 mM of glycine-NaOH, pH 9. For blank readings, an identical Thioflavin T dilution range was prepared without protein or Thioflavin T was omitted in the protein solutions. Samples were prepared in triplicate.

Example 17

Thioflavin T Fluorescence

In further experiments, fluorescence measurements with albumin-g6p:2, albumin-g6p:4, albumin-g6p:23 and controls in 50 mM glycine-NaOH, pH 9 were incubated with increasing amounts of ThT (Sigma-Aldrich Chemie, Steinheim, Germany), a marker for amyloid cross-β structure.[51] Albumin-AGE:4 concentration was 175 nM; other protein concentrations were 500 nM. For fluorescence measurements with 86-week glycated samples, 140 nM of protein was incubated with a fixed concentration of 20 µM ThT. Fluorescence was measured in triplicate on a Hitachi F-4500 fluorescence spectrophotometer (Ltd., Tokyo, Japan), after one hour incubation at room temperature. Excitation and emission wavelengths were 435 nm (slit 10 nm) and 485 nm (slit 10 nm), respectively. Background signals from buffer and protein solutions without ThT were substracted from corresponding measurements with protein solution incubated with ThT.

Example 18

Fluorescence: Competitive Binding of Thioflavin T and tPA to Albumin-g6p

A solution of 430 nM albumin-g6p and 19 µM of Thioflavin T was incubated with increasing amounts of tPA, for one hour at room temperature. For blank readings, albumin-g6p was omitted. Samples were prepared in four-fold in 50 mM glycine-NaOH pH 9. Emission measurements were performed as described above.

Example 19

Absorbance: Competitive Binding of Thioflavin T and tPA to Albumin-g6p

Albumin-g6p (500 nM) and Thioflavin T (10 µM) were incubated with increasing amounts of tPA, in 50 mM glycine-NaOH pH 9, for one hour at room temperature. Absorbance measurements were performed at the albumin-g6p Thioflavin T absorbance maximum at 420 nm. Samples were prepared in four-fold. For blank readings, albumin-g6p was omitted in the solutions. Absorbance was read in a quartz cuvette on a Pharmacia Biotech Ultrospec 3000 UV/visible spectrophotometer (Cambridge, England).

Example 20

Plasminogen Activation Assay

Plasminogen (200 µg ml$^{-1}$) was incubated with tPA (200 pM) in the presence or the absence of a co-factor (5 µM of either endostatin, Aβ (1-40), or one the fibrin-derived peptides 85, 86 and 87). At the indicated time intervals, samples were taken and the reaction was stopped in a buffer containing 5 mM EDTA and 150 mM εACA. After collection of the samples, a chromogenic plasmin substrate S-2251 was added and plasmin activity was determined kinetically in a spectrophotometer at 37° C.

Example 21

N1E-115 Cell Culture and Differentiation

N1E-115 mouse neuroblastoma cells were routinely cultured in DMEM containing 5% FCS, supplemented with antibiotics. Cells were differentiated into post-mitotic neurons.[52] The cells were exposed to Aβ (50 µg ml$^{-1}$) for 24 hours in the presence or absence of 20 µg ml$^{-1}$ plasminogen in the presence or absence of 50 µg ml$^{-1}$ CpB. Cells were photographed, counted and lysed by the addition of 4× sample buffer (250 mM Tris pH 6.8, 8% SDS, 10% glycerol, 100 mM DTT, 0.01% w/v bromophenol blue) to the medium. The lysate, containing both adherent and floating (presumably dying and/or dead) cells, as well as the culture medium, were analyzed for the presence of plasminogen and plasmin, as well as for laminin, by Western blot analysis using specific antibodies against plasminogen (MoAb 3642, American Diagnostics), laminin (PoAb L9393, Sigma).

Example 22

Binding of Human Factor XII to Amyloid Peptides and Proteins that Contain the Cross-β Structure Fold The binding of human FXII (Calbiochem, La Jolla, Calif., USA, catalogue #233490) to amyloid (poly)peptides was tested. Prototype amyloid peptides human amyloid-β (1-40) (hAβ (1-40)) and human fibrin fragment $α_{147-159}$ FP13, and glucose-6-phosphate glycated bovine albumin (albumin-advanced glycation end product (AGE)) and glucose-6-phosphate glycated human hemoglobin (Hb-AGE), all containing cross-β structure, as well as negative controls mouse A islet amyloid polypeptide (ΔmIAPP), albumin-control and Hb-control, all three lacking the amyloid-specific structure, were coated to ELISA plates and overlayed with a concentration series of human factor XII. Binding of FXII was detected using a rabbit polyclonal anti-FXII antibody (Calbiochem, La Jolla, Calif., USA, catalogue #233504) and peroxidase-labeled swine anti-rabbit IgG. Wells were coated in triplicate. The FXII binding buffer included 10 mM HEPES pH 7.3, 137 mM NaCl, 11 mM D-glucose, 4 mM KCl, 1 mg ml$^{-1}$ albumin, 50 µM $ZnCl_2$, 0.02% (m/v) $NaN_3$ and 10 mM ε-amino caproic acid (εACA). Lysine analogue εACA was added to avoid putative binding of FXII to cross-β structure via the FXII kringle domain. In addition, binding of FXII to hAβ (1-40) and the prototype amyloid human amylin fragment hΔIAPP was tested using dot blot analysis. 10 µg of the peptides that contain cross-β structure, as well as the negative control peptide mΔIAPP and phosphate-buffered saline (PBS) were spotted in duplicate onto methanol-activated nitrocellulose. Spots were subsequently incubated with 2 nM FXII in FXII buffer or with FXII buffer alone, anti-FXII antibody, and SWARPO. Binding of FXII was visualized by chemiluminescence upon incubation with enhanced luminol reagent (PerkinElmer Life Sciences, Boston, Mass., USA). To test whether FXII and tPA, which is known for its capacity to bind to polypeptides that contain the cross-β structure fold,[49] bind to overlapping binding sites on amyloid (poly)peptides, competitive ELISAs were performed. Coated hAβ (1-40) or amyloid albumin-AGE were incubated with 2.5 nM or 15 nM FXII in binding buffer in the presence of a concentration series of human recombinant tissue-type plasminogen activator (ACTILYSE®, full-length tPA) or RETEPLASE® (K2P-tPA). RETEPLASE® is a truncated form of tPA that includes the second kringle domain and the protease domain. The f.l. tPA and K2P-tPA concentration was at maximum 135 times the $k_D$ for tPA binding to hAβ (1-40) (50 nM) or 150 times the $k_D$ for tPA binding to albumin-AGE (1 nM).

Example 23

Cloning Procedure

Cloning of the amino-terminal finger domain (F) of human tPA, residues Ser1-Ser50, preceded by the pro-peptide (residues Met-35-Arg-1) and a BglII restriction site, was performed by using PCR and standard recombinant DNA techniques. In brief, the pro-peptide finger region was amplified by PCR using 1 ng of plasmin Zp17,[53] containing the cDNA encoding tPA as a template. Oligonucleotides used were 5'AAAAGTCGACAGCCGCCACCATGGATGCAATGA-AGAGA (SEQ ID NO: 25) (1) and 3'AAAAGCGGCCGC- CCACTTTTGACAGGCACTGAG (SEQ ID NO: 26) (2) comprising a SalI or a NotI restriction site, respectively (underlined). The PCR product was cloned in a SalI/NotI-digested expression vector, pMT2-GST.[54] As a result, a construct is generated that contains a SalI restriction site, the coding sequence for the finger domain of tPA, a NotI and a KpnI restriction site, a thrombin cleavage-site (TCS), a glutathion-S-transferase (GST) tag and an EcoRI restriction site. The appropriate sequence of the construct was confirmed by sequence analysis. In a similar way, a construct consisting of the tPA F-EGF domains was prepared. Next, the constructs were ligated SalI-EcoRI in pGEM3Zf(−) (Promega, Madison, Wis., USA). The HindIII-SalI-tPA pro-peptide-BglII-F-NotI-KpnI-TCS-GST-EcoRI construct was used as a cloning cassette for preparation of constructs containing tPA K1, F-EGF-K1, EGF, as well as human hepatocyte growth factor activator F and F-EGF, human factor XII F and F-EGF, and human fibronectin F4, F5, F4-5 and F10-12. Subsequently, constructs were ligated HindIII-EcoRI in the pcDNA3 expression vector (Invitrogen, Breda, The Netherlands). In addition, the GST tag alone was cloned into pcDNA3, preceded by the tPA pro-peptide. Primers used for constructs were:

Example 24

Transient Expression of tPA-F-GST in 293T Cells

Initially, 293T cells were grown in RPMI1640 medium (Invitrogen, Scotland, U.K.) supplemented with 5% v/v fetal calf-serum, penicillin, streptomycin and guanidine, to 15% confluency. Cells were transiently transfected using Fugene-6, according to the manufacturer's recommendations (Roche, Ind., USA). pMT2-tPA-F-GST containing the tPA fragment, or a control plasmid, pMT2-RPTPµ-GST, containing the extracellular domain of receptor-like protein tyrosine phosphatase µ (RPTPµ)[54] were transfected, and medium was harvested after 48 hours transfection. Expression of tPA-F-GST and RPTPµ-GST in 293T medium was verified by immunoblotting. Collected samples were run out on SDS-PAA gels after the addition of 2× sample buffer. Gels were blotted on nitrocellulose membranes. Membranes were blocked in 1% milk (Nutricia) and incubated with primary monoclonal anti-GST antibody 2F3[54] and secondary HRP-conjugated rabbit anti-mouse IgG (RAMPO). The blots were developed using Western Lightning Chemiluminescence Reagent Plus (Perkin Elmer Life Sciences, MA, USA).

```
tPA F-EGF
3'AAAAGCGGCCGCGTGGCCCTGGTATCTATTTC    (SEQ ID NO: 27)  (3) and (1)

PA EGF
5'AAAAGAGATCTGTGCCTGTCAAAAGTTGC        (SEQ ID NO: 28)  (4) and (2)

tPA K1
5'AAAAGAGATCTGATACCAGGGCCACGTGCTAC     (SEQ ID NO: 29)  (5)
3'AAAAGCGGCCGCCCGTCACTGTTTCCCTCAGAGCA  (SEQ ID NO: 30)  (6)

tPA F-EGF-K1
                                                        (1) and (6)

GST tag
(1)                                    (SEQ ID NO: 31)  (7)
and

AAAAGCGGCCGCCTGGCTCCTCTTCTGAATC

Fibronectin F4
5'TGCAAGATCTATAGCTGAGAAGTGTTTTGAT      (SEQ ID NO: 32)  (8)
3'GATGCGGCCGCCCTGTATTCCTAGAAGTGCAAGTG  (SEQ ID NO: 33)  (9)

Fibronectin F5
5'TGCAAGATCTACTTCTAGAAATAGATGCAAC      (SEQ ID NO: 34)  (10)
3'TGATGCGGCCGCCCCACAGAGGTGTGCCTCTC     (SEQ ID NO: 35)  (11)

Fibronectin F4-5
                                                        (8) and (11)

Fibronectin F10-12
5'AAAAAAGATCTAACCAACCTACGGATGACTC      (SEQ ID NO: 36)  (12)
3'AAAAAAGGTACCGACTGGGTTCACCCCCAGGT     (SEQ ID NO: 37)  (13)

factor XII F
5'GAAACAAGATCTCAGAAAGAGAAGTGCTTTGA     (SEQ ID NO: 38)  (14)
3'ACGGGCGGCCGCCCGGCCTGGCTGGCCAGCCGCT   (SEQ ID NO: 39)  (15)

factor XII F-EGF
5'AAAAAAGATCTCAGAAAGAGAAGTGCTTTGA      (SEQ ID NO: 40)  (16)
3'AAAAAGGTACCGGCTTGCCTTGGTGTCCACG      (SEQ ID NO: 41)  (17)

HGFa F
5'GCAAGAAGATCTGGCACAGAGAAATGCTTTGA     (SEQ ID NO: 42)  (18)
3'AAGGGCGGCCGCCCAGCTGTATGTCGGGTGCCTT   (SEQ ID NO: 43)  (19)

HGFa F-EGF
5'AAAAAGATCTGGCACAGAGAATGCTTTGA        (SEQ ID NO: 44)  (20)
3'AAAAAGGTACCGCTCATCAGGCTCGATGTTG      (SEQ ID NO: 45)  (21)
```

Example 25

Stable Expression of Finger Constructs in BHK Cells

Baby hamster kidney cells were seeded in DMEM/NUT mix F-12 (HAM) medium (Invitrogen, U.K.) supplemented with 5% v/v fetal calf-serum (FCS), penicillin, streptomycin and guanidine, to 1% confluency. Cells were stably transfected by using the $Ca_3(PO_4)_2$-DNA precipitation method. After 24 hours, medium was supplemented with 1 mg ml$^{-1}$ geneticin G-418 sulphate (Gibco, U.K.). Medium with G-418 was refreshed several times during ten days to remove dead cells. After this period of time, stable single colonies were transferred to new culture flasks and cells were grown to confluency. Expression of constructs was verified by immunoblotting. Collected samples were run out on SDS-PAA gels after the addition of 2× sample buffer. Gels were blotted on nitrocellulose membranes. Membranes were blocked in 5% milk (Nutricia) with 1.5% m/v BSA and incubated with primary monoclonal anti-GST antibody (Santa Cruz Biotechnology, Santa Cruz, Calif., USA, catalogue #Z-5), and secondary HRP-conjugated rabbit anti-mouse IgG (RAMPO). The blots were developed using Western Lightning Chemiluminescence Reagent Plus (PerkinElmer Life Sciences, MA, USA). Stable clones were grown in the presence of 250 µg ml$^{-1}$ G-418. For pull-down experiments, conditioned medium with 5% FCS of stable clones that produce constructs of interest was used. For purification purposes, cells of a stable clone of tPA F-EGF-GST were transferred to triple-layered culture flasks and grown in medium with 0.5% v/v Ultroser G (ITK Diagnostics, Uithoorn, The Netherlands). Medium was refreshed every three to four days. TPA F-EGF-GST was isolated from the medium on a Glutathione Sepharose 4B (Amersham Biosciences, Uppsala, Sweden) column and eluted with 100 mM reduced glutathione (Roche Diagnostics, Mannheim, Germany). Purity of the construct was checked with SDS-PAGE followed by Coomassie staining or Western blotting. From these analyses, it is clear that some GST is present in the preparation. Purified tPA F-EGF-GST was dialyzed against PBS and stored at −20° C.

Example 26

Purification of GST-Tagged tPA-F-GST and RPTPµ-GST

Medium was concentrated twenty-fold using Nanosep 10KΩ centrifugal devices (Pall Gelman Laboratory, MI, USA) and incubated with glutathione coupled to Sepharose 4B, according to the manufacturer's recommendations (Pharmacia Biotech, Uppsala, Sweden). Bound constructs were washed with PBS and eluted with 10 mM of glutathione in 50 mM Tris-HCl pH 8.0. Constructs were stored at −20° C., before use.

Example 27

Amyloid Pull-Down

Conditioned medium of BHK cells expressing GST-tagged tPA F, F-EGF, EGF, K1, F-EGF-K1, FXII F, HGFa F, Fn F4, Fn F5, Fn F4-5 and GST was used for amyloid binding assays. At first, constructs were adjusted to approximately equal concentration using Western blots. Qualitative binding of the recombinant fragments were evaluated using a "pull-down" assay. To this end, the recombinantly made fragments were incubated with either Aβ or IAPP fibrils. Since these peptides form insoluble fibers, unbound proteins can be easily removed from the fibers following centrifugation. The pellets containing the bound fragments were subsequently washed several times. Bound fragments were solubilized in SDS-sample buffer and analyzed by PAGE, as were unbound proteins in the supernatant fraction and starting material. The gels were analyzed using immunoblotting analysis with the anti-GST antibody Z-5.

Example 28

Amyloid ELISA with tPA F-EGF-GST

In order to define the affinity of the purified tPA F-EGF-GST recombinant protein, ELISAs were performed with immobilized amyloid (poly)peptides and non-amyloid control ΔmIAPP. Twenty-five µg ml$^{-1}$ of Aβ, FP13, IAPP or ΔmIAPP was immobilized on Exiqon peptide immobilizer plates. A concentration series of tPA F-EGF-GST in the presence of excess εACA was added to the wells and binding was assayed using anti-GST antibody Z-5. As a control, GST (Sigma-Aldrich, St. Louis, Mo., USA, catalogue #G-5663) was used at the same concentrations.

Example 29

Immunohistochemistry: Binding of tPA F-EGF to Human AD Brain

Paraffin brain sections of a human inflicted with AD was a kind gift of Prof. Slootweg (Dept. of Pathology, UMC Utrecht). Sections were deparaffinized in a series of xylene-ethanol. Endogenous peroxidases were blocked with methanol/1.5% $H_2O_2$ for 15 minutes. After rinsing in $H_2O$, sections were incubated with undiluted formic acid for ten minutes, followed by incubation in PBS for five minutes. Sections were blocked in 10% HPS in PBS for 15 minutes. Sections were exposed for two hours with 7 nM of tPA F-EGF-GST or GST in PBS/0.3% BSA. After three wash steps with PBS, sections were overlayed with 200 ng ml$^{-1}$ anti-GST antibody Z-5, for one hour. After washing, ready-to-use goat anti-rabbit Powervision (Immunologic, Duiven, The Netherlands, catalogue #DPVR-55AP) was applied and incubated for one hour. After washing, sections were stained for ten minutes with 3,3'-diamino benzidine (Sigma-Aldrich, St Louis, Mo., USA, catalogue #D-5905), followed by hematoxylin staining for ten seconds. After washing with $H_2O$, sections were incubated with Congo red according to the manufacturer's recommendations (Sigma Diagnostics, St Louis, Mo., USA). Sections were cleared in xylene and mounted with D.P.X. Mounting Medium (Nustain, Nottingham, U.K.). Analysis of sections was performed on a Leica DMIRBE fluorescence microscope (Rijswijk, The Netherlands). Fluorescence of Congo red was analyzed using an excitation wavelength of 596 nm and an emission wavelength of 620 nm.

Example 30

ELISA: Binding of tPA-F-GST and RPTPµ-GST to Human Ab (1-40) and Glycated Albumin Binding of tPA-F-GST and RPTPµ-GST to fibrous amyloids human Aβ (1-40) and albumin-g6p was assayed with an ELISA. In brief, human Aβ (1-40), albumin-g6p, or buffer only, were coated on a peptide I Immobilizer or a protein I Immobilizer, respectively. Wells were incubated with the purified GST-tagged constructs or control medium and binding was detected using primary anti-GST monoclonal antibody 2F3 and RAMPO. The wells were also incubated with 500 mM of tPA in the presence of 10 mM of εACA. Binding of tPA is independent of the lysyl binding site located at the kringle 2 domain. Binding of tPA was measured using primary antibody 374B and RAMPO. Experiments were performed in triplicate and blank readings of non-coated wells were substracted.

Example 31

Anti-AGE Antibodies

Antibodies against glucose-6-phosphate glycated bovine serum albumin were elicited in rabbits using standard immunization schemes. Anti-AGE1 was obtained after immunization with two-week glycated albumin-AGE (Prof. Dr. Ph.G. de Groot/Dr. I. Bobbink; unpublished data). The antibody was purified from serum using a Protein G column. Anti-AGE2 was developed by Davids Biotechnologie (Regensburg, Germany). After immunization with albumin-AGE:23, antibodies were affinity purified on human Aβ (1-40) conjugated to EMD Epoxy-activated beads (Merck, Darmstadt, Germany). Polyclonal mouse anti-AGE antibody was obtained after immunization with albumin-AGE:23 and human Aβ (1-40) in a molar ratio of 9:1. Polyclonal serum was obtained using standard immunization procedures, which were performed by the Academic Biomedical Cluster Hybridoma Facility (Utrecht University, The Netherlands). Subsequently, monoclonal antibodies were generated using standard procedures.

Example 32

ELISA: Binding of Antibodies Against Amyloid Peptides or Glycated Protein to Protein-AGE and Amyloid Fibers For ELISAs, amyloid compounds were immobilized on Exiqon peptide or protein Immobilizers (Vedbaek, Denmark), as described before. Anti-AGE antibodies and commercially available anti-Aβ (1-42) H-43 (Santa Cruz Biotechnology, Santa Cruz, Calif., USA) were diluted in PBS with 0.1% v/v Tween 20. Rabbit anti-human vitronectin K9234 was a kind gift of Dr. H. de Boer (UMC Utrecht) and was used as a negative control. For ELISAs with mouse polyclonal anti-albumin-AGE/Aβ, control serum with antibody elicited against an unrelated protein was used. Binding of mouse polyclonal anti-albumin-AGE/Aβ was performed using a dilution series of serum in PBS/0.1% Tween 20. For competitive binding assays with IAPP, anti-AGE1 was pre-incubated with varying IAPP concentrations. The IAPP fibers were spun down and the supernatant was applied in triplicate to wells of an ELISA plate coated with Aβ. Competitive binding assays with multiligand cross-β structure binding serine protease tPA were performed in a slightly different way. Coated Aβ and IAPP are overlayed with an anti-AGE1 or anti-Aβ (1-42) H-43 concentration related to the $k_D$, together with a concentration series of tPA. A $10^7$-$10^4$ times molar excess of lysine analogue εACA (10 mM) was present in the binding buffer in order to avoid binding of tPA to lysine residues of Aβ and IAPP, which would be independent of the presence of amyloid structures.

Example 33

Pull-Down Assay with Amyloid Peptides and Rabbit Anti-AGE1 Antibody

Anti-AGE1 was incubated with amyloid aggregates of Aβ (16-22), Aβ (1-40) and IAPP. After centrifugation, pellets were washed three times with PBS/0.1% Tween 20, dissolved in non-reducing sample buffer (1.5% (n/v) sodium dodecyl sulphate, 5% (v/v) glycerol, 0.01% (m/v) bromophenol blue, 30 mM Tris-HCl pH 6.8). Supernatant after pelleting of the amyloid fibers was diluted 1:1 with 2× sample buffer. Samples were applied to a polyacrylamide gel and after Western blotting, anti-AGE1 was detected with SWARPO.

Example 34

Immunohistochemical Analysis of the Binding of Anti-AGE2 to an Amyloid Plaque in a Section of a Human Brain Inflicted by AD Rabbit anti-AGE2, affinity purified on an Aβ column, was used for assaying binding properties towards amyloid plaques in brain sections of a human with AD. The procedure was performed essentially as described above. To avoid eventual binding of 11 μg ml$^{-1}$ anti-AGE2 to protein-AGE adducts or to human albumin in the brain section, 300 nM of g6p-glycated dipeptide Gly-Lys was added to the binding buffer, together with 0.3% m/v BSA. After the immunohistochemical stain, the section was stained with Congo red.

Example 35

Sandwich ELISA for Detection of Amyloid Albumin-AGE in Solution

For detection of amyloid cross-β structure in solutions, the sandwich ELISA approach was used. Actilyse tPA was immobilized at a concentration of 10 μg ml$^{-1}$ to wells of a 96-wells protein Immobilizer plate (Exiqon, Vedbaek, Denmark). Concentration series of albumin-AGE:23 and albumin-control:23 were added to the tPA-coated wells, as well as to non-coated control wells. Binding of amyloid structures was detected upon incubation with 1 μg ml$^{-1}$ anti-Aβ (1-42) H-43 (Santa Cruz Biotechnology, Santa Cruz, Calif., USA) and subsequently 0.3 μg ml$^{-1}$ SWARPO, followed by ortho-phenylene-diamine/$H_2O_2$/$H_2SO_4$ stain.

Example 36

Figure 2:
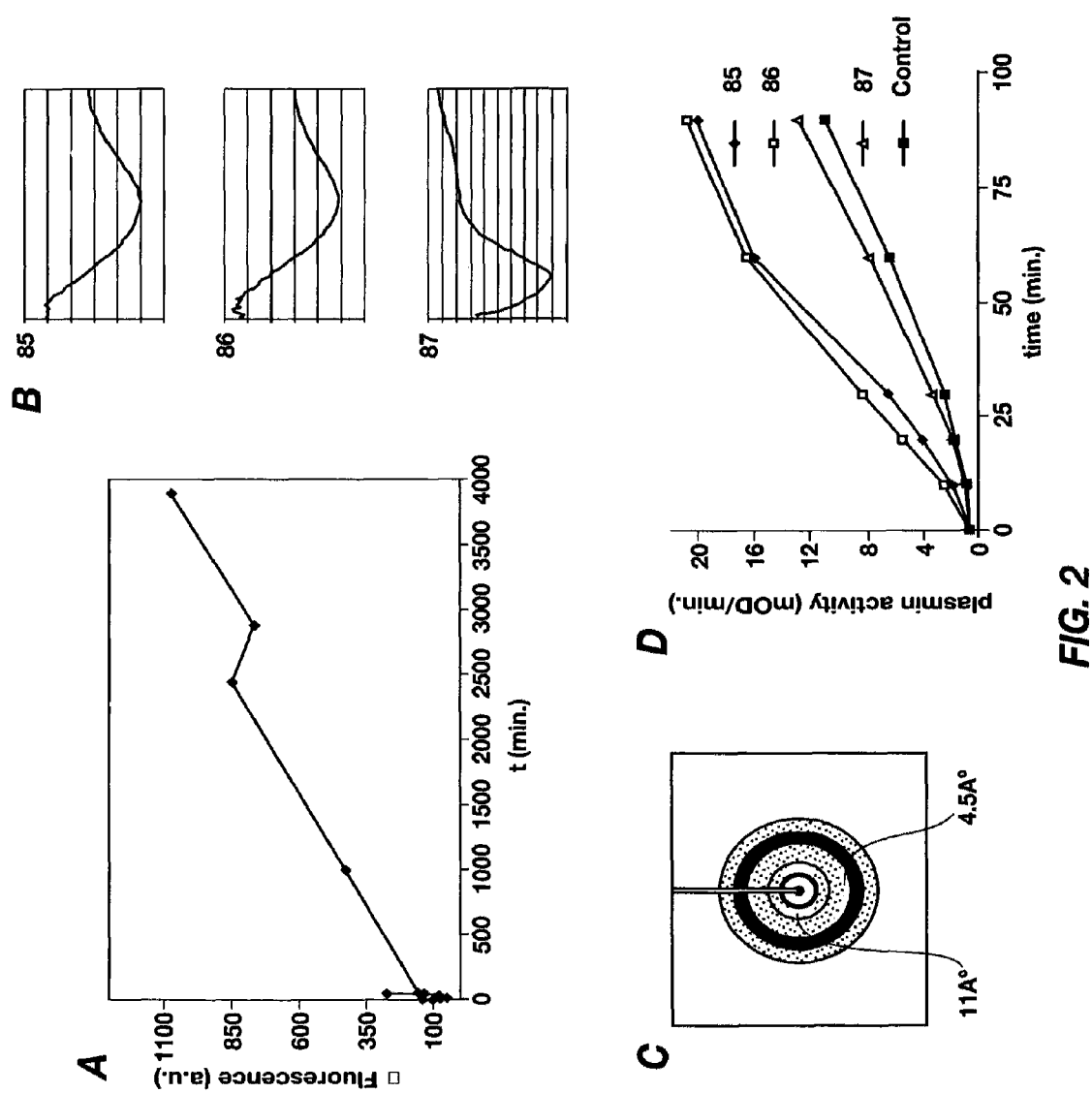

Cross-β Structure is Present in Fibrin and in Synthetic Peptides Derived from Fibrin It has been demonstrated herein that a fibrin clot stains with Congo red (not shown) and exhibits Thioflavin T fluorescence (FIG. 2, Panel A), indicative of the presence of amyloid structure in a fibrin clot. Using Congo red staining (not shown), circular dichroism measurements and X-ray diffraction analysis, it was shown that synthetic peptides derived from the sequence of fibrin adopt cross-β structure (FIG. 2, Panels B and C). These peptides were previously found to possess tPA-binding and tPA-activating properties.[18] The presence of cross-β structure in these peptides was found to correlate with the ability to stimulate tPA-mediated plasminogen activation (FIG. 2, Panel D).

These data provide evidence for physiological occurrence/relevance for formation of cross-β structure and the role of this structural element in binding of tPA to fibrin.

Example 37

Figure 3:
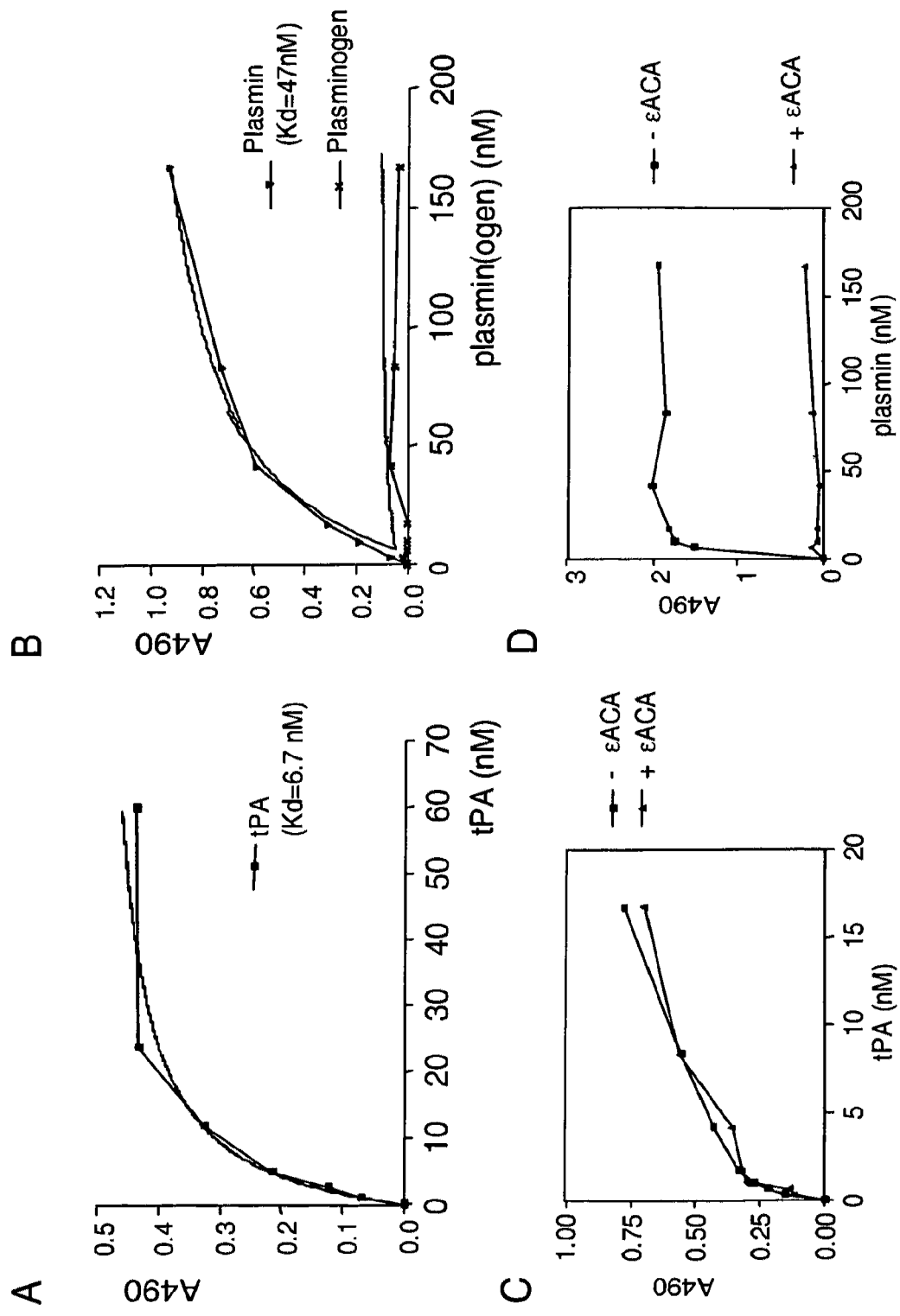

Aβ Contains Cross-β Structure, Binds Plasmin(Ogen) and tPA, Stimulates Plasminogen Activation, Induces Matrix Degradation and Induces Cell Detachment that is Aggravated by Plasminogen and Inhibited by CpB To test whether tPA, plasminogen and plasmin bind Aβ, solid-phase binding assays were performed. Aβ was coated onto plastic 96-well plates and binding of the peptide to either plasmin(ogen) or to tPA was assessed by overlaying the coated peptide with increasing concentrations of either tPA, plasminogen or plasmin. Binding was assessed using specific antibodies to either plasmin(ogen) or to tPA by performing ELISA. FIG. 3, Panel A, shows that tPA binds to Aβ with a $k_D$ of about 7 nM, similar to the $k_D$ of tPA binding to fibrin.[55] In contrast, No detectable binding of plasminogen to Aβ was found (FIG. 3, Panel B). However, activated plasminogen (plasmin) does bind to Aβ and does so with a $k_D$ of 47 nM. The fact that (active) plasmin, but not (inactive) plasminogen, binds to Aβ suggests that plasmin activity and, hence, the generation of free lysines, is important for binding of plasmin to Aβ. To test this, use was made of the lysine analogue ϵ-aminocaproic acid (ϵACA) and binding of plasmin and tPA to Aβ was tested in its presence. It is shown herein that the binding of plasmin to Aβ is completely abolished in the presence of ϵACA (FIG. 3, Panel D). In contrast, ϵACA has no effect on the tPA-Aβ interaction (FIG. 3, Panel C). Thus, it was concluded that plasmin binds to free lysines that were generated during the incubation period, presumably via its lysine-binding Kringle domain(s). In line with this, the $k_D$ of plasminogen Kringle domain binding to free lysines in fibrin is similar to the $k_D$ for plasmin binding to Aβ.

Figure 4:
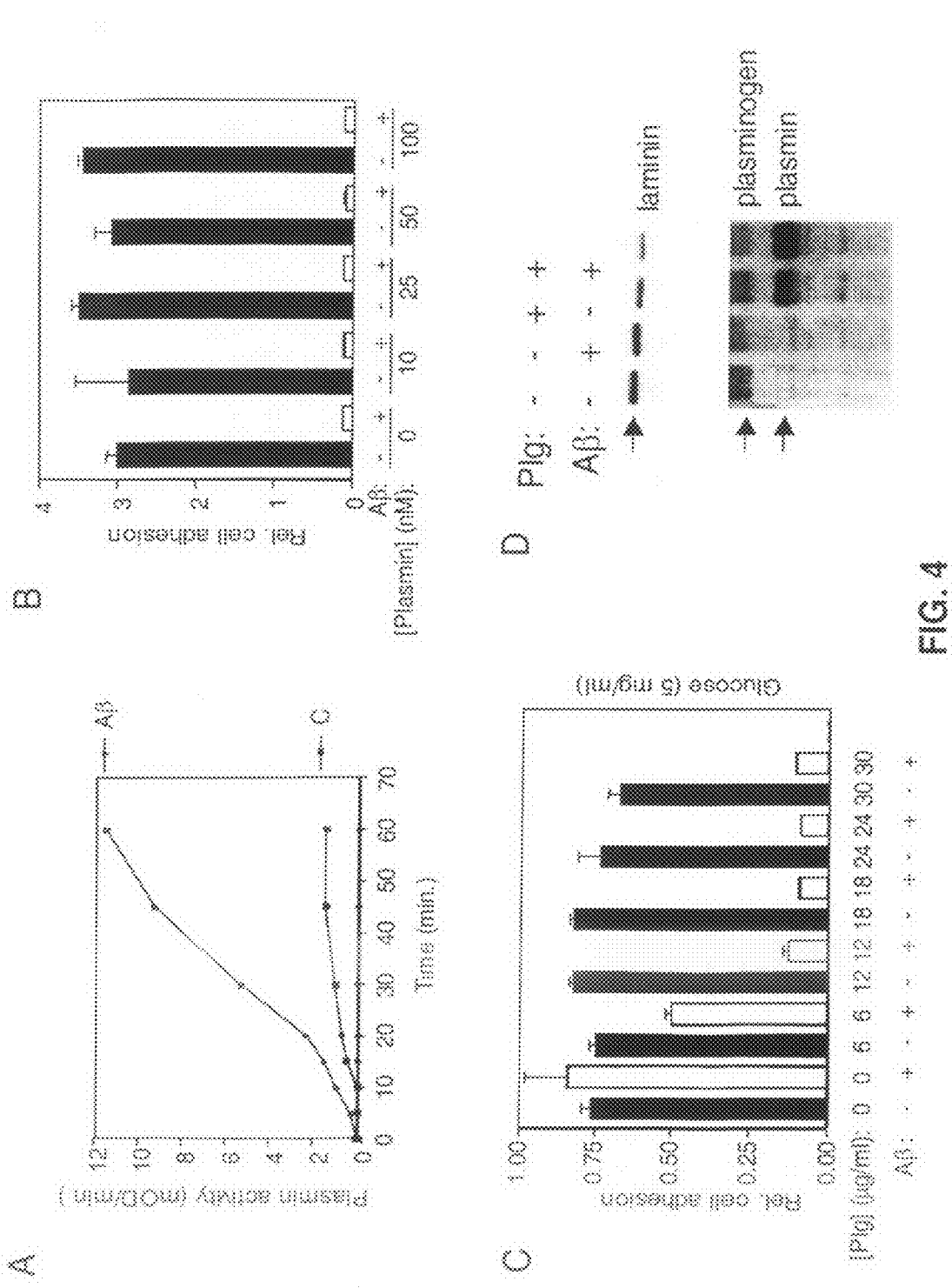

The kinetics of plasminogen activation in the absence and the presence of Aβ was investigated. As has been published before by Kingston et al.,[24] it was found that Aβ potently stimulates the activation of plasminogen by tPA (FIG. 4, Panel A). However, it was found that the reaction proceeds with second-order, rather than with first-order, kinetics. The possibility was considered that the generation of free lysines during the reaction was causing this phenomenon (see below). tPA-mediated plasmin generation has been implicated in neuronal cell death caused by ischemia or by excitotoxic amino acids. Recent data suggest that plasmin can degrade Aβ and thereby prevents Aβ toxicity.[56, 57] It was found that 48 hours following the addition of Aβ to a culture of differentiated N1E-115 cells, the majority of cells had died and detached from the matrix (not shown). When added together with Aβ, plasmin (up to 100 mM) was unable to ameliorate Aβ-induced cell detachment. Even prolonged pre-incubations of Aβ with 100 nM plasmin did not affect Aβ-induced cell detachment (FIG. 4, Panel B). Subsequently, the possibility was considered that plasmin generation may potentiate rather than inhibit Aβ-induced cell detachment and survival. To test this, N1E-115 cells were exposed to suboptimal concentrations of Aβ and low concentrations of plasminogen for 24 hours. In the absence of Aβ, plasminogen had no effect on cell adhesion (FIG. 4, Panel C). However, plasminogen had a dramatic potentiating effect on Aβ-induced cell detachment. The minimal levels of plasminogen that were required to potentiate Aβ-induced cell detachment (10-20 μg/ml) were well below those found in human plasma (250 pg/ml). Plasmin-mediated degradation of the extracellular matrix molecule laminin precedes neuronal detachment and cell death in ischemic brain. Whether Aβ-stimulated plasmin generation leads to laminin degradation was tested. Cell detachment was accompanied by degradation of the extracellular matrix protein laminin (FIG. 4, Panel D).

The possibility was considered that the generation of free lysines during Aβ-stimulated plasmin formation was responsible for the observed second-order kinetics. To test this, use was made of carboxypeptidase B (CpB), an enzyme that cleaves of C-terminal lysine and arginine residues, and the CpB-inhibitor CPI. FIG. 5, Panel A, shows that in the presence of CpB, the generation of plasmin was greatly diminished. Furthermore, this effect depends on CpB activity as it was abolished by co-incubation with CPI. FIG. 5, Panel A, also shows that CpB did not completely abolish Aβ-stimulated plasmin generation, but that the reaction proceeded with slow first-order kinetics. These data suggest that the (plasmin-mediated) generation of free lysines during the reaction is essential for efficient Aβ-stimulated plasmin generation, presumably by supporting plasminogen and tPA binding through interaction with their respective Kringle domains. A similar dependency on the generation of C-terminal lysines has been shown for efficient fibrin-mediated plasmin generation.[58] These results show that Aβ-stimulated plasmin formation is regulated by carboxypeptidase B in vitro. Thus, if cell detachment is the result of plasmin generation, CpB may affect Aβ-induced cell detachment and/or viability. It is shown herein that cell detachment induced by plasminogen and Aβ is completely prevented by co-incubation with CpB (FIG. 5, Panels B and C). This was accompanied by a complete inhibition of Aβ-stimulated plasmin formation, both in the medium and on the cells (FIG. 5, Panel D).

Example 38

Endostatin can Form Amyloid Fibers Comprising Cross-β Structure

Using Congo red staining (not shown), X-ray diffraction analysis and TEM, the presence of cross-β structure in aggregated endostatin from *Escherichia coli*, as well as from *Pichia pastoris*, and the ability of endostatin to form amyloid fibrils (FIG. 6, Panels A and B) has been demonstrated. It was found that bacterial endostatin produced reflection lines at 4.7 Å (hydrogen-bond distance), as well as at 10-11 Å (inter-sheet distance). The reflection lines showed maximal intensities at opposite diffraction angles. The fiber axis, with its 4.7 Å hydrogen bond repeat distance, was oriented along the vertical capillary axis. This implies that inter-sheet distance of 10-11 Å is perpendicular to these hydrogen bonds. This is consistent with the protein being a cross-β sheet conformation with a cross-β structure. Intramolecular sheets in a globular protein cannot cause a diffraction pattern that is ordered in this way. From the amount of background scattering, it follows that only part of the protein takes part in cross-β structure formation. It was found that the presence of cross-β structures in endostatin correlates with its ability to stimulate tPA-mediated plasminogen activation (FIG. 6, Panel C) and correlates with neuronal cell death (FIG. 6, Panel D).

Herein, it is demonstrated that endostatin is an example of a denatured protein that is able to stimulate the suggested cross-β pathway.

Example 39

IAPP Binds tPA and Stimulates tPA-Mediated Plasminogen Activation

Amyloid deposits of IAPP are formed in the pancreas of type II diabetic patients.[59] IAPP can cause cell death in vitro and is, therefore, thought to contribute to destruction of β-cells that is seen in vivo, which leads to insufficient insulin production. IAPP forms fibers comprising cross-β structure.[60]

Whether IAPP could stimulate tPA-mediated plasminogen activation was tested (FIG. 7). Indeed, similar to Aβ, IAPP enhanced the formation of plasmin by tPA.

Example 40

Glycated Albumin Binds Thioflavin T and tPA, and Aggregates as Amyloid Fibers Comprising Cross-β Structure It has been demonstrated that glycation of several proteins can induce or increase the ability of these proteins to bind tPA and stimulate tPA-mediated plasmin formation.[22, 61] It is shown herein that glycation of albumin with g6p not only confers high-affinity tPA binding to albumin (FIG. 8, Panel A), but also leads to its ability to bind Thioflavin T (FIG. 8, Panel C). Binding of tPA competed with Congo red (FIG. 8, Panel B). In addition, binding of Thioflavin T to glycated albumin competed with tPA (FIG. 8, Panels D and E). The fact that Congo red and/or Thioflavin T and tPA competed with each other illustrates that they have either the same or overlapping binding sites.

Analyses with TEM of the g6p-modified albumin preparations revealed that after a four-week incubation, amorphous albumin aggregates are formed (FIG. 8, Panel G), which exhibits a CD spectrum indicative for the presence of 7% of the albumin amino acid residues in β-sheet (Table I). Prolonged incubation up to 23 weeks resulted in a switch to highly ordered sheet-like fibrous structures, with a length of approximately 500 nm and a diameter ranging from about 50 to 100 nm (FIG. 8, Panel H). These fibers showed an increase to 19% β-sheet when analyzed with CD spectropolarimetry (Table I). Albumin from a different batch that was glycated in the same way already showed bundles of fibrous aggregates after a two-week period of incubation (FIG. 8, Panel I), whereas an increase in β-sheet content was not detected with CD spectropolarimetry (Table I). In each bundle, about ten separate linear 3-5-nm-wide fibers with a length of 200-300 nm can be were identified. On top of each bundle, regularly distributed spots are were seen with a diameter of approximately 5 nm. These spots may be accounted for by globular albumin molecules that are bound to the fibers or, alternatively, that are partly incorporated in the fibers. Aggregates were absent in control albumin (not shown) and no β-sheets were measured using CD spectropolarimetry (Table I). The fibrous structures obtained after two-week and 23-week periods of glycation enhance enhanced the fluorescence of Thioflavin T (ThT) in a similar way, whereas the amorphous precipitates obtained after four weeks hardly increased the fluorescent signal.

X-ray fiber diffraction analyses revealed that albumin-g6p (23 weeks) comprises a significant amount of crystalline fibers (FIG. 8, Panels J and L), whereas diffraction patterns of albumin-g6p (2 weeks) and albumin-g6p (4 weeks) showed features originating from amorphous precipitated globular protein very similar to the patterns obtained for albumin controls (FIG. 8, Panel K). For albumin-g6p (23 weeks), the 4.7 Å repeat corresponds to the characteristic hydrogen-bond distance between β-strands in β-sheets. The 2.3 and 3.3 Å repeats have a preferred orientation perpendicular to the 4.7 Å repeat (FIG. 8, Panel M). Combining the 2.3 and 3.3 Å repeats suggests that the fiber axis is oriented perpendicular to the direction of the hydrogen bonds, with a repeat of 6.8 Å. This dimension corresponds to the length of two peptide bonds and indicates that β-strands run parallel to the fiber axis. This implies that the albumin-g6p (23 weeks) structure is composed of cross-β structure consisting of packed β-sheets of hydrogen-bonded chains (FIG. 8, Panel N). A similar orientation is found in amyloid fibrils of the first predicted α-helical region of PrP$^c$.[62] When the a-axis is 9.4 Å, or alternatively 4.7 Å, and the c-axis is 6.8 Å, the 2.5 and 6.0 Å repeats can only be indexed as (h k l). This implies a highly ordered b-axis repeat corresponding to the inter β-sheet distance. With a-axis and c-axis of 4.7 or 9.4 Å and 6.8 Å, respectively, the strong 3.8 Å repeat should be indexed as (2 0 1) or (1 0 1). Considering all observations, it is clear that the albumin-g6p fibers (23 weeks) are built up by cross-β structures, a characteristic feature of amyloid fibrils.

These results show that due to incubation and/or modification with sugar moieties, cross-β structures in albumin are formed that are able to support tPA binding.

Example 41

Glycation of Hemoglobin Induces tPA Binding and Fiber Formation

Incubation of human hemoglobin with g6p resulted in high-affinity tPA binding (FIG. 9, Panel A). Amorphous aggregated Hb-g6p adducts including fibrils were observed with TEM (FIG. 9, Panel B), whereas control Hb did not aggregate (not shown). Human Hb of diabetes mellitus patients had the tendency to form fibrillar aggregates once more than 12.4% of the Hb is glycated (Table II).

Example 42

Amyloid Albumin is Formed Irrespective of the Original Carbohydrate (Derivative)

From the above-listed observations, it is clear that modification of —NH$_2$ groups of albumin with g6p induces formation of amyloid cross-β structure. The next question addressed was whether triggering of refolding of globular albumin into an amyloid fold was a restricted property of g6p, or whether amyloid formation occurs irrespective of the original carbohydrate or carbohydrate derivative used for AGE formation. Albumin solutions were incubated for 86 weeks at 37° C. with 1 M g6p, 250 mM DL-glyceraldehyde/100 mM NaCNBH$_3$, 1 M β-D-(-)-fructose, 1 M D(+)-glucose, 500 mM glyoxylic acid/100 mM NaCNBH$_3$, and corresponding PBS and PBS/NaCNBH$_3$ buffer controls. Glyceraldehyde and glyoxylic acid are carbohydrate derivatives that are precursors of AGE in Maillard reactions.[63, 64] After 86 weeks, albumin-glyceraldehyde and albumin-fructose were light-yellow/brown suspensions. Controls were colorless and clear solutions. Albumin-glucose and albumin-glyoxylic acid were clear light-yellow to light-brown solutions. Albumin-g6p:86 was a clear and dark brown solution. AGE formation was confirmed by autofluorescence measurements using AGE-specific excitation/emission wavelengths (not shown), binding of moab anti-AGE 4B5 (not shown) and binding of poab anti-AGE (not shown). As expected, albumin-glyoxylic acid did not show an autofluorescent signal due to the fact that (mainly) non-fluorescent carboxymethyl-lysine (CML) adducts are formed.[63]

The autofluorescence data and the binding of AGE-specific antibodies listed above show that various carbohydrates and carbohydrate derivatives led to similar AGE structures. Using g6p as the starting point for AGE formation, it is shown that albumin adopted amyloid properties similar to those observed in the well-studied fibrils of Aβ and IAPP. Therefore, the presence of amyloid structures in the albumin-AGE adducts obtained with alternative carbohydrates and derivatives was tested for. Fluorescence of albumin-AGE—ThT solutions (FIG. 10, Panel J) and of air-dried albumin-AGE preparations that were incubated with Congo red (FIG. 10, Panels A-I) was measured. Incubation of albumin with glyceraldehyde, glucose or fructose resulted in an increased fluorescent signal of ThT (FIG. 10, Panel J). After subtraction of background signals of ThT and buffer, no specific amyloid—ThT fluorescence was measured for albumin-glyoxylic acid and buffer controls. Albumin-g6p, albumin-glyceraldehyde and albumin-fructose gave a Congo red fluorescent signal similar to the signals of Aβ and IAPP (FIG. 10, Panels C-E, G and H). With albumin-glucose, a uniformly distributed pattern of fluorescent precipitates was observed (FIG. 10, Panel F). With albumin-glyoxylic acid and buffer controls, hardly any staining is observed (FIG. 10, Panels A, B and I). These ThT and Congo red fluorescence data show that, in addition to albumin-g6p, albumin-glyceraldehyde, albumin-glucose and albumin-fructose have amyloid-like properties. To further substantiate these findings, binding of amyloid-specific serine protease tPA in an ELISA was tested for. The enzyme bound specifically to albumin-g6p, albumin-glyceraldehyde, albumin-glucose and albumin-fructose (FIG. 10, Panels K and L) and to positive controls Aβ and IAPP, as was shown before.[49] No tPA binding was observed for albumin-glyoxylic acid and buffer controls.

From the ThT, Congo red and tPA data, it is clear that inducing amyloid properties in albumin is not an exclusive property of g6p. Apparently, a spectrum of carbohydrates and carbohydrate derivatives comprising g6p, glucose, fructose, glyceraldehyde, and likely more, has the capacity to trigger the switch from a globular native fold to the amyloid cross-β structure fold upon their covalent binding to albumin.

Example 43

Analysis of Congo Red Binding and tPA Binding to Aβ

It has been demonstrated that Aβ bound tPA and Congo red. It was shown that the binding of tPA to Aβ competed with Congo red (FIG. 11). These results support the findings herein that structures in Aβ, fibrin and glycated albumin are similar and are able to mediate the binding to tPA.

Example 44

Binding of Human FXII to Amyloid Peptides and Proteins that Contain the Cross-β Structure Fold The graphs in FIG. 12 show that FXII binds specifically to all amyloid compounds tested. $k_D$s for hAβ (1-40), FP13, albumin-AGE and Hb-AGE are approximately 2, 11, 8 and 0.5 nM, respectively. The data obtained with the competitive FXII—tPA ELISA show that tPA efficiently inhibits binding of FXII to amyloid (poly)peptides (FIG. 12). From these data, it is concluded that FXII and f.l. tPA compete for overlapping binding sites on hAβ (1-40). K2P-tPA did not inhibit FXII binding. Binding of FXII to albumin-AGE was also effectively abolished by tPA but not by K2P-tPA, similar to what was observed for hAβ (1-40). This indicates that FXII may bind in a similar manner to hAβ (1-40) and albumin-AGE. In addition, these data show that the first three domains of tPA (finger, EGF-like, kringle 1) seem to be involved in the inhibitory effect of f.l. tPA on interactions between FXII and amyloid hAβ (1-40) or albumin-AGE. Using a dot-blot assay, binding of FXII to spotted amyloid hΔIAPP and hAβ (1-40) was tested. No binding of FXII was observed for negative controls PBS and mΔIAPP (FIG. 12). However, FXII specifically bound to hAβ (1-40), in agreement with an earlier report,[65] as well as to hΔIAPP (FIG. 12). These data, together with the ELISA data shown in FIG. 12, Panels A-F, suggest that FXII can bind to polypeptides that do not share amino acid sequence homology, but which do share the cross-β structure fold. This is in accordance with the recent data on interactions between tPA and polypeptides that contain the amyloid-specific fold.

Example 45

Binding of tPA to the Cross-β Structure-Containing Molecules, Aβ and Glycated Albumin Requires the Presence of an N-Terminal Region in tPA, which Contains the Finger Domain Several domains in tPA have been shown to mediate binding to fibrin or fibrin fragments.[12, 53, 66, 67] However, it is unknown which domain of tPA is needed for binding to Aβ or other cross-β structure-containing molecules. It is shown that a mutated tPA, termed reteplase, which lacks the N-terminal finger, EGF and kringle 1 domain (K2-tPA), is unable to bind cross-βstructure-comprising molecules (FIG. 13, Panels A and B). These results suggest that the N-terminal region is required for binding of tPA to fibers comprising cross-β structure.

Example 46

Expression and Purification of tPA-F-GST and RPTP-GST

Purification of the GST-tagged constructs tPA-F-GST and RPTPµ-GST(control) from 293T medium using glutathione coupled to Sepharose 4B beads resulted in single bands of approximately 35 kDa and 150 kDa, respectively (not shown). Traces of BSA, originating from the FCS used in the medium, were also present.

Example 47

ELISA: Binding of tPA-F-GST and RPTP-GST to Human Aβ (1-40) and Glycated Albumin In the ELISA, control tPA bound to both human Aβ (1-40) and albumin-g6p in the presence of excess εACA (FIG. 13, Panel C). This shows that in the assay used, tPA is capable of binding to fibrous amyloids in a kringle 2-independent manner. The tPA-F domain bound to human Aβ (1-40) and to albumin-g6p, whereas no binding was observed with RPTPµ-GST. Therefore, binding observed with tPA-F-GST is specific and does not originate from the GST tag. This result points to the tPA finger domain as a specific domain designed by nature for binding to cross-β-structured amyloid fibers.

cDNA constructs in pcDNA3 of the F, F-EGF, EGF, F-EGF-K1 and K1 fragments of human tPA was prepared. Recombinant proteins with a C-terminal GST tag were expressed in BHK cells and secreted to the medium. Medium from BHK cells expressing the GST tag alone was used as a control. Conditioned medium was used for pull-down assays using Aβ and IAPP fibrils, followed by Western blot analyses. Efficient binding to Aβ was evident for all three tPA mutants that contain the finger domain, i.e., F-GST, F-EGF-GST and F-EGF-K1-GST (FIG. 13, Panel D). The K1-GST and EGF-GST constructs, as well as the GST tag alone, remain in the supernatant after Aβ incubation. A similar pattern was obtained after IAPP pull-downs (not shown).

Binding of purified tPA F-EGF-GST, recombinant f.l. Actilyse tPA and a GST control to immobilized amyloid fibrin fragment $\alpha_{148-160}$ FP13, amyloid IAPP and to non-amyloid mΔIAPP control was compared (FIG. 13, Panels E-G). Full-length tPA and tPA F-EGF-GST bind to all three amyloid peptides; for Aβ $k_D$s for tPA and F-EGF are 2 and 2 nM, respectively; for FP13, 5 and 2 nM; for IAPP, 2 and 13 nM. No binding to non-amyloid mΔIAPP was observed (FIG. 13, Panel E). GST did not bind to FP13 and IAPP, while some binding is detected to Aβ. This may reflect the small fraction of GST that bound to Aβ in the pull-down assay (FIG. 13, Panel D).

With immunohistochemical analysis, binding of the purified recombinant tPA F-EGF-GST construct to paraffin sections of human brain inflicted by AD was tested. Presence of amyloid depositions was confirmed by the Dept. of Pathology (UMC Utrecht) using standard techniques. In the experiments, these amyloid depositions were located using Congo red fluorescence (FIG. 13, Panels I, K and M). In FIG. 13, Panels H-K, it is clearly seen that areas that are positive for Congo red binding coincides with areas that are positive for tPA F-EGF-GST binding. Control stain with GST did not show specific binding of the tag alone (FIG. 13, Panels L and M).

At present, based on sequential and structural homology, next to tPA, three proteins are known that contain one or more finger domains, i.e., HGFa (one F domain), FXII (one F domain), Fn (one stretch of six F domains, two stretches of three F domains). From the above-listed results, it was concluded that the F domain of tPA (SEQ ID NO: 3) plays a crucial role in binding of tPA to amyloid peptides or polypeptides. It was hypothesized that the finger domain could be a general cross-β structure-binding module. Presently, four proteins, tPA, FXII, HGFa and fibronectin, are known that contain a finger motif. FIG. 14, Panel A, schematically depicts the localization of the finger module in the respective proteins. FIG. 14, Panel B, shows an alignment of the human amino acid sequences of the finger domains in these four proteins. (SEQ ID NOs: 3-17). FIG. 14, Panel C, shows a schematic representation of the three-dimensional structure of the finger domain of tPA (SEQ ID NO: 3), and of the fourth and fifth finger domain of fibronectin (SEQ ID NOs: 9 and 10). To test the hypothesis that finger domains in general bind amyloid, the F domains of HGFa (SEQ ID NO: 5) and FXII (SEQ ID NO: 4), as well as the fourth and fifth F domain of Fn (SEQ ID NOs: 9 and 10), which are known for their capacity to bind to fibrin,[68] were cloned. Using a pull-down assay, it was shown that Fn F4-GST and Fn F4-5-GST, as well as FXII F-GST and HGFa F-GST, specifically bind to Aβ (FIG. 13, Panels M and N) and IAPP (not shown). Fn F5-GST bound to Aβ to some extent, however, it was extracted less efficiently from the medium and seemed to be partly released during the washing procedure of the amyloid pellet (FIG. 13, Panel M). No construct was left in the medium after extraction of positive control tPA F-EGF-GST, whereas no negative control GST was detected in the pellet fraction (not shown). These data show that binding to amyloid peptides or polypeptides is not a unique capacity of the tPA F domain (SEQ ID NO: 3), yet a more general property of the F domains tested. Moreover, these data indicate that observed binding of FXII to amyloid (poly)peptides, as shown in FIG. 13, Panels A and H, and by Shibayama et al.,[65] is regulated via the F domain.

Example 48

Amyloid-Binding Domain of tPA

The finger domain of tPA has been shown to be of importance for high-affinity binding to fibrin.[12, 66] The present results using RETEPLASE® (K2-P tPA) and F-tPA, F-EGF-tPA and F-EGF-K1-tPA, indicate an important role for the N-terminal finger domain of tPA in binding to stimulatory factors other than fibrin. Thus far, all of these factors bind Congo red and contain cross-β structure. Furthermore, the binding site of fibronectin for fibrin has been mapped to the finger domain tandem F4-F5.[68] It has been demonstrated that plasminogen activation by full-length tPA, in the presence of fibrin fragment FCB2, can be inhibited by fibronectin.[69] Taken together, these observations suggest that tPA and fibronectin compete, via their finger domain, for the same or overlapping binding sites on fibrin. The data now shows that the F4-5 domains of Fn (SEQ ID NOs: 9 and 10) bind to amyloid Aβ.

Example 49

Binding of Anti-AGE Antibodies to Amyloid (Poly)Peptides and Binding of Anti-Aβ to Protein-AGE Adducts Recently, O'Nuallain and Wetzel[70] showed that antibodies elicited against a peptide with amyloid characteristics can bind to any other peptide with similar amyloid properties, irrespective of amino acid sequence. Based on these data and on the observations that tissue-type plasminogen activator and factor XII can bind to a family of sequence-unrelated polypeptides that share the amyloid-specific cross-β structure fold, a broader class of proteins can display affinity towards this structural unit, rather than towards a linear or conformational epitope, built up by specific amino acid residues. This prompted the question as to whether antibodies elicited against albumin-AGE, that contain the amyloid cross-β structure fold, also display the broad-range specificity towards any (poly)peptide which bears this cross-β structure fold.

In an ELISA set-up, α-AGE1, which was elicited against g6p-glycated albumin-AGE, bound to amyloid albumin-AGE:23 ($K_d$=66 nM) and Hb-AGE:32 ($K_d$=20 nM), as well as to Aβ (1-40) ($K_d$=481 nM) and IAPP ($K_d$=18 nM) (FIG. 15, Panels A-C). Negative controls were non-glycated albumin and Hb, non-amyloid peptide mouse ΔIAPP for IAPP and polyclonal anti-human vitronectin antibody α-hVn K9234 for Aβ. To test whether the same fraction of α-AGE1 binds to IAPP and Aβ, the antibody was pre-incubated with IAPP fibrils, followed by pelleting of the fibrils, together with the possible amyloid-binding fraction of α-AGE1. Binding of α-AGE1, left in the supernatant, to Aβ (1-40) was reduced (FIG. 15, Panel D). This indicates that the same fraction of a-AGE1 bound to IAPP and Aβ (1-40). With a pull-down assay, the binding of anti-AGE1 to amyloid peptides in an alternative way was assessed. After incubation of anti-AGE1 solutions with amyloid fibrils Aβ (16-22) (FIG. 15, Panel E, lanes 1-2), Aβ (1-40) (FIG. 15, Panel E, lanes 4-5), and IAPP (FIG. 15, Panel E; lanes 6-7), and subsequent pelleting of the amyloid fibrils, the supernatant was completely depleted from α-AGE1 by Aβ (16-22). With IAPP, approximately 50% of the antibody is found in the amyloid fraction, whereas less antibody is pelleted with Aβ (1-40). These data obtained in a complementary way, again show that anti-AGE1 can bind to amyloid peptides, which share no amino-acid sequence homology with albumin-AGE:23, though which share the cross-β structure fold. In addition, the observation that binding of tPA to amyloid peptides inhibited binding of anti-AGE1, also indicates that anti-AGE1, like tPA, binds bound to the cross-β structure fold (FIG. 15, Panels F and G). The observation that tPA reduces anti-AGE 1 binding to Aβ to a lesser extent than the reduction seen with IAPP, is putatively related to the higher number of anti-AGE1-binding sites on coated Aβ, when, compared with IAPP (see FIG. 15, Panels B and C), and to the higher affinity of tPA for IAPP ($k_D$=6 nM) than for Aβ ($k_D$=46 nM), when using Exiqon ELISA plates (not shown). The binding data together suggest that anti-AGE1 binds to this amyloid fold, irrespective of the (poly)peptide that bears the cross-β structure fold, which identifies anti-AGE1 as a member of the class of multiligand cross-β structure-binding proteins.

Based on the above-listed results obtained with anti-AGE1, testing was done as to whether commercially available rabbit anti-human Aβ (1-42) H-43 also displays broad-range specificity towards any (poly)peptide with unrelated amino acid sequence, although with amyloid characteristics. Indeed, with an ELISA, it was shown that H-43 not only binds to Aβ (1-40), but also to IAPP and albumin-AGE (FIG. 15, Panel H). In addition, binding of H-43 to immobilized IAPP was effectively diminished by tPA (FIG. 15, Panel I). These observations together show that anti-Aβ (1-42) H-43 can bind to other amyloid (poly)peptides in a way similar to multiligand cross-β structure-binding protein tPA.

ELISAs with polyclonal mouse anti-albumin-AGE/Aβ showed that the antibody not only binds to these antigens, but that it specifically binds to other amyloid peptides than those used for immunization (FIG. 15, Panels J-L). Similar to the rabbit anti-AGE1 antibody and anti-Aβ (1-42) H-43, anti-albumin-AGE/Aβ displayed affinity for the amyloid peptides tested, irrespective of amino acid sequence. This suggests that also mouse anti-albumin-AGE/Aβ is a multiligand amyloid-binding antibody.

Based on the amyloid-binding characteristics of anti-AGE1, anti-Aβ (1-42) H-43 and anti-albumin-AGE/Aβ, the amyloid-binding fraction of anti-AGE2, which is elicited against albumin-AGE:23, with Aβ fibrils irreversibly coupled to a column, was purified. This fraction was used for immunohistochemical analysis of a human brain section that is inflicted by Alzheimer's disease. In FIG. 15, Panel M, it is clearly seen that the antibody binds bound specifically to the spherical amyloid deposition, indicated by the Congo red fluorescence shown in FIG. 15, Panel N.

The finding that anti-amyloid and anti-AGE antibodies display affinity for a broad range of sequentially unrelated (poly)peptides as long as the cross-β structure fold is present, is in agreement with the recently published data by O'Nuallain and Wetzel[70] and Kayed et al.[71] From several older reports in literature, it can be distilled that anti-cross-β antibodies can be obtained. For example, cross-reactive antibodies against fibrin and Aβ and against Aβ and hemoglobin are described.[72, 73] It is indicated herein that fibrinogen and hemoglobin-AGE adopt the cross-β structure fold, which suggests that the cross-reactivity observed for anti-Aβ antibodies was, in fact, binding of anti-cross-β structure antibodies to similar structural epitopes on Aβ, fibrinogen and hemoglobin.

Based on the results with the poly-clonal anti-AGE and amyloid antibodies, it was hypothesized that anti-cross-β structure antibodies could be obtained. Therefore, the spleen of mice immunized with glycated BSA and Aβ was fused with myeloma cells. Subsequently, potential anti-cross-β structure antibodies were selected by examining binding of hybridoma-produced antibodies to glycated hemoglobin and IAPP. Using this procedure, a monoclonal antibody 3H7 was isolated that recognizes glycated hemoglobin, as well as several peptides that contain the cross-β structure (FIG. 16). No binding was observed to unglycated hemoglobin or a synthetic peptide that does not form amyloid fibers (mΔIAPP).

Example 50

Sandwich ELISA: Fishing Amyloid Structures from Solution

Using a sandwich ELISA approach with coated tPA that was overlayed with amyloid albumin-AGE:23 in solution, followed by detection with broad-range anti-Aβ (1-42) H-43 (FIG. 17), cross-β structure-containing proteins in solution were detected.

It is herein disclosed that the three-dimensional structures of the tPA finger domain[74, 75] and the fibronectin finger domains 4-5[75, 76] reveal striking structural homology with respect to local charge-density distribution. Both structures contain a similar solvent-exposed stretch of five amino acid residues with alternating charge; for tPA, Arg7, Glu9, Arg23, Glu32, Arg30; and for fibronectin, Arg83, Glu85, Lys87, Glu89, Arg90, located at the fifth finger domain, respectively. The charged-residue alignments are located at the same side of the finger module. These alignments may be essential for fibrin binding.

Based on the observations, results and the herein-disclosed similarities, it was shown that the same binding sites for tPA became present in all proteins that bound and activated tPA and that this binding site comprises a cross-β structure.

Taken together, the data shows that a cross-β structure is a physiological relevant quarternary structure element in which appearance is tightly regulated and in which occurrence induces a normal physiological response, i.e., the removal of unwanted biomolecules. To the knowledge of the inventors, the existence of a general system, which is termed "cross-β structure pathway," to remove unwanted biomolecules is herein disclosed for the first time. The results show that this mechanism is fundamental to nature and controls many physiological processes to protect organisms from induced damage or from accumulating useless or denatured biomolecules. If deregulated, by whatever means, this system may cause severe problems. On the other hand, if properly used, this system may be applicable for inducing cell death in specific target cells, like, for example, tumor cells.

Tables

TABLE I

Percentage β-sheet, as calculated front CD spectra

| Sample[‡] | Incubation time (weeks) | β-sheet (%)[†] |
|---|---|---|
| Aβ (16-22) | | 100 |
| Albumin-glyceraldehyde | 2 | 0 |
| Albumin control | 2 | 0 |
| Albumin-g6p | 2 | 0 |
| Albumin-g6p | 4 | 7 |
| Albumin control | 23 | 0 |
| Albumin-g6p | 23 | 19 |

[‡]Two-weeks incubated albumin was from a different batch than four- and 23-weeks incubated albumin.
[†]Percentage of amino acid residues in β-sheets are given.

TABLE II

Correlation between $Hb_{A1c}$ concentrations and Hb fiber formation in vitro

| Healthy controls | | | Diabetes mellitus patients | | |
|---|---|---|---|---|---|
| sample | [$Hb_{A1c}$] (%)[‡] | Fibers[†] | sample | [$Hb_{A1c}$] (%)[‡] | Fibers[†] |
| 1 | 5.6 | – | 1 | 5.5 | – |
| 2 | 5.9 | – | 2 | 5.8 | – |

TABLE II-continued

Correlation between $Hb_{A1c}$ concentrations and Hb fiber formation in vitro

| Healthy controls | | | Diabetes mellitus patients | | |
|---|---|---|---|---|---|
| sample | [$Hb_{A1c}$] (%)‡ | Fibers† | sample | [$Hb_{A1c}$] (%)‡ | Fibers† |
| 3 | 6.2 | − | 3 | 5.8 | − |
|  |  |  | 4 | 10.7 | − |
|  |  |  | 5 | 11.3 | − |
|  |  |  | 6 | 11.6 | − |
|  |  |  | 7 | 12.4 | + |
|  |  |  | 8 | 12.5 | − |
|  |  |  | 9 | 12.5 | − |
|  |  |  | 10 | 12.6 | + |
|  |  |  | 11 | 12.7 | − |
|  |  |  | 12 | 12.8 | − |
|  |  |  | 13 | 13.3 | + |
|  |  |  | 14 | 13.7 | + |
|  |  |  | 15 | 14.8 | + |
|  |  |  | 16 | 15.3 | + |

‡The $Hb_{A1c}$ concentration is given as a percentage of the total amount of Hb present in erythrocytes of diabetes mellitus patients and of healthy controls. The s.d. is 2.3% of the values given.
†Presence of fibers as determined with TEM.

REFERENCES

1. Bucciantini M., Giannoni E., Chiti F., et al. Inherent toxicity of aggregates implies a common mechanism for protein misfolding diseases. *Nature* 2002; 416:507-511.
2. Rochet J. C., Lansbury P. T., Jr. Amyloid fibrillogenesis: themes and variations. *Curr. Opin. Struct. Biol.* 2000; 10:60-68.
3. Carmeliet P., Bouche A., De Clercq C., et al. Biological effects of disruption of the tissue-type plasminogen activator, urokinase-type plasminogen activator, and plasminogen activator inhibitor-1 genes in mice. *Ann. N.Y. Acad. Sci.* 1995; 748:367-381.
4. Carmeliet P., Collen D. Genetic analysis of the plasminogen and coagulation system in mice. *Haemostasis* 1996; 26 Suppl. 4:132-153.
5. Collen D., Lijnen H. R. Molecular basis of fibrinolysis, as relevant for thrombolytic therapy. *Thromb. Haemost.* 1995; 74:167-171.
6. Lijnen H. R., Collen D. Mechanisms of physiological fibrinolysis. *Baillieres Clin. Haematol.* 1995; 8:277-290.
7. Bosma P. J., Rijken D. C., Nieuwenhuizen W. Binding of tissue-type plasminogen activator to fibrinogen fragments. *Eur. J. Biochem.* 1988; 172:399-404.
8. Grailhe P., Nieuwenhuizen W., Angles-Cano B. Study of tissue-type plasminogen activator binding sites on fibrin using distinct fragments of fibrinogen. *Eur. J. Biochem.* 1994; 219:961-967.
9. Nieuwenhuizen W. Fibrin-mediated plasminogen activation. *Ann. N.Y. Acad. Sci.* 2001; 936:237-246.
10. Yakovlev S., Makogonenko E., Kurochkina N., Nieuwenhuizen W., Ingham K., Medved L. Conversion of fibrinogen to fibrin: mechanism of exposure of tPA- and plasminogen-binding sites. *Biochemistry* 2000; 39:15730-15741.
11. Bakker A. H., Weening-Verhoeff E. J., Verheijen J. H. The role of the lysyl binding site of tissue-type plasminogen activator in the interaction with a forming fibrin clot. *J. Biol. Chem.* 1995; 270:12355-12360.
12. de Munk G. A., Caspers M. P., Chang G. T., Pouwels P. H., Enger-Valk B. E., Verheijen J. H. Binding of tissue-type plasminogen activator to lysine, lysine analogues, and fibrin fragments. *Biochemistry* 1989; 28:7318-7325.
13. Fleury V., Loyau S., Lijnen H. R., Nieuwenhuizen W., Angles-Cano B. Molecular assembly of plasminogen and tissue-type plasminogen activator on an evolving fibrin surface. *Eur. J. Biochem.* 1993; 216:549-556.
14. Haddeland U., Sletten K., Bennick A., Nieuwenhuizen W., Brosstad F. Aggregated, conformationally changed fibrinogen exposes the stimulating sites for t-PA-catalysed plasminogen activation. *Thromb. Haemost.* 1996; 75:326-331.
15. Hasan A. A., Chang W. S., Budzynski A. Z. Binding of fibrin fragments to one-chain and two-chain tissue-type plasminogen activator. *Blood* 1992; 79:2313-2321.
16. Nieuwenhuizen W., Vermond A., Voskuilen M., Traas D. W., Verheijen J. H. Identification of a site in fibrin(ogen) which is involved in the acceleration of plasminogen activation by tissue-type plasminogen activator. *Biochim. Biophys. Acta.* 1983; 748:86-92.
17. Nieuwenhuizen W., Schielen W. J., Yonekawa O., Tesser G. I., Voskuilen M. Studies on the localization and accessibility of sites in fibrin which are involved in the acceleration of the activation of plasminogen by tissue-type plasminogen activator. *Adv. Exp. Med. Biol.* 1990; 281:83-91.
18. Nieuwenhuizen W. Sites in fibrin involved in the acceleration of plasminogen activation by t-PA. Possible role of fibrin polymerisation. *Thromb. Res.* 1994; 75:343-347.
19. Schielen W. J., Adams H. P., Voskuilen M., Tosser G. I., Nieuwenhuizen W. The sequence A alpha-(154-159) of fibrinogen is capable of accelerating the t-PA catalysed activation of plasminogen. *Blood Coagul. Fibrinolysis* 1991; 2:465-470.
20. Tsurupa G., Medved L. Identification and characterization of novel tPA- and plasminogen-binding sites within fibrin(ogen) alpha C-domains. *Biochemistry* 2001; 40:801-808.
21. Yonekawa O., Voskuilen M., Nieuwenhuizen W. Localization in the fibrinogen gamma-chain of a new site that is involved in the acceleration of the tissue-type plasminogen activator-catalysed activation of plasminogen. *Biochem J.* 1992; 283 (Pt 1):187-191.
22. Bobbink I. W., Tekelenburg W. L., Sixma J. J., de Boer H. C., Banga J. D., de Groot P. G. Glycated proteins modulate tissue-plasminogen activator-catalyzed plasminogen activation. *Biochem. Biophys. Res. Commun.* 1997; 240:595-601.
23. Hu G. F., Riordan J. F. Angiogenin enhances actin acceleration of plasminogen activation. *Biochem. Biophys. Res. Commun.* 1993; 197:682-687.
24. Kingston I. B., Castro M. J., Anderson S. In vitro stimulation of tissue-type plasminogen activator by Alzheimer amyloid beta-peptide analogues. *Nat. Med.* 1995; 1:138-142.
25. Lind S. E., Smith C. J. Actin accelerates plasmin generation by tissue plasminogen activator. *J. Biol. Chem.* 1991; 266:17673-17678.
26. Machovich R., Owen W. G. Denatured proteins as cofactors for plasminogen activation. *Arch. Biochem. Biophys.* 1997; 344:343-349.
27. Machovich R., Ajtai K., Kolev K., Owen W. G. Myosin as cofactor and substrate in fibrinolysis. *FEBS Lett.* 1997; 407:93-96.
28. Machovich R., Komorowicz E., Kolev K., Owen W. G. Facilitation of plasminogen activation by denatured prothrombin. *Thromb. Res.* 1999; 94:389-394.
29. Parkkinen J., Hacker J., Korhonen T. K. Enhancement of tissue plasminogen activator-catalyzed plasminogen activation by *Escherichia coli* S. fimbriae associated with neonatal septicaemia and meningitis. *Thromb. Haemost.* 1991; 65:483-486.
30. Parkkinen J., Rauvala H. Interactions of plasminogen and tissue plasminogen activator (t-PA) with amphoterin. Enhancement of t-PA-catalyzed plasminogen activation by amphoterin. *J. Biol. Chem.* 1991; 266:16730-16735.
31. Pryzdial E. L., Bajzar L., Nesheim M. E. Prothrombinase components can accelerate tissue plasminogen activator-catalyzed plasminogen activation. *J. Biol. Chem.* 1995; 270:17871-17877.
32. Radcliffe R., Heinze T. Stimulation of tissue plasminogen activator by denatured proteins and fibrin clots: a possible additional role for plasminogen activator? *Arch. Biochem. Biophys.* 1981; 211:750-761.
33. Sheng S., Truong B., Fredrickson D., Wu R., Pardee A. B., Sager R. Tissue-type plasminogen activator is a target of the tumor suppressor gene maspin. *Proc. Natl. Acad. Sci. U.S. A.* 1998; 95:499-504.
34. Silverstein R. L., Leung L. L., Harpel P. C., Nachman R. L. Complex formation of platelet thrombospondin with plasminogen. Modulation of activation by tissue activator. *J. Clin. Invest.* 1984; 74:1625-1633.
35. Stack S., Gonzalez-Gronow M., Pizzo S. V. Regulation of plasminogen activation by components of the extracellular matrix. *Biochemistry* 1990; 29:4966-4970.
36. Wada H., Kumeda Y., Ogasawara Z., et al. Stimulation of tissue type plasminogen activator by leukaemic cell homogenates. *Blood Coagul. Fibrinolysis* 1993; 4:591-597.
37. Carrell R. W., Gooptu B. Conformational changes and disease—serpins, prions and Alzheimer's. *Curr. Opin. Struct. Biol.* 1998; 8:799-809.
38. Krieger M., Stern D. M. Series introduction: multiligand receptors and human disease. *J. Clin. Invest.* 2001; 108: 645-647.
39. Schmidt A. M., Yan S. D., Wautier J. L., Stern D. Activation of receptor for advanced glycation end products: a mechanism for chronic vascular dysfunction in diabetic vasculopathy and atherosclerosis. *Circ. Res.* 1999; 84:489-497.
40. Schmidt A. M., Yan S. D., Yan S. F., Stern D. M. The biology of the receptor for advanced glycation end products and its ligands. *Biochim. Biophys. Acta.* 2000; 1498:99.111.
41. Schmidt A. M., Hofmann M., Taguchi A., Yan S. D., Stern D. M. RAGE: a multiligand receptor contributing to the cellular response in diabetic vasculopathy and inflammation. *Semin. Thromb. Hemost.* 2000; 26:485-493.
42. Schmidt A. M., Yan S. D., Yan S. F., Stern D. M. The multiligand receptor RAGE as a progression factor amplifying immune and inflammatory responses. *J. Clin. Invest.* 2001; 108:949-955.
43. Weldon D. T., Maggio J. E., Mantyh P. W. New insights into the neuropathology and cell biology of Alzheimer's disease. *Geriatrics* 1997; 52 Suppl. 2:S13-S16.
44. Yan S. D., Roher A., Chaney M., Zlokovic B., Schmidt A. M., Stern D. Cellular cofactors potentiating induction of stress and cytotoxicity by amyloid beta-peptide. *Biochim. Biophys. Acta.* 2000; 1502:145-157.
45. Balbach J. J., Ishii Y., Antzutkin O. N., et al. Amyloid fibril formation by A beta 16-22, a seven-residue fragment of the Alzheimer's beta-amyloid peptide, and structural characterization by solid state NMR. *Biochemistry* 2000; 39:13748-13759.
46. Bobbink I. W., de Boer H. C., Tekelenburg W. L., Banga J. D., de Groot P. G. Effect of extracellular matrix glycation on endothelial cell adhesion and spreading: involvement of vitronectin. *Diabetes* 1997; 46:87-93.
47. Boehm T., Folkman J., Browder T., O'Reilly M. S. Antiangiogenic therapy of experimental cancer does not induce acquired drug resistance. *Nature* 1997; 390:404-407.
48. Andrade M. A., Chacon P., Merelo J. J., Moran F. Evaluation of secondary structure of proteins from UV circular dichroism spectra using an unsupervised learning neural network. *Protein Eng.* 1993; 6:383-390.
49. Kranenburg O., Bouma B., Kroon-Batenburg L. M., et al. Tissue-type plasminogen activator is a multiligand cross-beta structure receptor. *Curr. Biol.* 2002; 12:1833-1839.
50. van Zonneveld A. J., Veerman H., Pannekoek H. On the interaction of the finger and the kringle-2 domain of tissue-type plasminogen activator with fibrin. Inhibition of kringle-2 binding to fibrin by epsilon-amino caproic acid. *J. Biol. Chem.* 1986; 261:14214-14218.
51. LeVine H., III. Quantification of beta-sheet amyloid fibril structures with thioflavin T. *Methods Enzymol.* 1999; 309: 274-284.
52. Kranenburg O., Scharnhorst V., Van der Eb A. J., Zantema A. Inhibition of cyclin-dependent kinase activity triggers neuronal differentiation of mouse neuroblastoma cells. *J. Cell. Biol.* 1995; 131:227-234.
53. Johannessen M., Diness V., Pingel K., et al. Fibrin affinity and clearance of t-PA deletion and substitution analogues. *Thromb. Haemost.* 1990; 63:54-59.
54. Gebbink M. F., Zondag G. C., Koningstein G. M., Feiken E., Wubbolts R. W., Moolenaar W. H. Cell surface expression of receptor protein tyrosine phosphatase RPTP mu is regulated by cell-cell contact. *J. Cell. Biol.* 1995; 131:251-260.
55. Stewart R. J., Fredenburgh J. C., Weitz J. I. Characterization of the interactions of plasminogen and tissue and vampire bat plasminogen activators with fibrinogen, fibrin, and the complex of D-dimer non-covalently linked to fragment E. *J. Biol. Chem.* 1998; 273:18292-18299.
56. Tucker H. M., Kihiko M., Caldwell J. N., et al. The plasmin system is induced by and degrades amyloid-beta aggregates. *J. Neurosci.* 2000; 20:3937-3946.
57. Tucker H. M., Kihiko-Ehmann M., Wright S., Rydel R. E., Estus S. Tissue plasminogen activator requires plasminogen to modulate amyloid-beta neurotoxicity and deposition. *J. Neurochem.* 2000; 75:2172-2177.
58. Redlitz A., Tan A. K., Eaton D. L., Plow E. F. Plasma carboxypeptidases as regulators of the plasminogen system. *J. Clin. Invest.* 1995; 96:2534-2538.
59. Hayden M. R., Tyagi S. C. "A" is for amylin and amyloid in type 2 diabetes mellitus. *J.O.P.* 2001; 2:124-139.
60. Moriarty D. F., Raleigh D. P. Effects of sequential proline substitutions on amyloid formation by human amylin 20-29. *Biochemistry* 1999; 38:1811-1818.
61. Saishoji T., Higashi T., Ikeda K., et al. Advanced glycation end products stimulate plasminogen activator activity via GM-CSF in RAW 264.7 cells. *Biochem. Biophys. Res. Commun.* 1995; 217:278-285.
62. Nguyen J. T., Inouye H., Baldwin M. A., et al. X-ray diffraction of scrapie prion rods and PrP peptides. *J. Mol. Biol.* 1995; 252:412-422.
63. Motomiya Y., Oyama N., Iwamoto H., Uchimura T., Maruyama I. N epsilon-(carboxymethyl)lysine in blood from maintenance hemodialysis patients may contribute to dialysis-related amyloidosis. *Kidney Int.* 1998; 54:1357-1366.
64. Sady C., Jiang C. L., Chellan P., et al. Maillard reactions by alpha-oxoaldehydes: detection of glyoxal-modified proteins. *Biochim. Biophys. Acta.* 2000; 1481:255-264.

65. Shibayama Y., Joseph K., Nakazawa Y., Ghebreihiwet B., Peerschke E. I., Kaplan A. P. Zinc-dependent activation of the plasma kinin-forming cascade by aggregated beta amyloid protein. *Clin. Immunol.* 1999; 90:89-99.
66. Bennett W. F., Paoni N. F., Keyt B. A., et al. High resolution analysis of functional determinants on human tissue-type plasminogen activator. *J. Biol. Chem.* 1991; 266: 5191-5201.
67. Horrevoets A. J., Smilde A., de Vries C., Pannekoek H. The specific roles of finger and kringle 2 domains of tissue-type plasminogen activator during in vitro fibrinolysis. *J. Biol. Chem.* 1994; 269:12639-12644.
68. Matsuka Y. V., Medved L. V., Brew S. A., Ingham K. C. The NH2-terminal fibrin-binding site of fibronectin is formed by interacting fourth and fifth finger domains. Studies with recombinant finger fragments expressed in *Escherichia coli. J. Biol. Chem.* 1994; 269:9539-9546.
69. Beckmann R., Geiger M., de Vries C., Pannekoek H., Binder B. R. Fibronectin decreases the stimulatory effect of fibrin and fibrinogen fragment FCB-2 on plasmin formation by tissue plasminogen activator. *J. Biol. Chem.* 1991; 266:2227-2232.
70. O'Nuallain B., Wetzel R. Conformational Abs recognizing a generic amyloid fibril epitope. *Proc. Natl. Acad. Sci. U.S.A.* 2002; 99:1485-1490.
71. Kayed R., Head E., Thompson J. L., et al. Common structure of soluble amyloid oligomers implies common mechanism of pathogenesis. *Science* 2003; 300:486-489.
72. Cutler P., Brown F., Camilleri P., et al. The recognition of haemoglobin by antibodies raised for the immunoassay of beta-amyloid. *FEBS Lett.* 1997; 412:341-345.
73. Stern R. A., Trojanowski J. Q., Lee V. M. Antibodies to the beta-amyloid peptide cross-react with conformational epitopes in human fibrinogen subunits from peripheral blood. *FEBS Lett.* 1990; 264:43-47.
74. Downing A. K., Driscoll P. C., Harvey T. S., et al. Solution structure of the fibrin binding finger domain of tissue-type plasminogen activator determined by 1H nuclear magnetic resonance. *J. Mol. Biol.* 1992; 225:821-833.
75. Smith B. O., Downing A. K., Driscoll P. C., Dudgeon T. J., Campbell I. D. The solution structure and backbone dynamics of the fibronectin type I and epidermal growth factor-like pair of modules of tissue-type plasminogen activator. *Structure* 1995; 3:823-833.
76. Williams M. J., Phan I., Harvey T. S., Rostagno A., Gold L. I., Campbell I. D. Solution structure of a pair of fibronectin type 1 modules with fibrin binding activity. *J. Mol. Biol.* 1994; 235:1302-1311.

What is claimed is:

1. A method for diminishing plaques comprising cross-β structures involved in a disease in a subject, the method comprising administering, to a subject in need thereof, a compound able to directly bind to a cross-β structure in a protein in the subject, for the purpose of allowing the subject to remove the cross-β structure, so as to diminish plaques in the subject, wherein said compound is a peptide consisting of a finger domain.

* * * * *

UNITED STATES PATENT AND TRADEMARK OFFICE
CERTIFICATE OF CORRECTION

PATENT NO. : 8,158,585 B2
APPLICATION NO. : 11/982161
DATED : April 17, 2012
INVENTOR(S) : Barend Bouma et al.

It is certified that error appears in the above-identified patent and that said Letters Patent is hereby corrected as shown below:

On the title page:
In ITEM (75) Inventors:  change "Martin" to --Martijn--
change "Gebbink, Eemnes" to --Gebbink, Bunnik--
change "Kroon-Batenburg, Bunnik" to
--Kroon-Batenburg, Eemnes--

On the title page:
In ITEM (56) References Cited
    FOREIGN PATENT DOCUMENTS
    Page 2, 1$^{st}$ column, 15$^{th}$ entry
        (line 76)  delete "MO  01/12598  A2  2/2001"
    OTHER PUBLICATIONS
    Page 3, 2$^{nd}$ column, 1$^{st}$ line of the
        5$^{th}$ entry (line 15)  change "Stmcture" to --Structure--
    Page 3, 2$^{nd}$ column, 1$^{st}$ line of the
        12$^{th}$ entry (line 33)  change "et al., Biol" to --et al., J. Biol--
    Page 3, 2$^{nd}$ column, 1$^{st}$ line of the
        14$^{th}$ entry (line 40)  change "(CDI4)" to --(CD14)--
    Page 3, 2$^{nd}$ column, 1$^{st}$ line of the
        20$^{th}$ entry (line 53)  change "intennediate" to --intermediate--
    Page 4, 2$^{nd}$ column, 2$^{nd}$ line of the
        12$^{th}$ entry (line 37)  change "7645-771S," to --764S-771S,--
    Page 5, 1$^{st}$ column, 2$^{nd}$ line of the
        17$^{th}$ entry (line 53)  change "SEL1L" to --SELIL--

In the drawings:
    In FIG. 2, Panel A  change "□" to --Δ--
    In FIG. 2, Panel C  change two instances of "A°" to --Å--
    In FIG. 8 (page 2), Panel J  change five instances of "A°" to --Å--

Signed and Sealed this
Twenty-first Day of May, 2013

Teresa Stanek Rea
*Acting Director of the United States Patent and Trademark Office*

Replace FIG. 2, Panel A with the following amended figure:
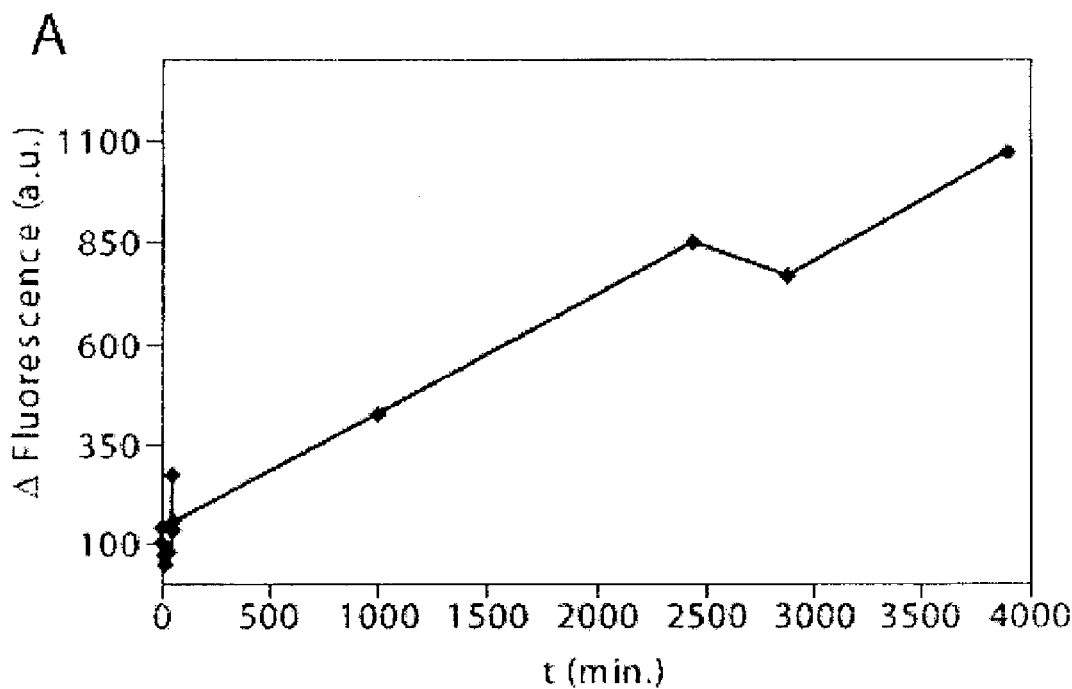
Replace FIG. 2, Panel C with the following amended figure:
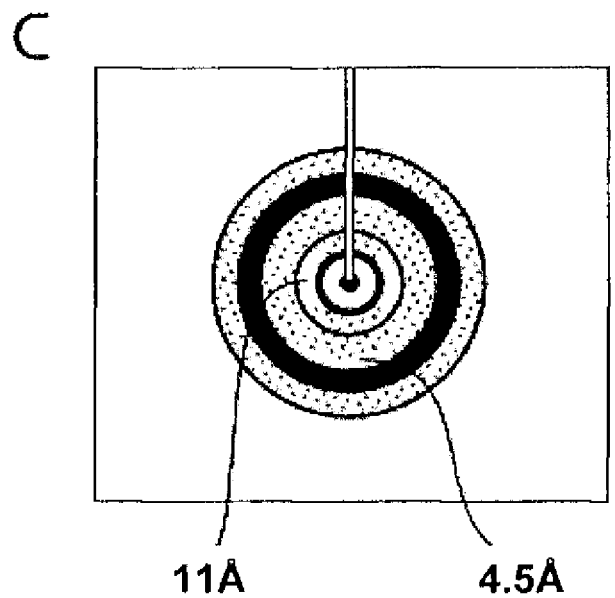

CERTIFICATE OF CORRECTION (continued)
U.S. Pat. No. 8,158,585 B2

Replace FIG. 8 (page 2), Panel J with the following amended figure:

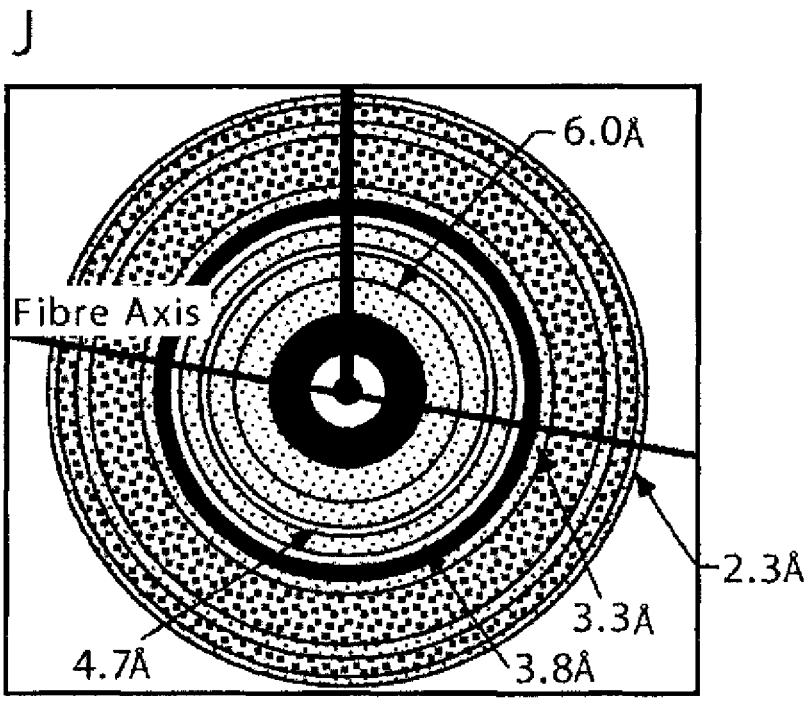

In the specification:

| | | |
|---|---|---|
| COLUMN 42, | LINE 63, | change "binds bound" to --bound-- |
| COLUMN 43, | LINE 39, | change "binds bound" to --bound-- |

UNITED STATES PATENT AND TRADEMARK OFFICE
CERTIFICATE OF CORRECTION

PATENT NO. : 8,158,585 B2  
APPLICATION NO. : 11/982161  
DATED : April 17, 2012  
INVENTOR(S) : Barend Bouma et al.

Page 1 of 3

It is certified that error appears in the above-identified patent and that said Letters Patent is hereby corrected as shown below:

On the title page:
ITEM (75) Inventors should read

--Barend Bouma, Houten (NL); Martijn F. B. G. Gebbink, Eemnes (NL); Onno W. Kranenburg, Amsterdam (NL); Louise M. J. Kroon-Batenburg, Bunnik (NL)--

On the title page:
In ITEM (56) References Cited
    FOREIGN PATENT DOCUMENTS
    Page 2, 1$^{st}$ column, 15$^{th}$ entry
        (line 76)    delete "MO  01/12598  A2  2/2001"
    OTHER PUBLICATIONS
    Page 3, 2$^{nd}$ column, 1$^{st}$ line of the
        5$^{th}$ entry (line 15)    change "Stmcture" to --Structure--
    Page 3, 2$^{nd}$ column, 1$^{st}$ line of the
        12$^{th}$ entry (line 33)    change "et al., Biol" to --et al., J. Biol--
    Page 3, 2$^{nd}$ column, 1$^{st}$ line of the
        14$^{th}$ entry (line 40)    change "(CDI4)" to --(CD14)--
    Page 3, 2$^{nd}$ column, 1$^{st}$ line of the
        20$^{th}$ entry (line 53)    change "intennediate" to --intermediate--
    Page 4, 2$^{nd}$ column, 2$^{nd}$ line of the
        12$^{th}$ entry (line 37)    change "7645-771S," to --764S-771S,--
    Page 5, 1$^{st}$ column, 2$^{nd}$ line of the
        17$^{th}$ entry (line 53)    change "SEL1L" to --SELIL--

This certificate supersedes the Certificate of Correction issued May 21, 2013.

Signed and Sealed this
Eighth Day of October, 2013

Teresa Stanek Rea
*Deputy Director of the United States Patent and Trademark Office*

CERTIFICATE OF CORRECTION (continued)
U.S. Pat. No. 8,158,585 B2

In the drawings:

In FIG. 2, Panel A            change "□" to --Δ--
In FIG. 2, Panel C            change two instances of "A°" to --Å--
In FIG. 8 (page 2), Panel J    change five instances of "A°" to --Å--

Replace FIG. 2, Panel A with the following amended figure:

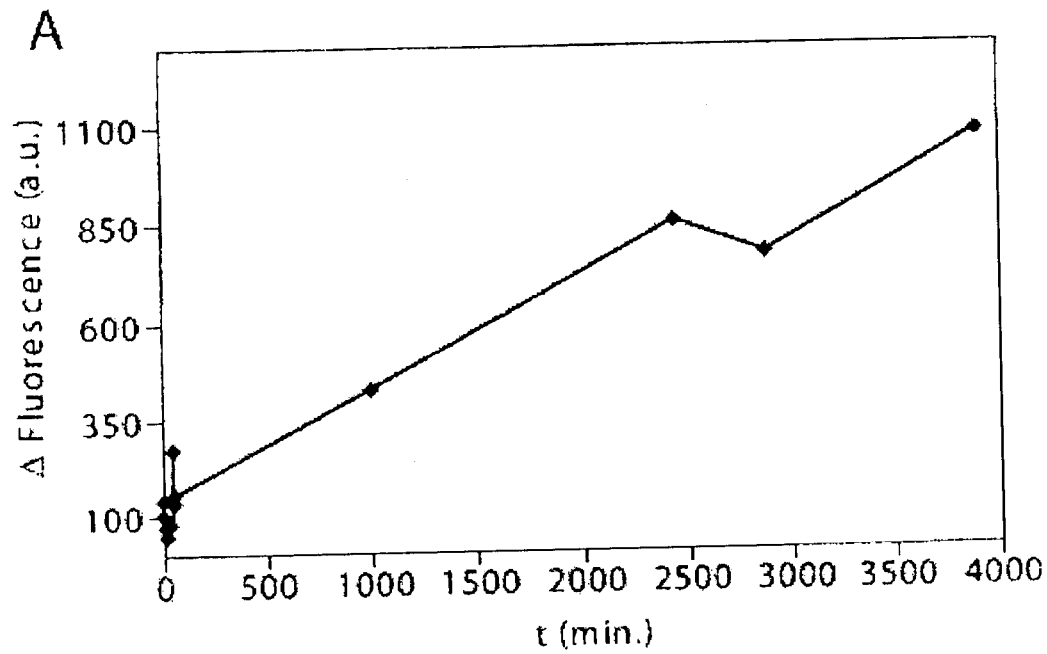

Replace FIG. 2, Panel C with the following amended figure:

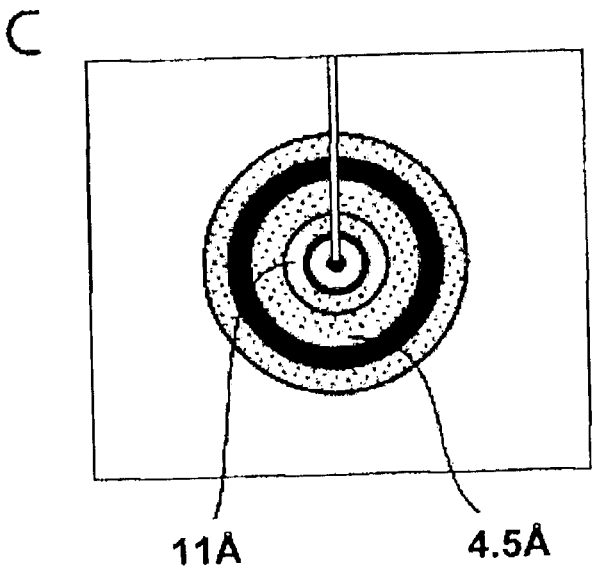

CERTIFICATE OF CORRECTION (continued)
U.S. Pat. No. 8,158,585 B2

Replace FIG. 8 (page 2), Panel J with the following amended figure:

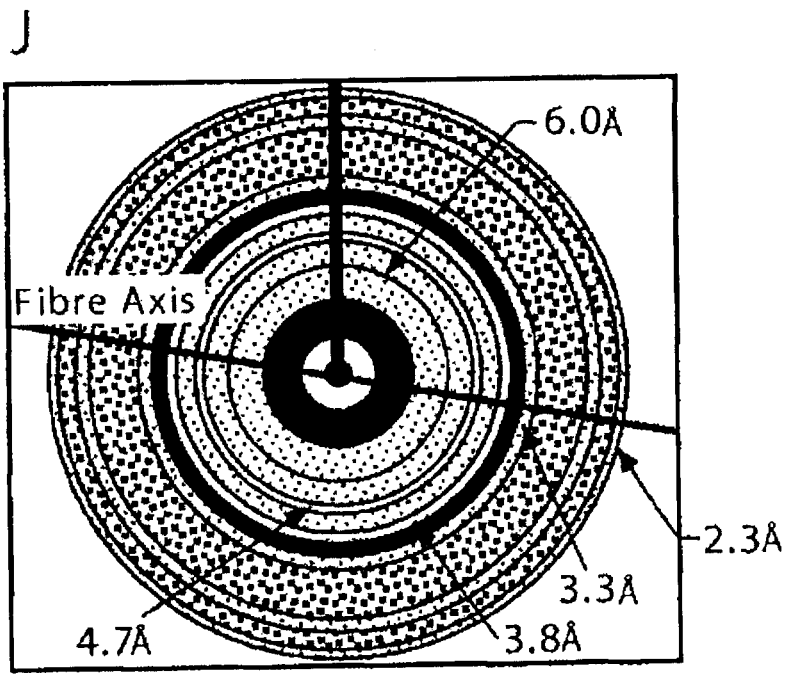

In the specification:

| | | |
|---|---|---|
| COLUMN 42, | LINE 63, | change "binds bound" to --bound-- |
| COLUMN 43, | LINE 39, | change "binds bound" to --bound-- |

SEQUENCE LISTING

```
<160> NUMBER OF SEQ ID NOS: 45

<210> SEQ ID NO 1
<211> LENGTH: 26
<212> TYPE: PRT
<213> ORGANISM: Artificial Sequence
<220> FEATURE:
<223> OTHER INFORMATION: Part of tpA from Homo sapiens
<220> FEATURE:
<221> NAME/KEY: MISC_FEATURE
<222> LOCATION: (2)..(2)
<223> OTHER INFORMATION: "Xaa" stands for unknown amino acid
<220> FEATURE:
<221> NAME/KEY: MISC_FEATURE
<222> LOCATION: (4)..(16)
<223> OTHER INFORMATION: "Xaa" stands for unknown amino acid
<220> FEATURE:
<221> NAME/KEY: MISC_FEATURE
<222> LOCATION: (18)..(23)
<223> OTHER INFORMATION: "Xaa" stands for unknown amino acid
<220> FEATURE:
<221> NAME/KEY: MISC_FEATURE
<222> LOCATION: (25)..(25)
<223> OTHER INFORMATION: "Xaa" stands for unknown amino acid

<400> SEQUENCE: 1

Arg Xaa Glu Xaa Xaa Xaa Xaa Xaa Xaa Xaa Xaa Xaa Xaa Xaa Xaa Xaa
1               5                   10                  15

Arg Xaa Xaa Xaa Xaa Xaa Xaa Arg Xaa Glu
            20                  25

<210> SEQ ID NO 2
<211> LENGTH: 8
<212> TYPE: PRT
<213> ORGANISM: Artificial Sequence
<220> FEATURE:
<223> OTHER INFORMATION: Part of fibronectin from Homo sapiens
<220> FEATURE:
<221> NAME/KEY: misc_feature
<222> LOCATION: (2)..(2)
<223> OTHER INFORMATION: Xaa can be any naturally occurring amino acid
```

```
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 2

Arg Xaa Glu Xaa Lys Xaa Glu Arg
1               5

<210> SEQ ID NO 3
<211> LENGTH: 50
<212> TYPE: PRT
<213> ORGANISM: Artificial Sequence
<220> FEATURE:
<223> OTHER INFORMATION: Finger domain of tPA from Homo sapiens

<400> SEQUENCE: 3

Ser Tyr Gln Val Ile Cys Arg Asp Glu Lys Thr Gln Met Ile Tyr Gln
1               5                   10                  15

Gln His Gln Ser Trp Leu Arg Pro Val Leu Arg Ser Asn Arg Val Glu
            20                  25                  30

Tyr Cys Trp Cys Asn Ser Gly Arg Ala Gln Cys His Ser Val Pro Val
        35                  40                  45

Lys Ser
    50

<210> SEQ ID NO 4
<211> LENGTH: 47
<212> TYPE: PRT
<213> ORGANISM: Artificial Sequence
<220> FEATURE:
<223> OTHER INFORMATION: Finger domain of FXII from Homo sapiens

<400> SEQUENCE: 4

Gln Lys Glu Lys Cys Phe Glu Pro Gln Leu Leu Arg Phe Phe His Lys
1               5                   10                  15

Asn Glu Ile Trp Tyr Arg Thr Glu Gln Ala Ala Val Ala Arg Cys Gln
            20                  25                  30

Cys Lys Gly Pro Asp Ala His Cys Gln Arg Leu Ala Ser Gln Ala
        35                  40                  45

<210> SEQ ID NO 5
<211> LENGTH: 47
<212> TYPE: PRT
<213> ORGANISM: Artificial Sequence
<220> FEATURE:
<223> OTHER INFORMATION: Finger domain of HGFa from Homo sapiens

<400> SEQUENCE: 5

Gly Thr Glu Lys Cys Phe Asp Glu Thr Arg Tyr Glu Tyr Leu Glu Gly
1               5                   10                  15

Gly Asp Arg Trp Ala Arg Val Arg Gln Gly His Val Glu Gln Cys Glu
            20                  25                  30

Cys Phe Gly Gly Arg Thr Trp Cys Glu Gly Thr Arg His Thr Ala
        35                  40                  45

<210> SEQ ID NO 6
<211> LENGTH: 44
<212> TYPE: PRT
<213> ORGANISM: Artificial Sequence
```

```
<220> FEATURE:
<223> OTHER INFORMATION: Finger domain of FN1-1 from Homo sapiens

<400> SEQUENCE: 6

Ser Lys Pro Gly Cys Tyr Asp Asn Gly Lys His Tyr Gln Ile Asn Gln
1               5                   10                  15

Gln Trp Glu Arg Thr Tyr Leu Gly Asn Val Leu Val Cys Thr Cys Tyr
            20                  25                  30

Gly Gly Ser Arg Gly Phe Asn Cys Glu Ser Lys Pro
        35                  40

<210> SEQ ID NO 7
<211> LENGTH: 49
<212> TYPE: PRT
<213> ORGANISM: Artificial Sequence
<220> FEATURE:
<223> OTHER INFORMATION: Finger domain of FN1-2 from Homo sapiens

<400> SEQUENCE: 7

Glu Ala Glu Glu Thr Cys Phe Asp Lys Tyr Thr Gly Asn Thr Tyr Arg
1               5                   10                  15

Val Gly Asp Thr Tyr Glu Arg Pro Lys Asp Ser Met Ile Trp Asp Cys
            20                  25                  30

Thr Cys Ile Gly Ala Gly Arg Gly Arg Ile Ser Cys Thr Ile Ala Asn
        35                  40                  45

Arg

<210> SEQ ID NO 8
<211> LENGTH: 50
<212> TYPE: PRT
<213> ORGANISM: Artificial Sequence
<220> FEATURE:
<223> OTHER INFORMATION: Finger domain of FN1-3 from Homo sapiens

<400> SEQUENCE: 8

Thr Ile Ala Asn Arg Cys His Glu Gly Gly Gln Ser Tyr Lys Ile Gly
1               5                   10                  15

Asp Thr Trp Arg Arg Pro His Glu Thr Gly Gly Tyr Met Leu Glu Cys
            20                  25                  30

Val Cys Leu Gly Asn Gly Lys Gly Glu Trp Thr Cys Lys Pro Ile Ala
        35                  40                  45

Glu Lys
    50

<210> SEQ ID NO 9
<211> LENGTH: 51
<212> TYPE: PRT
<213> ORGANISM: Artificial Sequence
<220> FEATURE:
<223> OTHER INFORMATION: Finger domain of FN1-4 from Homo sapiens

<400> SEQUENCE: 9

Lys Pro Ile Ala Glu Lys Cys Phe Asp His Ala Ala Gly Thr Ser Tyr
1               5                   10                  15

Val Val Gly Glu Thr Trp Glu Lys Pro Tyr Gln Gly Trp Met Met Val
            20                  25                  30

Asp Cys Thr Cys Leu Gly Glu Gly Ser Gly Arg Ile Thr Cys Thr Ser
        35                  40                  45

Arg Asn Arg
    50
```

```
<210> SEQ ID NO 10
<211> LENGTH: 52
<212> TYPE: PRT
<213> ORGANISM: Artificial Sequence
<220> FEATURE:
<223> OTHER INFORMATION: Finger domain of FN1-5 from Homo sapiens

<400> SEQUENCE: 10

Thr Ser Arg Asn Arg Cys Asn Asp Gln Asp Thr Arg Thr Ser Tyr Arg
1               5                   10                  15

Ile Gly Asp Thr Trp Ser Lys Lys Asp Asn Arg Gly Asn Leu Leu Gln
                20                  25                  30

Cys Ile Cys Thr Gly Asn Gly Arg Gly Glu Trp Lys Cys Glu Arg His
            35                  40                  45

Thr Ser Val Gln
        50

<210> SEQ ID NO 11
<211> LENGTH: 45
<212> TYPE: PRT
<213> ORGANISM: Artificial Sequence
<220> FEATURE:
<223> OTHER INFORMATION: Finger domain of FN1-6 from Homo sapiens

<400> SEQUENCE: 11

Pro Pro Tyr Gly His Cys Val Thr Asp Ser Gly Val Val Tyr Ser Val
1               5                   10                  15

Gly Met Gln Trp Leu Lys Thr Gln Gly Asn Lys Gln Met Leu Cys Thr
                20                  25                  30

Cys Leu Gly Asn Gly Val Ser Cys Gln Glu Thr Ala Val
            35                  40                  45

<210> SEQ ID NO 12
<211> LENGTH: 56
<212> TYPE: PRT
<213> ORGANISM: Artificial Sequence
<220> FEATURE:
<223> OTHER INFORMATION: Finger domain of FN1-7 from Homo sapiens

<400> SEQUENCE: 12

Pro Met Ala Ala His Glu Glu Ile Cys Thr Thr Asn Glu Gly Val Met
1               5                   10                  15

Tyr Arg Ile Gly Asp Gln Trp Asp Lys Gln His Asp Met Gly His Met
                20                  25                  30

Met Arg Arg Cys Thr Cys Val Gly Asn Gly Arg Gly Glu Trp Thr Cys
            35                  40                  45

Ile Ala Tyr Ser Gln Leu Arg Asp
        50                  55

<210> SEQ ID NO 13
<211> LENGTH: 52
<212> TYPE: PRT
<213> ORGANISM: Artificial Sequence
<220> FEATURE:
<223> OTHER INFORMATION: Finger domain of FN1-8 from Homo sapiens

<400> SEQUENCE: 13

Ile Ala Tyr Ser Gln Leu Arg Asp Gln Cys Ile Val Asp Asp Ile Thr
1               5                   10                  15

Tyr Asn Val Asn Asp Thr Phe His Lys Arg His Glu Glu Gly His Met
                20                  25                  30
```

```
Leu Asn Cys Thr Cys Phe Gly Gln Gly Arg Gly Arg Trp Lys Cys Asp
         35                  40                  45

Pro Val Asp Gln
    50

<210> SEQ ID NO 14
<211> LENGTH: 54
<212> TYPE: PRT
<213> ORGANISM: Artificial Sequence
<220> FEATURE:
<223> OTHER INFORMATION: Finger domain of FN1-9 from Homo sapiens

<400> SEQUENCE: 14

Trp Lys Cys Asp Pro Val Asp Gln Cys Gln Asp Ser Glu Thr Gly Thr
1               5                   10                  15

Phe Gln Ile Gly Asp Ser Trp Glu Lys Tyr Val His Gly Val Arg Tyr
            20                  25                  30

Gln Cys Tyr Cys Tyr Gly Arg Gly Ile Gly Glu Trp His Cys Gln Pro
        35                  40                  45

Leu Gln Thr Tyr Pro Ser
    50

<210> SEQ ID NO 15
<211> LENGTH: 53
<212> TYPE: PRT
<213> ORGANISM: Artificial Sequence
<220> FEATURE:
<223> OTHER INFORMATION: Finger domain of FN1-10 from Homo sapiens

<400> SEQUENCE: 15

Asn Gln Pro Thr Asp Asp Ser Cys Phe Asp Pro Tyr Thr Val Ser His
1               5                   10                  15

Tyr Ala Val Gly Asp Glu Trp Glu Arg Met Ser Ser Glu Ser Gly Phe
            20                  25                  30

Lys Leu Leu Cys Gln Cys Leu Gly Phe Gly Ser Gly His Phe Arg Cys
        35                  40                  45

Asp Ser Ser Arg Trp
    50

<210> SEQ ID NO 16
<211> LENGTH: 49
<212> TYPE: PRT
<213> ORGANISM: Artificial Sequence
<220> FEATURE:
<223> OTHER INFORMATION: Finger domain of FN1-11 from Homo sapiens

<400> SEQUENCE: 16

Asp Ser Ser Arg Trp Cys His Asp Asn Gly Val Asn Tyr Lys Ile Gly
1               5                   10                  15

Glu Lys Trp Asp Arg Gln Gly Glu Asn Gly Gln Met Met Ser Cys Thr
            20                  25                  30

Cys Leu Gly Asn Gly Lys Gly Glu Phe Lys Cys Asp Pro His Glu Ala
        35                  40                  45

Thr

<210> SEQ ID NO 17
<211> LENGTH: 50
<212> TYPE: PRT
<213> ORGANISM: Artificial Sequence
<220> FEATURE:
<223> OTHER INFORMATION: Finger domain of FN1-12 from Homo sapiens
```

```
<400> SEQUENCE: 17

Asp Pro His Glu Ala Thr Cys Tyr Asp Asp Gly Lys Thr Tyr His Val
1               5                   10                  15

Gly Glu Gln Trp Gln Lys Glu Tyr Leu Gly Ala Ile Cys Ser Cys Thr
                20                  25                  30

Cys Phe Gly Gly Gln Arg Gly Trp Arg Cys Asp Asn Cys Arg Arg Pro
            35                  40                  45

Gly Gly
    50

<210> SEQ ID NO 18
<211> LENGTH: 40
<212> TYPE: PRT
<213> ORGANISM: Artificial Sequence
<220> FEATURE:
<223> OTHER INFORMATION: Peptide A Beta (1-40) from Homo sapiens

<400> SEQUENCE: 18

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val
            35                  40

<210> SEQ ID NO 19
<211> LENGTH: 13
<212> TYPE: PRT
<213> ORGANISM: Artificial Sequence
<220> FEATURE:
<223> OTHER INFORMATION: Peptide FP13 from Homo sapiens

<400> SEQUENCE: 19

Lys Arg Leu Glu Val Asp Ile Asp Ile Lys Ile Arg Ser
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Peptide FP12 from Homo sapiens

<400> SEQUENCE: 20

Lys Arg Leu Glu Val Asp Ile Asp Ile Lys Ile Arg
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Peptide FP10 from Homo sapiens

<400> SEQUENCE: 21

Lys Arg Leu Glu Val Asp Ile Asp Ile Lys
1               5                   10

<210> SEQ ID NO 22
<211> LENGTH: 37
<212> TYPE: PRT
<213> ORGANISM: Artificial Sequence
<220> FEATURE:
<223> OTHER INFORMATION: Peptide fl-hIAPP from Homo sapiens
```

-continued

```
<400> SEQUENCE: 22

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 23
<211> LENGTH: 10
<212> TYPE: PRT
<213> ORGANISM: Artificial Sequence
<220> FEATURE:
<223> OTHER INFORMATION: Peptide Delta hIAPP from Homo sapiens

<400> SEQUENCE: 23

Ser Asn Asn Phe Gly Ala Ile Leu Ser Ser
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Peptide Delta mIAPP from Homo sapiens

<400> SEQUENCE: 24

Ser Asn Asn Leu Gly Pro Val Leu Pro Pro
1               5                   10

<210> SEQ ID NO 25
<211> LENGTH: 38
<212> TYPE: DNA
<213> ORGANISM: Artificial Sequence
<220> FEATURE:
<223> OTHER INFORMATION: Primer

<400> SEQUENCE: 25
aaaagtcgac agccgccacc atggatgcaa tgaagaga                            38

<210> SEQ ID NO 26
<211> LENGTH: 33
<212> TYPE: DNA
<213> ORGANISM: Artificial Sequence
<220> FEATURE:
<223> OTHER INFORMATION: Primer

<400> SEQUENCE: 26
aaaagcggcc gcccactttt gacaggcact gag                                 33

<210> SEQ ID NO 27
<211> LENGTH: 32
<212> TYPE: DNA
<213> ORGANISM: Artificial Sequence
<220> FEATURE:
<223> OTHER INFORMATION: Primer

<400> SEQUENCE: 27
aaaagcggcc gcgtggccct ggtatctatt tc                                  32

<210> SEQ ID NO 28
<211> LENGTH: 29
<212> TYPE: DNA
<213> ORGANISM: Artificial Sequence
<220> FEATURE:
<223> OTHER INFORMATION: Primer
```

<400> SEQUENCE: 28
aaaagagatc tgtgcctgtc aaaagttgc                                            29

<210> SEQ ID NO 29
<211> LENGTH: 32
<212> TYPE: DNA
<213> ORGANISM: Artificial Sequence
<220> FEATURE:
<223> OTHER INFORMATION: Primer

<400> SEQUENCE: 29
aaaagagatc tgataccagg gccacgtgct ac                                        32

<210> SEQ ID NO 30
<211> LENGTH: 35
<212> TYPE: DNA
<213> ORGANISM: Artificial Sequence
<220> FEATURE:
<223> OTHER INFORMATION: Primer

<400> SEQUENCE: 30
aaaagcggcc gcccgtcact gtttccctca gagca                                     35

<210> SEQ ID NO 31
<211> LENGTH: 30
<212> TYPE: DNA
<213> ORGANISM: Artificial Sequence
<220> FEATURE:
<223> OTHER INFORMATION: Primer

<400> SEQUENCE: 31
aaagcggccg cctggctcct cttctgaatc                                           30

<210> SEQ ID NO 32
<211> LENGTH: 31
<212> TYPE: DNA
<213> ORGANISM: Artificial Sequence
<220> FEATURE:
<223> OTHER INFORMATION: Primer

<400> SEQUENCE: 32
tgcaagatct atagctgaga agtgttttga t                                         31

<210> SEQ ID NO 33
<211> LENGTH: 35
<212> TYPE: DNA
<213> ORGANISM: Artificial Sequence
<220> FEATURE:
<223> OTHER INFORMATION: Primer

<400> SEQUENCE: 33
gatgcggccg ccctgtattc ctagaagtgc aagtg                                     35

<210> SEQ ID NO 34
<211> LENGTH: 31
<212> TYPE: DNA
<213> ORGANISM: Artificial Sequence
<220> FEATURE:
<223> OTHER INFORMATION: Primer

<400> SEQUENCE: 34
tgcaagatct acttctagaa atagatgcaa c                                         31

```
<210> SEQ ID NO 35
<211> LENGTH: 32
<212> TYPE: DNA
<213> ORGANISM: Artificial Sequence
<220> FEATURE:
<223> OTHER INFORMATION: Primer

<400> SEQUENCE: 35
tgatgcggcc gccccacaga ggtgtgcctc tc                                32

<210> SEQ ID NO 36
<211> LENGTH: 31
<212> TYPE: DNA
<213> ORGANISM: Artificial Sequence
<220> FEATURE:
<223> OTHER INFORMATION: Primer

<400> SEQUENCE: 36
aaaaaagatc taaccaacct acggatgact c                                 31

<210> SEQ ID NO 37
<211> LENGTH: 32
<212> TYPE: DNA
<213> ORGANISM: Artificial Sequence
<220> FEATURE:
<223> OTHER INFORMATION: Primer

<400> SEQUENCE: 37
aaaaaaggta ccgactgggt tcaccccag gt                                 32

<210> SEQ ID NO 38
<211> LENGTH: 32
<212> TYPE: DNA
<213> ORGANISM: Artificial Sequence
<220> FEATURE:
<223> OTHER INFORMATION: Primer

<400> SEQUENCE: 38
gaaacaagat ctcagaaaga gaagtgcttt ga                                32

<210> SEQ ID NO 39
<211> LENGTH: 34
<212> TYPE: DNA
<213> ORGANISM: Artificial Sequence
<220> FEATURE:
<223> OTHER INFORMATION: Primer

<400> SEQUENCE: 39
acgggcggcc gcccggcctg gctggccagc cgct                              34

<210> SEQ ID NO 40
<211> LENGTH: 31
<212> TYPE: DNA
<213> ORGANISM: Artificial Sequence
<220> FEATURE:
<223> OTHER INFORMATION: Primer

<400> SEQUENCE: 40
aaaaaagatc tcagaaagag aagtgctttg a                                 31

<210> SEQ ID NO 41
<211> LENGTH: 31
<212> TYPE: DNA
<213> ORGANISM: Artificial Sequence
<220> FEATURE:
<223> OTHER INFORMATION: Primer
```

```
<400> SEQUENCE: 41
aaaaaggtac cggcttgcct tggtgtccac g                              31

<210> SEQ ID NO 42
<211> LENGTH: 32
<212> TYPE: DNA
<213> ORGANISM: Artificial Sequence
<220> FEATURE:
<223> OTHER INFORMATION: Primer

<400> SEQUENCE: 42
gcaagaagat ctggcacaga gaaatgcttt ga                             32

<210> SEQ ID NO 43
<211> LENGTH: 34
<212> TYPE: DNA
<213> ORGANISM: Artificial Sequence
<220> FEATURE:
<223> OTHER INFORMATION: Primer

<400> SEQUENCE: 43
aagggcggcc gcccagctgt atgtcgggtg cctt                           34

<210> SEQ ID NO 44
<211> LENGTH: 30
<212> TYPE: DNA
<213> ORGANISM: Artificial Sequence
<220> FEATURE:
<223> OTHER INFORMATION: Primer

<400> SEQUENCE: 44
aaaaaagatc tggcacagag aatgctttga                                30

<210> SEQ ID NO 45
<211> LENGTH: 31
<212> TYPE: DNA
<213> ORGANISM: Artificial Sequence
<220> FEATURE:
<223> OTHER INFORMATION: Primer

<400> SEQUENCE: 45
aaaaaggtac cgctcatcag gctcgatgtt g                              31
```